US011124810B2

(12) United States Patent
Toivari et al.

(10) Patent No.: US 11,124,810 B2
(45) Date of Patent: Sep. 21, 2021

(54) PRODUCTION OF OXALYL-COA, GLYOXYLATE AND/OR GLYCOLIC ACID

(71) Applicant: TEKNOLOGIAN TUTKIMUSKESKUS VTT OY, Espoo (FI)

(72) Inventors: Mervi Toivari, VTT (FI); Marja Ilmén, VTT (FI); Merja Penttilä, VTT (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 0 days.

(21) Appl. No.: 16/633,608

(22) PCT Filed: Jul. 27, 2018

(86) PCT No.: PCT/FI2018/050557

§ 371 (c)(1),
(2) Date: Jan. 24, 2020

(87) PCT Pub. No.: WO2019/020870

PCT Pub. Date: Jan. 31, 2019

(65) Prior Publication Data

US 2020/0199632 A1 Jun. 25, 2020

(30) Foreign Application Priority Data

Jul. 28, 2017 (FI) .................................... 20175703

(51) Int. Cl.

| | |
|---|---|
| ***C12N 9/88*** | (2006.01) |
| ***C12P 7/26*** | (2006.01) |
| ***C12P 7/42*** | (2006.01) |
| ***C12N 9/14*** | (2006.01) |
| ***C12N 9/00*** | (2006.01) |
| ***C12P 5/02*** | (2006.01) |

(52) U.S. Cl.

CPC .................. *C12P 7/42* (2013.01); *C12N 9/14* (2013.01); *C12N 9/88* (2013.01); *C12N 9/93* (2013.01); *C12P 5/026* (2013.01); *C12Y 307/01001* (2013.01); *C12Y 602/01008* (2013.01); *C12Y 604/01001* (2013.01)

(58) Field of Classification Search

CPC ................ C12P 7/42; C12N 9/88; C12N 1/16
See application file for complete search history.

(56) References Cited

U.S. PATENT DOCUMENTS 9,783,809 B2 * 10/2017 Koivistoinen ......... C12N 15/52

FOREIGN PATENT DOCUMENTS

| | | | |
|---|---|---|---|
| WO | 2007141316 | A2 | 12/2007 |
| WO | 2011036213 | A2 | 3/2011 |
| WO | 2013050659 | A1 | 4/2013 |
| WO | 2014105805 | A2 | 7/2014 |
| WO | 2014162063 | A1 | 10/2014 |
| WO | 2016018036 | A1 | 2/2016 |
| WO | 2016193540 | A1 | 12/2016 |
| WO | 2017040719 | A1 | 3/2017 |

OTHER PUBLICATIONS

Finnish Patent and Registration Office, Search report of FI20175703 dated Jan. 22, 2018, 2 pages.

Gädda et al: "The industrial potential of bio-based glycolic acid and polyglycolic acid," APPITA, vol. 67, 2014, p. 352, XP009507854.

Foster et al: "An oxalyl-CoA synthetase is important for oxalate metabolism in *Saccharomyces cerevisiae*", FEBS Letters, 2014, vol. 588, No. 1, pp. 160-166, XP055320823.

Koivistoinen et al: "Glycolic acid production in the engineered yeasts *Saccharomyces* and *Kluyveromyces lactis*", Microbial Cell Factories, vol. 12, 2013, pp. 1-16, XP021164132.

Koivistoinen: "Catabolism of biomass-derived sugars in fungi and metabolic engineering as a tool for organic acid production", University of Helsinki, Thesis, 2013, pp. 1-86, XP002784470.

Schneider et al: "Oxalyl-Coenzyme A reduction to glyoxylate is the preferred route of oxalate assimilation in Methylobacterium extorquens AM1", In: Journal of Bacteriology, Jun. 2012, vol. 194, pp. 3144-3155, XP002784523.

Baritugo et al: "Metabolic engineering of Corynebacterium glutamicum for fermentative production of chemicals in biorefinery", Applied Microbiology and Biotechnology, vol. 102, Mar. 20, 2018, pp. 3915-3937, XP036477576.

Salusjärvi et al: "Production of ethylene glycol or glycolic acid from D-xylose in *Saccharomyces cerevisiae*", Applied Microbiology and Biotechnology, vol. 101, Oct. 16, 2017, pp. 8151-8163, XP036347977.

Toivari: "Fungi—excellent hosts for production of organic acids in Finland", World Congress on Industrial Biotechnology Conference paper (Abstract) Apr. 19, 2016, pp. 2-3, XP002784463.

Koivstoinen et al: "Engineering yeast for production of glycolic acid", Metabolic Engineering 11, conference, Awaji Island, Japan, Jun. 26-30, 2016 Conference Abstract, 2016, p. 1, 13, XP002784464.

Aguilera et al: "Physiological and genome-wide transcriptional responses of *Saccharomyces cerevisiae* to high carbon dioxide concentrations", Nov. 25, 2004, FEMS Yeast Research 5 (2005), pp. 579-593.

(Continued)

*Primary Examiner* — Tekchand Saidha
(74) *Attorney, Agent, or Firm* — Merchant & Gould P.C.

(57) ABSTRACT

The present invention relates to a method of converting oxalate to oxalyl-coA and/or oxalyl-coA to glyoxylate in a fungus and to a method of producing glycolic acid. Still, the present invention relates to a genetically modified fungus comprising increased enzyme activity associated with oxalyl-CoA. And furthermore, the present invention relates to use of the fungus of the present invention for producing oxalate, oxalyl-coA, glyoxylate and/or glycolic acid from a carbon substrate. Still furthermore, the present invention relates to a method of producing specific products and to a method of preparing the genetically modified fungus of the present invention.

21 Claims, 2 Drawing Sheets

Specification includes a Sequence Listing.

(56) References Cited

OTHER PUBLICATIONS

Amoroso et al: "The gene NCE103 (YNL036w) from *Saccharomyces cerevisiae* encodes a functional carbonic anhydrase and its transcription is regulated by the concentration of inorganic carbon in the medium", Molecular Microbiology (2005), 56(2), pp. 549-558.
Anderson et al: "Isopentenyl Diphosphate: Dimethylallyl Diphosphate Isomerase an improved purification of the enzyme and isolation of the gene from *Saccharomyces cerevisiae*" The Journal Biological Chemistry, vol. 264, No. 32, Issue of Nov. 15, pp. 19169-19175, 1989.
Basson et al: "*Saccharomyces cerevisiae* contains two functional genes encoding 3-hydroxy-3-methylglutaryl-coenzyme A reductase", Proc. Natl. Acad. Sci. USA, vol. 83, pp. 5563-5567, Aug. 1986 Genetics.
Blobel et al: "Identification of a yeast peroxisomal member of the family of AMP-binding proteins", Eur. J. Bicohem, 240, 468-476 (1996), FEBS 1996.
Brewster et al: "Regulation of Pyruvate Carboxylase Isozyme (PYC1, PYC2) Gene Expression in *Saccharomyces cerevisiae* during Fermentative and Nonfermentative Growth", Archives of Biochemistry and Biophysics, vol. 311, No. 1, May 15, pp. 62-71, 1994.
Gombert et al: "Functional characterization of of the oxaloacetase encoding gene and elimination of oxalate formation in the β-lactam producer Penicillium chrysogenum", Elsevier, Fungal Genetics and Biology 48 (2011) 831-839.
Hoover et al: "Characteristics of an *Arabidopsis glyoxylate* reductase: general biochemical properties and substrate specificity for the recombinant protein, and developmental expression and implications for glyoxylate and succinic semialdehyde metabolism in planta", Canadian Journal of Botany 85: pp. 883-895, Sep. 2007.
Ilmén et al: "Identification of novel isoprene synthases through genome mining and expression in *Escherichia coli*", Elsevier, Metabolic Engineering 31 (2015), 153-162.
Kobayashi et al: "Oxalic acid production by citric acid-producing *Apergillus niger* overexpressing the oxaloacetate hydrolase gene oahA", J Ind Microbiol Biotechnol (2014) 41:749-756.
Mayer et al: "Disruption and Mapping of IDI1, the Gene for Isopentenyl Diphosphate Isomerase in *Saccharomyces cerevisiae*", Yeast vol. 8: 743-748 (1992).
Mishina et al: "Yeast Mutants Defective in Acetyl-Coentzyme A Carboxylase and Biotin: Apocarboxylase Ligase", Eur. J. Biochem 111, 79-87 (1980), FEBS 1980.
Polakowski et al: "Overexpression of a cytosolic hydroxymethylglutaryl-CoA reductase leads to squalene accumulation in yeast", Appl Microbiol Biotechnol (1998) 49: 66-71, Springer-Verlag 1998.
Runguphan et al: "Metabolic engineering of *Saccharomyces cerevisiae* for production of fatty acid-derived biofuels and chemicals", Metabolic Engineering, Elsevier, 2013, 11 pages.
Salanoubat et al: "Sequence and analysis of chromosome 3 of the plant *Arabidopsis thaliana*", Nature, vol. 408, Dec. 14, 2000, pp. 820-822.
Schweizer et al: "The pentafunctional FAS1 gene of yeast: its nucleotide sequence and order of the catalytic domains", Mol Gen Genet (1986) 203: 479-486; Springer Verlag 1986.
Steensma et al: "Plasmids with the Cre-recombinase and the dominant nat marker, suitable for use in prototrophic strains of *Saccharomyces cerevisiae* and Kluyveromyces lactis", Yeast Functional Analysis Report, Yeast 2001; 18: 469-472.
Walker et al: "Yeast pyruvate caboxylase: Identification of two genes encoding isoenzymes", Biochemical and Biophysical Research Communication, vol. 176, No. 3, 1991, May 15, 1991, pp. 1210-1217.

* cited by examiner

PRODUCTION OF OXALYL-COA, GLYOXYLATE AND/OR GLYCOLIC ACID

PRIORITY

This application is a U.S. national application of the international application number PCT/F12018/050557 filed on Jul. 27, 2018 and claiming priority of Finnish application 20175703 filed on Jul. 28, 2017 the contents of all of which are incorporated herein by reference.

FIELD OF THE INVENTION

The present invention relates to the fields of industrial biotechnology, microbial production organisms and bio-based chemicals. Specifically, the invention relates to a method of converting oxalate to oxalyl-coA and/or oxalyl-coA to glyoxylate in a fungus and to a method of producing oxalyl-CoA, glyoxylate and/or glycolic acid. Still, the present invention relates to a genetically modified fungus comprising increased enzyme activity associated with oxalyl-CoA. And furthermore, the present invention relates to use of the fungus of the present invention for producing oxalate, oxalyl-coA, glyoxylate and/or glycolic acid from a carbon substrate, or to use of the fungus of the present invention for producing polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, or pharmaceuticals. Still furthermore, the present invention relates to a method of producing specific products and to a method of preparing the genetically modified fungus of the present invention.

BACKGROUND OF THE INVENTION

Glycolic acid (chemical formula $C_2H_4O_3$) is a 2-carbon organic acid that can be used e.g. in polymers as well as in cleaning and skin-care applications. Glycolic acids occur naturally but are mainly synthetically produced.

Compared to synthetic production of glycolic acids industrial fermentation enables reduction of used energy and water resources. Also, by fermentation processes fossil carbon resources as well as chemicals utilized in the chemical synthesis can be avoided. Among other applications fermentation processes have also been exploited in production of glycolic acids. Genetically modified bacteria have been used as hosts for producing glycolic acid by fermentation as exemplified e.g. in WO2007141316 A2 and WO2011036213 A2.

To date, some genetic modifications have been tested for engineering the fungal glyoxylate cycle for production of glycolic acid. As an example WO2016/193540 A1 describes a genetically modified fungal cell overexpressing a gene encoding glyoxylate reductase activity. Glyoxylate reductase converts glyoxylate to glycolic acid. In WO2016/193540 A1 said fungal cell is utilized in a method for producing glycolic acid and said publication illustrates a modification of a pathway converting isocitrate to glyoxylate for increased production of glycolic acid. Also WO2013/050659 A1 describes fungal cells having genetic modifications of glyoxylate reductase and having ability to produce glycolic acid.

Despite of the progress in glycolic acid production there are remaining challenges for example in low yield, compartmentalization, allosteric regulation, glucose repression, cofactor imbalance and production of several (unwanted) by-products.

BRIEF DESCRIPTION OF THE INVENTION

The present invention describes a novel biotechnical production method of oxalyl-CoA, glyoxylate and/or glycolic acid from pyruvate by fermentation. The object of the invention is to provide synthetic biological applications for sustainable bioeconomy. Producing glycolic acid directly from renewable sources is a green alternative and at the same time an industrially feasible production process.

The present invention surprisingly reveals improved production of oxalyl-coA, glyoxylate and/or glycolic acid or any combination thereof. By utilizing genetic modifications great yields of oxalyl-coA, glyoxylate and/or glycolic acid or any combination thereof may be produced in fungi (FIG. 1). The objects of the invention are achieved by utilizing a synthetic metabolic pathway converting pyruvate and $CO_2$ or alternatively pyruvate to glycolic acid via oxalate/oxalyl-CoA/glyoxylate (FIG. 1), or any part of said pathway.

Specifically the present invention reveals that by genetically modifying expression of one or more enzymes associated with oxalyl-CoA (e.g. enzymes converting oxalate to oxalyl-CoA and/or converting oxalyl-CoA to glyoxylate) increased yield of oxalyl-coA, glyoxylate and/or glycolic acid may be obtained.

The present invention is based on a novel pathway for glycolic acid production which results in better yield and lower oxygen consumption compared to the previously described methods. Indeed, the present invention improves carbon yield for glycolic acid. There is also either endogenous or exogenous $CO_2$ fixation involved, in case of oxaloacetate originating from pyruvate and $CO_2$.

The present fermentation process for production of bio-based chemicals is as carbon and energy efficient as possible. Indeed, the present invention provides a fast and high yield production process, which is suitable for an industrial scale. High yields of oxalyl-coA, glyoxylate and/or glycolic acid enable low production costs compared to the prior art. Also, the present invention provides efficient possibilities for further processing of high yields of glycolic acids.

Also, the present invention enables combination of the new synthetic metabolic pathway and the glyoxylate route for production of glycolic acid. By the present invention it is possible to concentrate on efficient production of only one or some main products instead of several by-products.

The present invention relates to a method of converting oxalate to oxalyl-coA and/or oxalyl-coA to glyoxylate in a fungus, said method comprising

- providing a fungus that has been genetically modified to increase an enzyme activity associated with oxalyl-CoA
- culturing said fungus in a carbon substrate containing medium to obtain oxalyl-coA and/or glyoxylate.

Also, the present invention relates to a method of producing oxalate, oxalyl-coA and/or glyoxylate in a fungus, said method comprising

- providing a fungus that has been genetically modified to increase an enzyme activity associated with oxalyl-CoA
- culturing said fungus in a carbon substrate containing medium to obtain oxalate, oxalyl-coA and/or glyoxylate.

Also, the present invention relates to a method of producing glycolic acid, said method comprising providing a fungus that has been genetically modified to increase an enzyme activity associated with oxalyl-CoA culturing said fungus in a carbon substrate containing medium to obtain glycolic acid.

Furthermore, the present invention relates to a genetically modified fungus comprising increased enzyme activity associated with oxalyl-CoA.

Still, the present invention relates to use of the fungus of the present invention for producing oxalate, oxalyl-coA, glyoxylate and/or glycolic acid from a carbon substrate.

Still, the present invention relates to a method of producing products selected from the group consisting of polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, and pharmaceuticals, said method comprising culturing the genetically modified fungus of the present invention in a carbon substrate containing medium to produce glycolic acids, recovering the resulting glycolic acids and utilizing the recovered glycolic acids in production of polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, or pharmaceuticals.

Still furthermore, the present invention relates to use of the genetically modified fungus of the present invention for producing polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, or pharmaceuticals.

And still furthermore, the present invention relates to a method of preparing the genetically modified fungus of the present invention, wherein said method comprises providing a fungus and genetically modifying the fungus to increase an enzyme activity associated with oxalyl-CoA.

Other objects, details and advantages of the present invention will become apparent from the following drawings, detailed description and examples.

Biomass, pyruvate and $CO_2$ are the main side products of the (oxalate) pathway utilized in the present invention. The invention is applicable for production/co-production of all acetate/acetyl-CoA derived compounds, for example lipids, terpenes, and polyketides. As an example, isoprene may be produced from acetyl-CoA.

Figure 2:
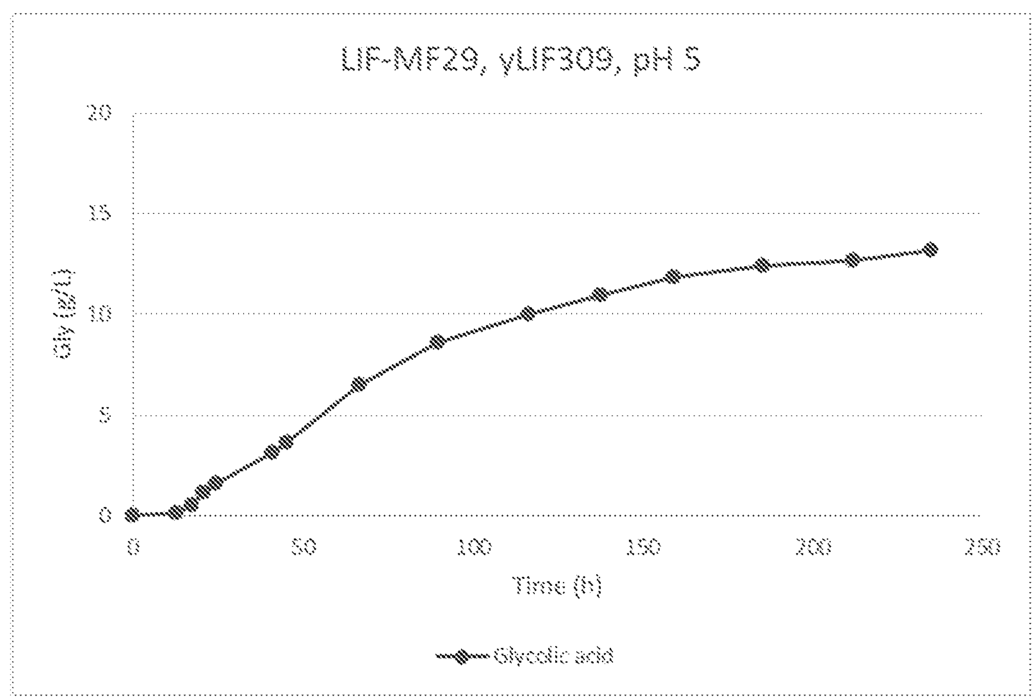

FIG. 2 shows production of glycolic acid from pyruvate by a genetically modified fungus.

Figure 3:
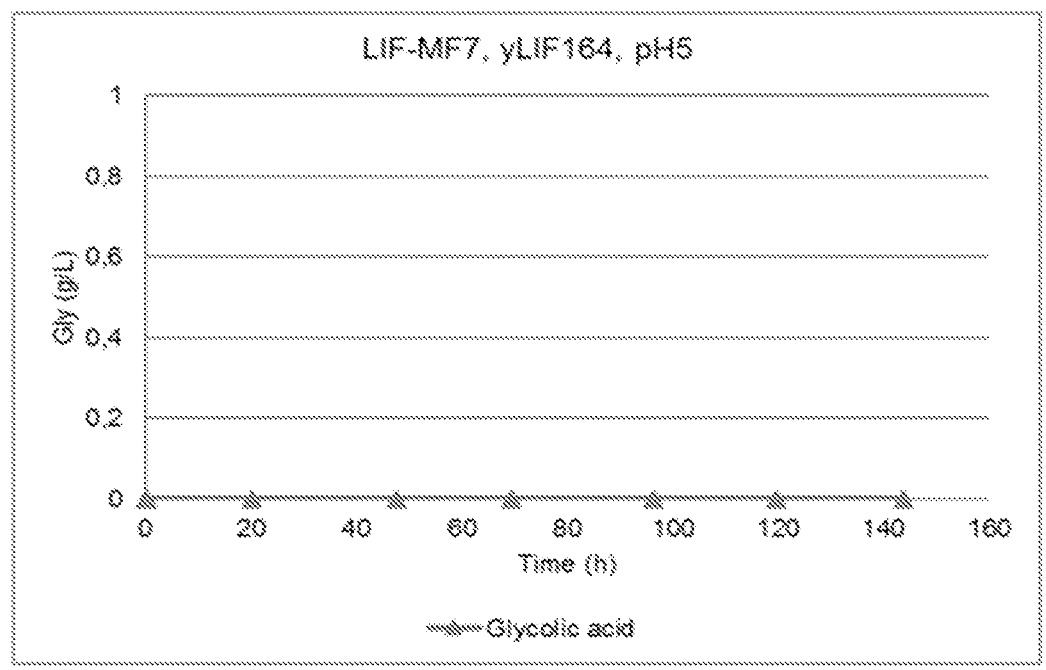

FIG. 3 reveals that a control fungus (i.e. not genetically modified according to the present invention) is not capable of producing glycolic acid from pyruvate.

DETAILED DESCRIPTION OF THE INVENTION

In the present invention a genetically modified fungus is utilized in a method of converting oxalate to oxalyl-coA and/or oxalyl-coA to glyoxylate (e.g. first oxalate to oxalyl-coA and then oxalyl-coA to glyoxylate) or in a method of producing oxalate, oxalyl-CoA, glyoxylate and/or glycolic acid.

As used herein "glycolic acid" refers to a monomer of polyglycolic acid.

In some embodiments of the present invention glycolic acid is produced via carboxylation of pyruvate to oxaloacetate (pyruvate is the normal intermediate in catabolism of glucose) and subsequently splitting oxaloacetate to oxalate and acetate by oxaloacetase enzyme, whereafter oxalate is converted to oxalyl-CoA and further to glyoxylate and glycolic acid. Acetate may enter the glyoxylate cycle and be converted to glycolic acid. The oxalate pathway includes a step for incorporation of $CO_2/HCO_3$—instead of producing $CO_2$.

In a specific embodiment of the invention the fungus has increased glycolic acid, oxalate, oxalyl-coA and/or glyoxylate production.

Glycolic acids are produced from carbon substrates. In one embodiment of the invention, one or several carbon substrates are selected from the group consisting of pentose such as xylose, xylan or other oligomer of xylose; hexose such as glucose, fructose, mannose or galactose and oligomers of glucose such as maltose, maltotriose, isomaltotriose, starch or cellulose; and sugars such a sugars derived from lignocellulose; oxalate; $CO_2$; ethanol; and any combination thereof. "Sugars derived from lignocellulose" refer to sugar monomers of lignocellulose including but not limited to glucose, xylose, fructose, mannose, galactose, rhamnose and arabinose. As used herein "derived from" refers to products obtained from or isolated from a starting product, as well as modifications thereof. In some embodiments the carbon substrate may comprise ethanol. In a very specific embodiment the production of glycolic acid is not achieved via ethanol.

The object of the present invention has been achieved by increasing oxalate-CoA ligase activity and/or oxalyl-CoA reductase activity and/or ketopantoate reductase activity.

Figure 1:
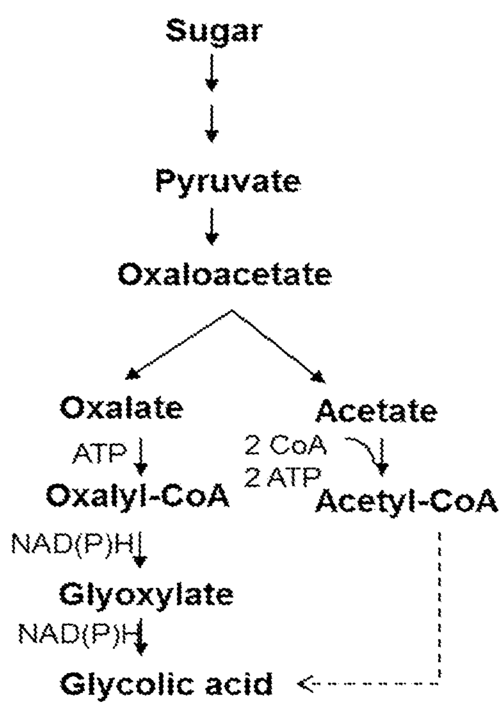
FIG. 1 shows an example of producing glycolic acid via oxalate pathway. In the oxalate pathway pyruvate or phosphoenol pyruvate is first carboxylated into oxaloacetate. Then oxaloacetate is split to oxalate and acetate, after which oxalate can be converted to oxalyl-CoA in an ATP dependent reaction, and oxalyl-coA is then reduced to glyoxylate and further to glycolic acid. Acetate can be converted to acetyl-CoA, which further enters a glyoxylate cycle and is converted to glycolic acid (or to other products). Alternatively and not shown in FIG. 1, oxaloacetate for the reaction of specific embodiment of the present invention may originate from pyruvate via the tricarboxylic acid cycle (TCA) cycle.

The genetic modification utilized in the present invention is used for modifying, more specifically increasing, enzyme activity associated with oxalyl-CoA. In one embodiment of the invention "an enzyme activity associated with oxalyl-CoA" refers to an enzyme activity of the oxalate pathway (see FIG. 1), which is able to convert oxalate to oxalyl-CoA or oxalyl-CoA to glyoxylate. In one embodiment of the invention the enzyme activity associated with oxalyl-CoA is oxalate-CoA ligase activity, oxalyl-CoA reductase activity or ketopantoate reductase activity, or any combination thereof (such as oxalate-CoA ligase and oxalyl-CoA reductase activities; oxalate-CoA ligase and ketopantoate reductase activities; oxalate-CoA ligase, oxalyl-CoA reductase and ketopantoate reductase activities). If more than one enzyme activities are targeted by genetic modifications both oxalate-CoA ligase activity and oxalyl-CoA reductase activity, or oxalate-CoA ligase activity and ketopantoate reductase activity may be increased. In one embodiment the fungus has been genetically modified to increase oxalate-CoA ligase activity and/or oxalyl-CoA reductase activity and/or ketopantoate reductase activity.

In one embodiment the engineered fungi of the present invention comprises a genetic modification for increasing the production of oxalyl-CoA and/or glyoxylate by increasing oxalate-CoA ligase activity and/or oxalyl-CoA reductase/ketopantoate reductase activity, respectively.

In one embodiment of the invention the fungus has increased glycolic acid, oxalyl-coA and/or glyoxylate production.

An engineered fungus of the present invention comprises a genetic modification increasing protein or enzyme activity. As used herein "increased protein or enzyme activity" refers to the presence of higher activity of a protein compared to a wild type protein, or higher total protein activity of a cell or fungus compared to an unmodified cell or fungus. Increased protein activity may result from up-regulation of the polypeptide expression, up-regulation of the gene expression, addition of at least part of a gene (including addition of gene copies or addition of a gene normally absent in said cell or fungus), increase of protein and/or increased activity of a protein. Specific examples of generating increased protein or enzyme activities are provided in the Example section.

Genetic modifications resulting in increased protein activity include but are not limited to genetic insertions, deletions or disruptions of one or more genes or a fragment(s) thereof or insertions, deletions, disruptions or substitutions of one or more nucleotides, or addition of plasmids. As used herein "disruption" refers to insertion of one or several nucleotides into the gene or polynucleotide sequence resulting in lack of the corresponding protein or presence of non-functional proteins or protein with lowered activity. As used herein "over-expression" refers to excessive expression of a gene or polynucleotide by producing more products (e.g. protein) than an unmodified fungus. For example one or more copies of a gene or genes may be transformed to a cell for overexpression. The term also encompasses embodiments, where a regulating region such as a promoter or promoter region has been modified or changed or a regulating region (e.g. a promoter) not naturally present in the fungus has been inserted to allow the over-expression of a gene. Also, epigenetic modifications such as reducing DNA methylation or histone modifications are included in "genetic modifications" resulting in increased protein activity or overexpression of a gene. As used herein "increased or up-regulated expression" refers to increased expression of the gene or polypeptide of interest compared to a wild type fungus without the genetic modification. Expression or increased expression can be proved for example by western, northern or southern blotting or quantitative PCR or any other suitable method known to a person skilled in the art.

The fungus of the invention may comprise one or several genetic modifications.

In one embodiment of the present invention the fungus comprises a genetic modification reducing protein or enzyme activity. "Reduced activity" refers to the presence of less activity, if any, in a specific protein or modified fungus compared to a wild type protein or fungus, respectively, or lower activity (if any) in a cell or fungus compared to an unmodified cell or fungus. Reduced activity may result from down regulation of the polypeptide expression, down regulation of the gene expression, lack of at least part of the gene, lack of protein and/or lowered activity of the protein. There are various genetic techniques for reducing the activity of a protein and said techniques are well-known to a person skilled in the art. These techniques make use of the nucleotide sequence of the gene or of the nucleotide sequence in the proximity of the gene.

In a specific embodiment of the invention one or more proteins are inactivated. As used herein "inactivation" refers to a situation wherein activity of a protein is totally inactivated i.e. a cell has no activity of a specific protein. The gene can be inactivated e.g. by preventing its expression or by mutation or deletion of the gene or part thereof. In one embodiment of the invention one or more genes or any fragment thereof has been deleted. In a specific embodiment the recombinant fungus has been genetically modified by deleting at least part of a gene. As used herein "part of a gene" refers to one or several nucleotides of the gene or any fragment thereof. For example gene knockout methods are suitable for deleting the nucleotide sequence that encodes a polypeptide having a specific activity, of any part thereof.

The knowledge of a polynucleotide sequence encoding a polypeptide can be used for genetically modifying a suitable fungus.

In one embodiment the fungus has been genetically modified to express or overexpress a gene encoding oxalate-CoA ligase and/or oxalyl-CoA reductase and/or ketopantoate reductase activity (e.g. oxalate-CoA ligase and oxalyl-CoA reductase; oxalate-CoA ligase and ketopantoate reductase; oxalate-CoA ligase, oxalyl-CoA reductase and ketopantoate reductase).

As used herein "oxalate-CoA ligase" refers to a protein having oxalate-CoA activity i.e. activity to convert oxalate to oxalyl-CoA. The oxalate-CoA ligase is classified as EC 6.2.1.8. The oxalate-CoA ligase refers to not only *Pichia kudriavzevii* oxalate-CoA ligase but also to any other oxalate-CoA ligase homologue from any microorganism, e.g. fungus. As an example, FAT2 proteins have oxalate-CoA ligase activity. The FAT2 protein and FAT2 gene of the *Saccharomyces cerevisiae* are identified in the articles of Blobel F and Erdmann R (1996, Eur J Biochem 240(2):468-76) and Foster J and Nakata P A (2014, FEBS Lett 588(1): 160-6). Examples of suitable open reading frames (ORF) include but are not limited to ORF of *S. cerevisiae* (PCS60, YBR222C).

As used herein "oxalyl-CoA reductase" refers to a protein having oxalate-CoA reductase activity i.e. activity to convert oxalyl-CoA to glyoxylate (i.e. glyoxylic acid). The oxalyl-CoA reductase is classified as EC 1.2.1.17. The oxalyl-CoA reductase refers to not only *Pichia kudriavzevii* oxalyl-CoA reductase (if there is such) but also to any other oxalyl-CoA reductase homologue from any micro-organism, e.g. fungus. *M. extorquens* panE2 gene is described for example in the article of Schneider at al. (2012, J Bact 194: 3144-3155). Examples of suitable open reading frames (ORF) include but are not limited to ORF of *M. extorquens* (WP_015822665). As used herein "oxalyl-CoA reductase" may also have ketopantoate reductase activity i.e. activity catalyzing the second step of the pantothenate pathway after ketoisovalerate. Thus, also ketopantoate reductases may harbor oxalyl-CoA reductase activity. The ketopantoate reductase is classified as EC 1.1.1.169. The ketopantoate reductase refers to not only *Pichia kudriavzevii* ketopantoate reductase but also to any other ketopantoate reductase homologue from any micro-organism, e.g. fungus. As an example, panE2 protein of the *Methylobacterium extorquens* is identified in the article of Schneider at al. (2012, J Bact 194: 3144-3155). As mentioned above *M. extorquens* panE2 gene is described for example in the article of Schneider at al. (2012, J Bact 194: 3144-3155). Examples of suitable open reading frames (ORF) include but are not limited to ORF of *M. extorquens* (WP_015822665).

In certain embodiments, the engineered fungus includes at least one (e.g. one, two, three, four, five, six or more) heterologous polynucleotide. Any of the inserted polynucleotides or genes (e.g. one, two, three, four, five, six or more) may be heterologous or homologous to the host fungus. The fungus can be genetically modified by transforming it with a heterologous nucleic acid that encodes a heterologous protein. Alternatively, for example heterologous promoters or other regulating sequences can be utilized in the fungus of the invention. As used herein "heterologous polynucleotide" refers to a polynucleotide not naturally occurring in the host fungus.

Herein, the terms "polypeptide" and "protein" are used interchangeably to refer to polymers of amino acids of any length. As used herein "an enzyme" refers to a protein or polypeptide which is able to accelerate or catalyze chemical reactions.

As used herein "polynucleotide" refers to any polynucleotide, such as single or double-stranded DNA (genomic DNA or cDNA) or RNA, comprising a nucleic acid sequence encoding a polypeptide in question or a conservative sequence variant thereof. Conservative nucleotide sequence variants (i.e. nucleotide sequence modifications, which do not significantly alter biological properties of the encoded polypeptide) include variants arising from the degeneration of the genetic code and from silent mutations.

In a specific embodiment the fungus that has been genetically modified to increase an enzyme activity associated with oxalyl-CoA (e.g. oxalate-CoA ligase activity and/or oxalyl-CoA reductase activity and/or ketopantoate reductase activity, or any combination thereof) has further been genetically modified to increase at least glyoxylate reductase (GLYR) activity, oxaloacetase activity, pyruvate carboxylase activity, carbonate dehydratase, isoprene synthase, isopentenyldiphosphate delta-isomerase, HMG-CoA reductase, fatty acid synthase and/or acetyl-CoA carboxylase activity, or any combination thereof (e.g. glyoxylate reductase and oxaloacetase activities; glyoxylate reductase and pyruvate carboxylase activities; glyoxylate reductase and carbonate dehydratase activities; glyoxylate reductase and isoprene synthase activities; glyoxylate reductase and isopentenyldiphosphate delta-isomerase activities; glyoxylate reductase and HMG-CoA reductase activities; glyoxylate reductase and fatty acid synthase activities; glyoxylate reductase and acetyl-CoA carboxylase activities;

oxaloacetase and pyruvate carboxylase activities; oxaloacetase and carbonate dehydratase activities; oxaloacetase and isoprene synthase activities; oxaloacetase and isopentenyldiphosphate delta-isomerase activities; oxaloacetase and HMG-CoA reductase activities; oxaloacetase and fatty acid synthase activities; oxaloacetase and acetyl-CoA carboxylase activities;

pyruvate carboxylase and carbonate dehydratase activities; pyruvate carboxylase and isoprene synthase activities; pyruvate carboxylase and isopentenyldiphosphate delta-isomerase activities; pyruvate carboxylase and HMG-CoA reductase activities; pyruvate carboxylase and fatty acid synthase activities; pyruvate carboxylase and acetyl-CoA carboxylase activities;

carbonate dehydratase activities and isoprene synthase activities; carbonate dehydratase activities and isopentenyldiphosphate delta-isomerase activities; carbonate dehydratase activities and HMG-CoA reductase activities; carbonate dehydratase activities and fatty acid synthase activities; carbonate dehydratase activities and acetyl-CoA carboxylase activities;

isoprene synthase activities and isopentenyldiphosphate delta-isomerase activities; isoprene synthase activities and HMG-CoA reductase activities; isoprene synthase activities and fatty acid synthase activities; isoprene synthase activities and acetyl-CoA carboxylase activities;

isopentenyldiphosphate delta-isomerase activities and fatty acid synthase activities; isopentenyldiphosphate delta-isomerase activities and acetyl-CoA carboxylase activities; isopentenyldiphosphate delta-isomerase activities and HMG-CoA reductase activities;

fatty acid synthase activities and acetyl-CoA carboxylase activities; fatty acid synthase activities and HMG-CoA reductase activities;

acetyl-CoA carboxylase activities and HMG-CoA reductase activities;

glyoxylate reductase activity, oxaloacetase activity, pyruvate carboxylase activity and carbonate dehydratase activity;

isoprene synthase activity, isopentenyldiphosphate delta-isomerase activity, oxaloacetase activity, HMG-CoA reductase activity, pyruvate carboxylase activity and glyoxylate reductase activity;

acetyl-CoA carboxylase activity and fatty acid synthase activity;

glyoxylate reductase activity, oxaloacetase activity, pyruvate carboxylate activity, carbonate dehydratase activity, acetyl-CoA carboxylase activity and fatty acid synthase activity);

isoprene synthase activity, isopentenyldiphosphate delta-isomerase activity, oxaloacetase activity, HMG-CoA reductase activity, pyruvate carboxylase activity, carbonate dehydratase activity and glyoxylate reductase activity;

glyoxylate reductase activity, oxaloacetase activity, pyruvate carboxylate activity, acetyl-CoA carboxylase activity and fatty acid synthase activity).

In a very specific embodiment the fungus has been genetically modified to express or overexpress a gene encoding glyoxylate reductase, oxaloacetase, pyruvate carboxylase, carbonate dehydratase, isoprene synthase, isopentenyldiphosphate delta-isomerase, fatty acid synthase or acetyl-CoA carboxylase, or any combination thereof (see some of the possible combinations in the above chapter).

As used herein "glyoxylate reductase" refers to a protein having glyoxylate reductase activity i.e. activity to convert glyoxylate to glycolic acid. The glyoxylate reductase is classified as EC 1.1.1.79 or 1.1.126. The glyoxylate reductase refers to not only *Pichia kudriavzevii* glyoxylate reductase but also to any other glyoxylate reductase homologue from any organism, e.g. fungus or plant (such as *Arabidopsis thaliana, Peptinophilus, Limnochorda* or *Desulfovibrio*). As an example, Glyr1 protein (EC 1.1.1.79) of the *Arabidopsis thaliana* is identified in the article of Hoover G J et al. (2007, Can J Bot. 85 (9): 883-895). GLYR1 gene is described for example in the article of Salanoubat et al (2000, Nature 408, 820-822). Examples of suitable open reading frames (ORF) include but are not limited to ORF of *Arabidopsis thaliana* (GenBank AY044183).

As used herein "oxaloacetase" refers to a protein having oxaloacetase activity i.e. activity to convert oxaloacetate to oxalate. The oxaloacetase is classified as EC 3.7.1.1. The oxaloacetase refers to not only *Pichia kudriavzevii* oxaloacetase (if there is such) but also to any other oxaloacetase homologue from any micro-organism, e.g. fungus (such as *Aspergillus niger, Cyphonectria parasitica, Botryotinia fuckeliana* or *Penicillium chrysogenum*). As an example, OAH protein of the *Aspergillus niger* is identified in the article of Kobayashi K et al (2014, J Ind Microbiol Biotechnol 41, 749-756). OAH gene is described for example in the article of GomBert A K et al. (2011, Fungal Genetics and Biology 48, 831-839. Examples of suitable open reading frames (ORF) include but are not limited to ORF of *Penicillium chrysogenum* (Pc22g24830).

As used herein "pyruvate carboxylase" (PYC) refers to a protein having pyruvate carboxylase activity i.e. activity to convert pyruvate to oxaloacetate. The pyruvate carboxylase is classified as EC 6.4.1.1. The pyruvate carboxylase refers to not only *Pichia kudriavzevii* pyruvate carboxylase but also to any other pyruvate carboxylase homologue from any micro-organism, e.g. fungus (such as *Saccharomyces cerevisiae*). As an example, PYC1 and PYC2 proteins of the *Saccharomyces cerevisiae* are identified in the article of Brewster N K, et al. (1994 Arch Biochem Biophys 311(1): 62-71). PYC1 and PYC2 genes are described for example in the article of Walker M E, et al. (1991, Biochem Biophys Res Commun 176(3):1210-7). Examples of suitable open reading frames (ORF) include but are not limited to ORF of *Saccharomyces cerevisiae* (PYC2, YBR218C).

As used herein "carbonate dehydratase" refers to a protein having carbonate dehydratase activity i.e. activity to convert $CO_2$ to bicarbonate. The carbonate dehydratase is classified as EC 4.2.1.1. The carbonate dehydratase refers to not only *Pichia kudriavzevii* carbonate dehydratase but also to any other carbonate dehydratase homologue from any micro-organism, e.g. fungus (such as *Saccharomyces cerevisiae*). As an example, NCE103 protein of the *Saccharomyces cerevisiae* is identified in the article of Gabriele Amoroso et al. (2005, Molecular Microbiology 56(2), 549-558). NCE103 gene is described for example in the article of Aguilera J. et al. (2005, FEMS Yeast Res 5, 579-593). Examples of suitable open reading frames (ORF) include but are not limited to ORF of *Saccharomyces cerevisiae* (YNL036w).

As used herein "isoprene synthase" refers to a protein having isoprene synthase activity i.e. activity to convert dimethylallyl diphosphate to isoprene. The isoprene synthase is classified as EC 4.2.3.27. The isoprene synthase refers to not only *Pichia kudriavzevii* carbonate dehydratase but also to any other isoprene synthase homologue from any organism, e.g. green plant (such as *Ipomoea batatas*). As an example, IspS protein of *Ipomoea batatas* is identified in the article of Ilmén M et al (2015, Metab Eng 31, 153-162). IspS gene of *Ipomoea batatas* is identified in the article of Ilmén Metal (2015, Metab Eng 31, 153-162). Examples of suitable reading frames (ORF) include but are not limited to ORF of *Ipomoea batatas* (JP105673.1). In a very specific embodiment of the present invention isoprene is co-produced (or produced) with glycolic acid.

As used herein "isopentenyl diphosphate:dimethylallyl diphosphate isomerase" also known as "isopentenyl pyrophosphate isomerase" or "isopentenyl-diphosphate delta isomerase" (IDI) refers to a protein catalyzing the isomerization between isopentenyl pyrophosphate (IPP) and dimethylallyl pyrophosphate (DMAPP). The isomerization reaction is part of the biosynthesis of isoprenoids and the sterol precursor squalene. The isopentenyl diphosphate:dimethylallyl diphosphate isomerase is classified as EC 5.3.3.2. The isopentenyl diphosphate:dimethylallyl diphosphate isomerase refers to not only *Pichia kudriavzevii* isopentenyl diphosphate:dimethylallyl diphosphate isomerase but also to any other isopentenyl diphosphate:dimethylallyl diphosphate isomerase homologue from any organism, e.g. fungus (such as *Saccharomyces cerevisiae*). As an example, IDI1 protein of the *Saccharomyces cerevisiae* are identified in the article of Anderson M S, et al. (1989, J Biol Chem 264(32), 19169-19175). IDI1 gene is described for example in the article of Mayer M P, et al. (1992, Yeast 8(9), 743-748). Examples of suitable open reading frames (ORF) include but are not limited to ORF of *Saccharomyces cerevisiae* (IDI1, YPL117C).

As used herein "HMG-CoA reductase" (HMG) refers to a protein having hydroxymethylglutaryl-CoA reductase activity i.e. activity to convert hydroxymethylglutaryl-CoA (HMG-CoA) to mevalonate. The HMG-CoA reductase is classified as EC 1.1.1.34. The HMG-CoA reductase refers to not only *Pichia kudriavzevii* HMG-CoA reductase but also to any other pyruvate carboxylase homologue from any microorganism, e.g. fungus (such as *Saccharomyces cerevisiae*). As an example, a truncated HMG1 protein (i.e. lacking amino acids 1-552), of the *Saccharomyces cerevisiae* is identified in the article of Polakowski T. et al (1998, Appl Microbiol Biotechnol 49(1):66-71. HMG1 and HMG2 genes are described for example in the article of Basson M E, et al. (1986, Proc Natl Acad Sci USA 83(15):5563-5567). Examples of suitable open reading frames (ORF) include but are not limited to ORF of *Saccharomyces cerevisiae* (HMG1, YML075C).

As used herein "acetyl-CoA carboxylase" refers to a protein having carboxylating activity i.e. activity to convert acetyl-CoA and $CO_2$ to malonyl-CoA. The acetyl-CoA carboxylase is classified as EC 6.4.1.2. The acetyl-CoA carboxylase refers to not only *Pichia kudriavzevii* acetyl-CoA carboxylase but also to any other acetyl-CoA carboxylase homologue from any micro-organism, e.g. fungus (such as *Saccharomyces cerevisiae*). As an example, ACC1 protein of the *Saccharomyces cerevisiae* is identified in the article of M. Mishina et al. (1980, Eur J Biochem 111(1):79-87). ACC1 gene is described for example in the article of Runguphan and Keasling (2014, Metab Eng. 21:103-13). Examples of suitable open reading frames (ORF) include but are not limited to ORF of *Saccharomyces cerevisiae* (YNR016C).

As used herein "fatty acid synthase" refers to a protein that catalyses fatty acid synthesis. The fatty acid synthase is classified as EC 2.3.1.85. The fatty acid synthase refers to not only *Pichia kudriavzevii* fatty acid synthase but also to any other fatty acid synthase homologue from any micro-organism, e.g. fungus (such as *Saccharomyces cerevisiae*). As an example, FAS1 protein of the *Saccharomyces cerevisiae* is identified in the article of M. Schweizer et al. (1986, Mol Gen Genet 203(3):479-86). FAS1 and FAS2 genes are described for example in the article of Runguphan and Keasling (2014, Metab Eng. 21:103-13). Examples of suitable open reading frames (ORF) include but are not limited to ORF of *Saccharomyces cerevisiae* (YKL182W and YPL231W).

In one embodiment the fungus expresses the oxalate pathway. In a very specific embodiment of the invention the biotechnological route for producing glycolic acid by fermentation from pyruvate comprises at least five proteins selected from the group consisting of oxalate-CoA ligase, oxalyl-CoA reductase/ketopantoate reductase, glyoxylate reductase, oxaloacetase, pyruvate carboxylase and carbonate dehydratase (e.g. the combination of oxalate-CoA ligase, oxalyl-CoA reductase/ketopantoate reductase, glyoxylate reductase, oxaloacetase and pyruvate carboxylase). One or more of said proteins may be heterologous, i.e. do not naturally occur in the host fungus. The genetically modified fungus may be prepared e.g. by allowing at least one or more polynucleotides encoding oxalate-CoA ligase, oxalyl-CoA reductase and/or ketopantoate reductase to be expressed in a fungus (e.g. by inserting one or more encoding polynucleotides in question to said fungus or by modifying the regulation sequence of said encoding polynucleotide).

In addition to a modification of at least one or more genes selected from the group consisting of a gene encoding oxalate-CoA ligase, oxalyl-CoA reductase and ketopantoate reductase or any combination thereof, a fungus of the present invention may also comprise one or several genetic modifications in one or several other genes. These genetic modifications include any genetic modifications including but not limited to genetic insertions, deletions or disruptions of one or more genes or a fragment(s) thereof or insertions, deletions, disruptions or substitutions of one or more nucleotides, or addition of plasmids. As used herein "disruption" refers to insertion of one or several nucleotides into the gene or polynucleotide sequence resulting in lack of the corresponding protein or presence of non-functional proteins or protein with lowered activity. Other genetic modifications may be selected from one or several modifications causing down regulation and/or over-expression of a gene or not affecting the expression of a gene.

In a further embodiment the fungus comprises a genetic modification of one or more genes selected from the group consisting of malate synthase MLS (such as MLS1), pyruvate decarboxylase PDC (such as PDC1), glycerol-3-phosphate dehydrogenase GPD (such as GPD1), IDP (such as IDP1) and any combination thereof (i.e. MLS and PDC; MLS, PDC and GPD; PDC and GPD; MLS and GPD), or further comprises a genetic modification of a promoter (e.g. change of a promoter). In a very specific embodiment the fungus has been genetically modified by deleting at least part of a gene or by inactivating a gene selected from the group consisting of MLS (such as MLS1), PDC (such as PDC1), GPD (such as GPD1), IDP (such as IDP1), and any combination thereof (i.e. MLS and PDC; MLS, PDC and GPD; MLS, PDC, GPD and IDP; PDC and GPD; PDC, GPD and IDP; MLS and GPD; MLS, GPD and IDP; MLS and IDP; MLS, PDC and IDP; PDC and IDP; GPD and IDP). Reduced expression of MLS (e.g. MLS1) results in avoiding conversion of glyoxylate to malate. Reduced expression of PDC (e.g. PDC1) results in avoiding ethanol formation. Reduced expression of GPD (e.g. GPD1) results in avoiding glycerol formation. These strains may provide the most efficient way for producing oxalate, oxalyl-CoA, glyoxylate and/or glycolic acid.

In a specific embodiment the non-modified fungus (i.e. fungus prior to genetic modification of the present invention) comprises one, two, three or more copies of MLS, PDC, GDP and/or IDP genes. In such cases one, two, three or more copies of said genes may have been genetically modified.

As used herein MLS gene refers to a gene encoding a malate synthase, an enzyme of the glyoxylate cycle. The malate synthase is classified as EC 2.3.3.9. All isozymes, isoforms and variants are included with the scope of MLS.

As used herein PDC gene refers to a gene encoding a pyruvate decarboxylase, which catalyzes the degradation of pyruvate into acetaldehyde and carbon dioxide. PDC1, PDC5, and PDC6 encode three different isozymes of pyruvate decarboxylase. The pyruvate decarboxylase is classified as EC 4.1.1.1. All isozymes, isoforms and variants are included with the scope of PDC.

As used herein GPD gene refers to a gene encoding NAD-dependent glycerol-3-phosphate dehydrogenase, which is a key enzyme of glycerol biosynthesis catalyzing the reaction of dihydroxyacetone phosphate to glycerol-3-phosphate. Two unlinked genes, GPD1 and GPD2 encode related but not identical polypeptides. The NAD-dependent glycerol-3-phosphate dehydrogenase is classified as EC 1.1.1.8. All isozymes, isoforms and variants are included with the scope of GPD.

As used herein IDP gene refers to a gene encoding either cytosolic (IDP2) or mitochondrial (IDP1) NADP-specific isocitrate dehydrogenase, which catalyzes the oxidation of isocitrate to alpha-ketoglutarate. The isocitrate dehydrogenase is classified as EC 1.1.1.42. All isozymes, isoforms and variants are included with the scope of IDP.

The fungus of the present invention may also contain other genetic modifications than those specifically described herein.

Methods for making any genetic modifications are generally well known and are described in various practical manuals describing laboratory molecular techniques. The construction of a microorganism in which one or more genes are genetically modified is within the skills of an artisan. Some examples of the general procedure and specific embodiments are described in the Examples chapter.

The presence, absence or amount of protein activities in a cell or fungus can be detected by any suitable method known in the art. Non-limiting examples of suitable detection methods include enzymatic assays, PCR based assays (e.g., qPCR, RTPCR), immunological detection methods (e.g., antibodies specific for said proteins) and combinations thereof.

In one embodiment of the invention the isoprene pathway, triacylglyceride (TAG) pathway, lipid pathway and/or any pathway starting from acetate/acetyl-CoA is present in said fungus. As used herein "isoprene pathway" relates to a pathway wherein acetyl-CoA produced from acetate is converted to isoprene. As used herein "TAG pathway" relates to a pathway wherein acetyl-CoA is converted to triacylglyceride. Triacylglyceride is an ester derived from glycerol and three fatty acids. As used herein "lipid pathway" relates to a lipid metabolism pathway including but not limited to lipid biosynthesis and degradation (e.g. de novo synthesis, uptake of external lipids, and turnover of lipids). As an example, acetyl-CoA derived from citrate degradation or from acetate is carboxylated to form malonyl-CoA which serves as a two carbon building block in the following FA synthesis reactions. Lipids are categorized into eight classes which are fatty acids (FA), glycerolipids, glycerophospholipids, sterols and sterol derivatives, sphingolipids, prenol lipids, glycolipids, and polyketides. As used herein "any pathway starting from acetate/acetyl-CoA" includes but is not limited to isoprene pathway, TAG pathway, lipid pathway, terpene/terpenoid pathway, polyketide pathway, malonic acid pathway, acetoin pathway, acetone pathway, amino acid pathway, n-butanol pathway, fatty acid ethyl ester pathway, alkane pathway, polyhydroxyalkanoate pathway, pathways via TCA cycle intermediates.

An engineered microorganism utilized in the present invention is a fungus. "Fungi" "fungus" and "fungal" as used herein refer to yeast and filamentous fungi (i.e. moulds). In one embodiment of the invention the fungus is a yeast or filamentous fungus.

A microorganism selected for the present invention is suitable for genetic manipulation and often can be cultured at cell densities useful for industrial production of a target product. A microorganism selected may be maintained in a fermentation device.

The genetically modified fungi of the invention are obtained by performing specific genetic modifications. As used herein, a "recombinant fungi" refers to any fungi that has been genetically modified to contain different genetic material compared to the fungi before modification (e.g. comprise a deletion, substitution, disruption or insertion of one or more nucleic acids including an entire gene(s) or parts thereof compared to the fungi before modification). "The recombinant fungi" also refers to a host cell comprising said genetic modification.

In a specific embodiment of the invention the fungus is a yeast selected from the genera *Arxula, Cryptococcus, Candida, Debaryomyces, Galactomyces, Hansenula, Kazachstania, Kluyveromyces, Lipomyces, Lodderomyces, Metschnikowia, Millerozyma, Priceomyces, Rhodosporidium, Rhodotorula, Saccharomyces, Sugiyamaella, Trichosporon, Pichia* and *Yarrowia* and *Zygosaccharomyces*, specifically from the group consisting of *Arxula adeninivorans, Candida* sp., *Candida catenulata, Candida glycerinogenes, Candida haemulonii, Candida humilis Candida maltosa, Candida parapsilopsis, Candida rhagii, Candida rugosa, Candida sake, Candida tenuis Cryptococcus curvatus, Cryptococcus albidus, Debaryomyces hansenii, Debaryomyces robertsiae, Galactomyces geotrichum, Hansenula ciferri, Kazachstania exigua, Klyuveromyces lactis, Kluyveromyces marxianus, Lipomyces lipofer, Lipomyces* ssp., *Lipomyces starkeyi, Lipomyces tetrasporus, Lodderomyces elongisporus, Metchnikowia pulcherrima, Metschnikowia reukaufii, Millerozyma farinosa, Priceomyces haplophilus, Rhodosporidium toruloides, Rhodotorula glutinis, Rhodotorula gracilis, Saccharomyces cerevisiae, Sugiyamaeiia smithiae, Trichosporon pullulans, Trichosporon veenhuisii, Pichia jadinii, Pichia fermentans, Pichia membranifaciens, Pichia guilliermondii, Pichia kudriavzevii, Pichia stipitis*, and *Yarrowia lipolytica*, and *Zygosaccharomyces lentus* or a filamentous fungus selected from the genera *Aspergillus, Cunninghamella, Fusarium, Glomus, Humicola, Mortierella, Mucor, Penicillium, Pythium* and *Rhizopus*, specifically from the group consisting of *Aspergillus nidulans, Aspergillus oryzae, Aspergillus terreus, Aspergillus niger, Cuninghamella blakesleeana, Cuninghamella japonica, Fusarium moniliforme, Fusarium oxysporum, Glomus caledonius, Humicola lanuginose, Mortierella isabellina, Mortierella pusilla, Mortierella vinacea, Mucor circinelloides, Mucor plumbeus, Mucor ramanniana, Penicillium frequentans, Penicillium lilacinum, Penicillium soppii, Penicillium spinulosum, Pythium ultimum* and *Rhizopus oryzae*, and *Trichoderma reesei*.

In a more specific embodiment the yeast is *Pichia kudriavzevii*.

In one specific embodiment of the invention the recombinant fungus is able to produce ethanol. In another embodiment the fungus is not able to produce ethanol. In a very specific embodiment production of oxalate, oxalyl-coA, glyoxylate and/or glycolic acid is achieved directly from glucose and not via ethanol.

In one embodiment the genetically modified fungus is acid tolerant.

The genetically modified or recombinant fungi are cultured in conditions allowing the expression of oxalate-CoA ligase and/or oxalyl-CoA reductase and/or ketopantoate reductase. The methods of the present invention are carried out under culture conditions in which the cultured microorganisms produce oxalate, oxalyl-coA, glyoxylate and/or glycolic acid. The glycolic acid production capacity of the genetically modified fungal hosts may be examined by cultivation under conditions appropriate for glycolic acid production. The genetically modified fungi of the present invention are capable of producing increased levels of glycolic acids. The increase may be at least a 1.5, 2, 3, 4, 5, 10, 15, 20, 30, 50, 100, 500 or 1000 fold increase in glycolic acid concentration in genetically modified fungus of the present invention compared to an unmodified fungus or any fungus with other modifications during cultivation. Alternatively, it may be at least a 1.5, 2, 3, 4, 5, 10, 15, 20, 30, 50, 100, 500 or 1000 fold increase in glycolic acid yield per used carbon source compared to an unmodified fungus or any fungus with other modifications. Said increase may also refer to at least a 1.5, 2, 3, 4, 5, 10, 15, 20, 30, 50, 100, 500 or 1000 fold increase in glycolic acid production rate (mg/I/h) compared to an unmodified fungal strain or any fungus with other modifications. This increase of glycolic acid production may be detected either intracellularly or in the amount of glycolic acids in culture medium.

The genetically modified fungi are cultivated in a medium containing appropriate carbon sources together with other optional ingredients selected from the group consisting of nitrogen or a source of nitrogen (such as amino acids, proteins, inorganic nitrogen sources such as ammonia or ammonium salts), yeast extract, peptone, minerals and vitamins.

Suitable cultivation conditions, such as temperature, cell density, selection of nutrients, and the like are within the knowledge of a skilled person and can be selected to provide an economical process with the micro-organism in question. Temperatures during each of the growth phase and the production phase may range from above the freezing temperature of the medium to about 50° C., although the optimal temperature will depend somewhat on the particular microorganism. In a specific embodiment the temperature, particularly during the production phase, is from about 25 to 30° C.

The pH of the cultivation process may or may not be controlled to remain at a constant pH, but is usually between 3 and 9, depending on the production organism. Optimally the pH is controlled to a constant pH of 5-8. The present invention may also be implemented at a very low pH, even as low as 1.5. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like. In general, those buffering agents that have been used in conventional cultivation methods are also suitable here.

The cultivation is conveniently conducted aerobically or microaerobically. If desired, specific oxygen uptake rate can be used as a process control. The process of the invention can be conducted continuously, batch-wise, or some combination thereof.

In one embodiment the method further comprises recovering the resulting glycolic acid from the medium. The cells producing glycolic acids do not need to be disrupted. In one embodiment glycolic acid may be recovered from the fermentation medium by e.g. ion exchange chromatography or reactive extraction. In some embodiments glycolic acid may be polymerized in the medium and recovered thereafter.

In one embodiment the method further comprises recovering the resulting oxalate, oxalyl-coA and/or glyoxylate from the medium or from the cells. In some embodiments the cells producing oxalate, oxalyl-coA and/or glyoxylate have to be disrupted.

In one embodiment the production method of the present invention further comprises isolating and/or purifying oxalate, oxalyl-coA, glyoxylate and/or glycolic acid. Oxalate, oxalyl-coA, glyoxylate and/or glycolic acid may be isolated and purified (for example from the medium) by using any conventional methods known in the art such as ion exchange chromatography, reactive extraction, two phase extraction, molecular distillation, melt crystallization, hexane extraction, $CO_2$ extraction or distillation.

Glycolic acids are used for producing bio-based chemicals. Glycolic acid produced and recovered by the present invention may be utilized for producing e.g. one or several products selected from the group consisting of polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, and pharmaceuticals. Uses and methods for producing said products are well known to a person skilled in the art.

As an example glycolic acid may be polymerized to polyglycolic acid, which has high gas barrier properties and mechanical strength and furthermore it is biodegradable. For example glycolic acid based plastics or films offer unique properties. Also glycolic acid may also be used as a copolymer with other chemical agents such as lactic acid.

It will be obvious to a person skilled in the art that, as the technology advances, the inventive concept can be implemented in various ways. The invention and its embodiments are not limited to the examples described below but may vary within the scope of the claims.

EXAMPLES

Example 1. Construction of Glycolic Acid Producing *P. kudriavzevii* Strains

*P. kudriavzevii* strain H4155 overexpressing *A. thaliana* GLYR1 has been described earlier (Koivistoinen et al. WO 2013/050659). H4155 has both copies of diploid *P. kudriavzevii* MLS1 genes replaced by *A. thaliana* GLYR1. The transformation marker genes hph and MEL5, located between loxP sites, were removed from the genome of H4155 by transforming H4155 with the Cre recombinase expression plasmid pKLNatCre+loPGK resulting in a markerless strain H4738.

For overexpression of oxaloacetase *Penicillium chrysogenum* oah (Pc22g24830), was synthesized and codon optimized for expression in *S. cerevisiae*. The oxaloacetase expression vector pMIPk117 (SEQ ID NO: 3) consists of *P. kudriavzevii* PDC1 3' homology region—MEL5 marker cassette flanked by loxP sites—*P. kudriavzevii* TDH1 promoter—*Penicillium chrysogenum.oah*—*S. cerevisiae* PGK1 terminator—*P. kudriavzevii* PDC1 5' homology region. pMIPk117 (SEQ ID NO: 3) was digested with NotI and transformed into *P. kudriavzevii* H4738 using the lithium acetate method. The transformants were selected based on blue colour on yeast peptone dextrose (YPD) medium containing 5-bromo-4-chloro-3-indolyl-α-D-galactopyranoside (X-alpha-gal). The presence of the transforming DNA in the transformant yLIF-050 was confirmed by PCR.

For overexpression of pyruvate carboxylase, *S. cerevisiae* PYC2 was PCR amplified from genomic DNA of *S. cerevisiae* with the primers LIF108 (CCTCCACTAGTGGTCTCAGATCTAGAATGAGCAGTAGCAAGAAATTGGC (SEQ ID NO: 1)) and LIF109 (TCCAAAGCTTGGTCTCAGATCTTACTTTTTTTGGGATGGGGG (SEQ ID NO: 2)), the fragment was digested with BsaI and ligated with the 7094 bp BglII fragment of pMLV132B (SEQ ID NO: 4). The resulting construct pMIPk118 (SEQ ID NO: 5) consists of *P. kudriavzevii* PDC1 5' homology region—*P. kudriavzevii* PGK1 promoter—*S. cerevisiae* PYC2—*S. cerevisiae* ADH1 terminator—hygromycin resistance cassette flanked by loxP sites—*P. kudriavzevii* PDC1 3' homology region. pMIPk118 (SEQ ID NO: 5) was digested with NotI and transformed into *P. kudriavzevii* yLIF-050 using the lithium acetate method. The transformants were selected on yeast peptone dextrose (YPD) medium containing 500 μg/ml hygromycin. The presence of the transforming DNA in the transformant yLIF-065 was confirmed by PCR.

The MEL5 and hygromycin resistance markers were excised from yLIF-065 using the Cre-loxP system. The Cre recombinase was expressed from plasmid pKLNatCre+loPGK. The transformant yLIF-065 was retransformed with a modified plasmid pKINatCre Steensma and Ter Linde (2001, Yeast 18:469-472), expressing the Cre recombinase. To enhance the recombinase activity in *P. kudriavzevii* the *S. cerevisiae* GAL1 promoter in pKINatCre was replaced with *P. kudriavzevii* PGK1 promoter as described in (WO14162063A1). The transformants were selected on yeast peptone dextrose (YPD) medium containing 200 μg/ml nourseothricin. The markerless transformant yLIF-164 was isolated.

For simultaneous overexpression of oxalate-CoA ligase and oxalyl-CoA reductase the vector pMLV209 (SEQ ID NO: 6) was constructed using yeast recombination. pMLV209 (SEQ ID NO: 6) consists of *P. kudriavzevii* GPD1 3' homology region—hygromycin resistance cassette flanked by loxP sites—*P. kudriavzevii* PYK1 promoter—*S. cerevisiae* FAT2—*S. cerevisiae* PDC1 terminator *P. kudriavzevii* TEF1 promoter—*M. extorquens* panE2—*S. cerevisiae* FBA1 terminator—*P. kudriavzevii* GPD1 5' homology region. pMLV209 (SEQ ID NO: 6) was digested with NotI and transformed into *P. kudriavzevii* yLIF-164 using the lithium acetate method. The transformants were selected on yeast peptone dextrose (YPD) medium containing 500 μg/ml hygromycin. The presence of the transforming DNA in the transformant yLIF-270 was confirmed by PCR.

For replacement of *P. chrysosporium* oah gene by *A. niger* oah gene (Q7Z986), yLIF_270 was transformed with pMIPk114 (SEQ ID NO: 7) resulting in strain yLIF309. pMIPk114 (SEQ ID NO: 7) consists of *P. kudriavzevii* PDC1 3' homology region, MEL5 marker flanked by loxP sites—*P. kudriavzevii* TDH1 promoter—*A. niger oah*—*S. cerevisiae* PGK1 terminator. pMIPk114 (SEQ ID NO: 7) was digested with NotI and transformed into *P. kudriavzevii* yLIF-270 using the lithium acetate method. The transformants were selected based on blue colour on yeast peptone dextrose (YPD) medium containing 5-bromo-4-chloro-3-indolyl-α-D-galactopyranoside (X-alpha-gal).

The MEL5 and hygromycin resistance markers is excised from yLIF309 using the Cre-loxP system as described above. For overexpression of carbonate dehydratase the markerless derivative of yLIF309 is transformed with NotI digested pMIPk120 (SEQ ID NO: 8). pMIPk120 (SEQ ID NO: 8) consists of *P. kudriavzevii* PDC1 5' homology region—*P. kudriavzevii* PGK1 promoter—*S. cerevisiae* PYC2 —*S. cerevisiae* ADH1 terminator—*P. kudriavzevii* FBA1 promoter—*S. cerevisiae* NCE103 *S. cerevisiae* TDH1 terminator—hygromycin resistance cassette flanked by loxP sites—*P. kudriavzevii* PDC1 3' homology region. pMIPk120 (SEQ ID NO: 8) is digested with NotI and transformed into the markerless derivative of *P. kudriavzevii* yLIF309 using the lithium acetate method. The transformants are selected on yeast peptone dextrose (YPD) medium containing 500 μg/ml hygromycin. The presence of the transforming DNA in the transformants is confirmed by PCR.

Example 2. Production of Glycolic Acid in pH 5

*Pichia kudriavzevii* strain yLIF309 was cultured in Multifors bioreactors (max. working volume 500 ml, Infors HT, Switzerland) at pH 5, 30° C., 0.7 volume air [volume culture]−1 min−1 (vvm) and 900 rpm-1050 rpm agitation with 2 marine impellors. pH was maintained constant by addition of 2 M NaOH or 1 M $H_2PO_4$. Clerol antifoaming agent (Cognis, France, 0.2 ml l−1) was added to prevent foam formation. Minimal media (Verduyn with additional $KH_2PO_4$, $MgSO_4$ and $(NH_4)_2SO_4$) was used. The culture was first in a batch mode (starting volume 200 ml, 50 g/l glucose), after which the feed (200 g/l glucose) was started and culture continued in a fed-batch mode. Biomass was measured as optical density (OD) at 600 nm (OD600) or as dry weight. For dry weight, samples were collected in 2 ml pre-dried, pre-weighed microcentrifuge tubes, washed twice with equal volume distilled water and dried at 100° C. For determination of extracellular compounds (oxalate, glycolic acid, ethanol, glycerol, pyruvate, acetate, and D-glucose) HPLC using a Fast Acid Analysis Column (100 mm×7.8 mm, BioRad Laboratories, Hercules, Calif.) linked to an Aminex HPX-87H column (BioRad Labs, USA) with 2.5 mM H2504 as eluent and a flow rate of 0.5 ml min−1 was used. The column was maintained at 55° C. Peaks were detected using a Waters 410 differential refractometer and a Waters 2487 dual wavelength UV (210 nm) detector.

At the end of the culture 13 g/l glycolic acid (FIG. 2) was detected in the culture supernatant.

Control strain *Pichia kudriavzevii* strain yLIF164 was cultured in Multifors bioreactors (max. working volume 500 ml, Infors HT, Switzerland) at pH 5, 30° C., Gasflow 1 vvm (100% $CO_2$ flow and air flow mixed together to have total of 10% $CO_2$ in the mixture going to reactors) and 700 rpm-900 rpm agitation with 2 rushton impellors. pH was maintained constant by addition of 5 M KOH or 2 M $H_2PO_4$. Clerol antifoaming agent (Cognis, France, 0.5 ml 1-1) was added to prevent foam formation. Minimal media (Verduyn with additional $KH_2PO_4$, $MgSO_4$ and $(NH_4)_2SO_4$) was used. The culture was run in a batch mode (volume 400 ml, 100 g/l glucose). Biomass was measured as optical density (OD) at 600 nm (OD600) or as dry weight. For dry weight, samples were collected in 2 ml pre-dried, pre-weighed microcentrifuge tubes, washed twice with equal volume distilled water and dried at 100° C. For determination of extracellular compounds (oxalate, glycolic acid, ethanol, glycerol, pyruvate, acetate, and D-glucose) HPLC using a Fast Acid Analysis Column (100 mm×7.8 mm, BioRad Laboratories, Hercules, Calif.) linked to an Aminex HPX-87H column (BioRad Labs, USA) with 2.5 mM H2504 as eluent and a flow rate of 0.5 ml min-1 was used. The column was maintained at 55° C. Peaks were detected using a Waters 410 differential refractometer and a Waters 2487 dual wavelength UV (210 nm) detector.

At the end of the culture glycolic acid (FIG. 3) was not detected in the culture supernatant.

Example 3. Production of Glycolic Acid in Low pH

The *Pichia kudriavzevii* strain yLIF309 is cultured in minimal and/or rich media in culture conditions where final pH is lower than 3.5. The glycolic acid produced in the culture supernatant is measured as described in example 2.

Example 4. Co-Production of Glycolic Acid and Isoprene

Construction of isoprene producing *P. kudriavzevii* has been described in WO16018036A1. The isoprene producing strain overexpresses the heterologous *Ipomoea batatas* isoprene synthase IspS, and *S. cerevisiae* isopentenyl-diphosphate delta-isomerase (IDI1). The isoprene producing transformant Pk/IspS+IDI1-72 (WO16018036A1) was retransformed with a modified plasmid pKINatCre, expressing the Cre recombinase as described above and the markerless transformant H4735 was isolated.

For overexpression of *P. chrysoporium* oxaloacetase and N-terminally truncated *S. cerevisiae* HMG-CoA reductase (HMG1) pMIPk113 (SEQ ID NO: 9) was constructed. pMIPk113 (SEQ ID NO: 9) consists of *P. kudriavzevii* PDC1 3' homology region, MEL5 marker flanked by loxP sites—*P. kudriavzevii* TDH1 promoter—*P. chrysosporium oah*—*S. cerevisiae* PGK1 terminator—*P. kudriavzevii* PGK1 promoter—*S. cerevisiae* HMG1—*S. cerevisiae* ADH1 terminator—*P. kudriavzevii* PDC1 5' homology region. pMIPk113 (SEQ ID NO: 9) was digested with NotI and transformed into *P. kudriavzevii* H4735 using the lithium acetate method. The transformants were selected based on blue colour on yeast peptone dextrose (YPD) medium containing 5-bromo-4-chloro-3-indolyl-α-D-galactopyranoside (X-alpha-gal). The presence of the transforming DNA in the transformant yLIF-142 was confirmed by PCR.

For overexpression of pyruvate carboxylase pMIPk118 (SEQ ID NO: 5) was digested with NotI and transformed into *P. kudriavzevii* yLIF-142 using the lithium acetate method. The transformants were selected on yeast peptone dextrose (YPD) medium containing 500 μg/ml hygromycin. The presence of the transforming DNA in the transformant yLIF-146 was confirmed by PCR.

The MEL5 and hygromycin resistance markers are excised from yLIF-146 using the Cre-loxP system as described above. Both copies of diploid *P. kudriavzevii* MLS1 genes are replaced by *A. thaliana* GLYR1 as described in (Koivistoinen et al. WO 2013/050659). The transformation marker genes hph and MEL5, located between loxP sites, are removed from the genome with the Cre recombinase expression plasmid pKLNatCre+loPGK. The markerless strain is then transformed with NotI digested pMLV209 (SEQ ID NO: 6). The presence of oxalate-CoA ligase and oxalyl-CoA reductase is verified by PCR. The resulting strain has pathways for production of isoprene and oxalate, oxalyl-coA, glyoxylate and/or glycolic acid directly from glucose.

The resulting strains are cultivated in minimal and/or rich media and the glycolic acid produced in the culture supernatant is measured as described in example 2. Production of isoprene is measured with mass spectrometry.

Example 5. Co-Production of Glycolic Acid and Triacylglycerids

In order to produce both glycolic acid and triacylglycerids, the *Pichia kudriavzevii* strain yLIF309 producing glycolic acid is modified to also produce triacylglycerids as described in Runguphan (2014, Metab Eng. 21:103-13). Codon optimised synthetic genes coding for acetyl-CoA carboxylase and fatty acid synthase are cloned under constitutive, endogenous promoters and introduced into the genome of *P. kudriavzevii* by either homologous recombination into targeted gene loci or by random integration into the genome. The resulting strains are cultivated in minimal and/or rich media and the glycolic acid produced in the culture supernatant is measured as described in example 2. Production of triacylglycerids is measured with mass spectrometry.

Example 6. Production of Glycolic Acid from Oxalate

In order to produce glycolic acid from oxalate, the *Pichia kudriavzevii* strain yLIF309 producing glycolic acid is cultivated in minimal and/or rich media containing oxalate and/or oxalic acid and the glycolic acid produced in the culture supernatant is measured as described in example 2.

The invention claimed is:

1. A method of producing glycolic acid, said method comprising:

providing a fungus that has been genetically modified to express or overexpress a gene encoding oxalyl-CoA ligase, oxalyl-CoA reductase and/or ketopantoate reductase; and culturing said fungus in a carbon substrate containing medium to obtain glycolic acid.

2. A method of converting oxalate to oxalyl-coA and/or oxalyl-coA to glyoxylate in a fungus, said method comprising:

providing a fungus that has been genetically modified to express or overexpress a gene encoding oxalyl-CoA ligase, oxalyl-CoA reductase and/or ketopantoate reductase; and culturing said fungus in a carbon substrate containing medium to obtain oxalyl-coA and/or glyoxylate.

3. The method of claim 1, further comprising recovering the resulting glycolic acid from the medium.

4. The method of claim 1, further comprising isolating and/or purifying glycolic acid.

5. The method of claim 1, wherein the carbon substrate is selected from the group consisting of pentose such as xylose, xylan or other oligomer of xylose; hexose such as glucose, fructose, mannose or galactose and oligomers of glucose such as maltose, maltotriose, isomaltotriose, starch or cellulose, and sugars such a sugars derived from lignocellulose, oxalate, $CO_2$, ethanol, and any combination thereof.

6. A genetically modified fungus comprising increased enzyme activity associated with oxalyl-CoA, as compared to a genetically unmodified fungus, wherein the enzyme activity associated with oxalyl-CoA is oxalyl-CoA ligase activity, oxalyl-CoA reductase activity or ketopantoate reductase activity, or any combination thereof.

7. The method of claim 1, wherein the enzyme activity associated with oxalyl-CoA is oxalate-CoA ligase activity or oxalyl-CoA reductase activity or ketopantoate reductase activity, or any combination thereof.

8. The method of claim 1, wherein the fungus has been genetically modified to increase oxalate-CoA ligase activity and either oxalyl-CoA reductase activity or ketopantoate reductase activity.

9. The method of claim 1, wherein the fungus has increased glycolic acid, oxalate, oxalyl-coA and/or glyoxylate production.

10. The method of claim 1, wherein the fungus has been genetically modified to express or overexpress a gene encoding oxalate-CoA ligase and/or oxalyl-CoA reductase and/or ketopantoate reductase activity.

11. The method of claim 1, wherein the fungus has further been genetically modified to increase glyoxylate reductase activity, oxaloacetase activity, pyruvate carboxylase activity, carbonate dehydratase activity, isoprene synthase activity, isopentenyldiphosphate delta-isomerase activity, HMG-CoA reductase activity, fatty acid synthase activity and/or acetyl-CoA carboxylase activity, or any combination thereof.

12. The method of claim 11, wherein the fungus has been genetically modified to express or overexpress a gene encoding glyoxylate reductase, oxaloacetase, pyruvate carboxylase, carbonate dehydratase, isoprene synthase, isopentenyl-diphosphate delta-isomerase, HMG-CoA reductase, fatty acid synthase and/or acetyl-CoA carboxylase, or any combination thereof.

13. The method of claim 1, wherein the fungus further comprises a genetic modification of one or more genes selected from the group consisting of MLS, PDC, GPD, IDP and any combination thereof, or further comprises a genetic modification of a promoter.

14. The method of claim 13, wherein the fungus has been genetically modified by deleting at least part of a gene or by inactivating a gene selected from the group consisting of MLS, PDC, GPD, IDP and any combination thereof.

15. The method of claim 1, wherein the isoprene pathway, triacylglyceride pathway, lipid pathway and/or any pathway starting from acetate/acetyl-CoA is present in said fungus.

16. The method of claim 1, wherein glycolic acid is co-produced with isoprene.

17. The method of claim 1, wherein the fungus is a yeast or filamentous fungus.

18. The method of claim 17, wherein the fungus is a yeast selected from the genera *Arxula, Cryptococcus, Candida, Debaryomyces, Galactomyces, Hansenula, Kazachstania, Kluyveromyces, Lipomyces, Lodderomyces, Metschnikowia, Millerozyma, Priceomyces, Rhodosporidium, Rhodotorula, Saccharomyces, Sugiyamaella, Trichosporon, Pichia* and *Yarrowia* and *Zygosaccharomyces*, specifically from the group consisting of *Arxula adeninivorans, Candida* sp., *Candida catenulata, Candida glycerinogenes, Candida haemulonii, Candida humilis Candida maltosa, Candida parapsilopsis, Candida rhagii, Candida rugosa, Candida sake, Candida tenuis Cryptococcus curvatus, Cryptococcus albidus, Debaryomyces hansenii, Debaryomyces robertsiae, Galactomyces geotrichum, Hansenula* ciferri, *Kazachstania exigua, Klyuveromyces lactis, Kluyveromyces marxianus, Lipomyces lipofer, Lipomyces* ssp., *Lipomyces starkeyi,*

*Lipomyces tetrasporus, Lodderomyces elongisporus, Metchnikowia pulcherrima, Metschnikowia reukaufii, Millerozyma farinosa, Priceomyces haplophilus, Rhodosporidium toruloides, Rhodotorula glutinis, Rhodotorula gracilis, Saccharomyces cerevisiae, Sugiyamaeiia smithiae, Trichosporon pullulans, Trichosporon veenhuisii, Pichia jadinii, Pichia fermentans, Pichia membranifaciens, Pichia guilliermondii, Pichia kudriavzevii, Pichia stipitis*, and *Yarrowia lipolytica*, and *Zygosaccharomyces lentus* or a filamentous fungus selected from the genera *Aspergillus, Cunninghamella, Fusarium, Glomus, Humicola, Mortierella, Mucor, Penicillium, Pythium* and *Rhizopus*, specifically from the group consisting of *Aspergillus nidulans, Aspergillus oryzae, Aspergillus terreus, Aspergillus niger, Cuninghamella blakesleeana, Cuninghamella japonica, Fusarium moniliforme, Fusarium oxysporum, Glomus caledonius, Humicola lanuginose, Mortierella isabellina, Mortierella pusilla, Mortierella vinacea, Mucor circinelloides, Mucor plumbeus, Mucor ramanniana, Penicillium frequentans, Penicillium lilacinum, Penicillium soppii, Penicillium spinulosum, Pythium ultimum* and *Rhizopus oryzae*, and *Trichoderma reesei*.

19. The method of claim 18, wherein the yeast is *Pichia* kudriavzevii.

20. A method of producing one or more products selected from the group consisting of polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, and pharmaceuticals, said method comprising culturing the genetically modified fungus of claim 6 in a carbon substrate containing medium to produce glycolic acids, recovering the resulting glycolic acids and utilizing the recovered glycolic acids in production of polymers, emulsion polymers, biocompatible copolymers, polyglycolic acids, hot-melt adhesives, surfactants, surface treatment products, adhesives, food additives, flavoring agents, preservatives, solvents, cleaning additives or products, dyeing or tanning agents, plasticizers, fragrances, cosmetics, skin care agents and products, or pharmaceuticals.

21. A method of preparing the genetically modified fungus of claim 6, wherein said method comprises providing a fungus and genetically modifying the fungus to increase an enzyme activity associated with oxalyl-CoA.

* * * * *

SEQUENCE LISTING

```
<160> NUMBER OF SEQ ID NOS: 9

<210> SEQ ID NO 1
<211> LENGTH: 49
<212> TYPE: DNA
<213> ORGANISM: Artificial Sequence
<220> FEATURE:
<223> OTHER INFORMATION: polynucleotide primer

<400> SEQUENCE: 1

cctccactag tggtctcaga tctagaatga gcagtagcaa gaaattggc              49


<210> SEQ ID NO 2
<211> LENGTH: 42
<212> TYPE: DNA
<213> ORGANISM: Artificial Sequence
<220> FEATURE:
<223> OTHER INFORMATION: polynucleotide primer

<400> SEQUENCE: 2

tccaaagctt ggtctcagat cttacttttt ttgggatggg gg                     42


<210> SEQ ID NO 3
<211> LENGTH: 8409
<212> TYPE: DNA
<213> ORGANISM: Artificial Sequence
<220> FEATURE:
<223> OTHER INFORMATION: expression vector pMIPk117
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (5120)..(5120)
<223> OTHER INFORMATION: n is a, c, g, or t

<400> SEQUENCE: 3

aattcttgct gcaacggcaa catcaatgtc cacgtttaca cacctacatt tatatctata     60

tttatattta tatttattta tttatgctac ttagcttcta tagttagtta atgcactcac    120

gatattcaaa attgacaccc ttcaactact ccctactatt gtctactact gtctactact    180

cctctttact atagctgctc ccaataggct ccaccaatag gctctgtcaa tacattttgc    240

gccgccacct ttcaggttgt gtcactcctg aaggaccata ttgggtaatc gtgcaatttc    300

tggaagagag tgccgcgaga agtgaggccc ccactgtaaa tcctcgaggg ggcatggagt    360

atggggcatg naggatggag gatggggggg gggggggaaa ataggtagcg aaaggacccg    420

ctatcacccc acccggagaa ctcgttgccg ggaagtcata tttcgacact ccggggagtc    480

tataaaaggc gggttttgtc ttttgccagt tgatgttgct gagaggactt gtttgccgtt    540
```

-continued

```
tcttccgatt taacagtata gaatcaacca ctgttaatta tacacgttat actaacacaa    600
caaaaacaaa aacaacgaca acaacaacaa caatgtttgc tttctacttt ctcaccgcat    660
gcaccacttt gaagggtgtt ttcggagttt ctccgagtta caatggtctt ggtctcaccc    720
cacagatggg ttgggacagc tggaatacgt ttgcctgcga tgtcagtgaa cagctacttc    780
tagacactgc tgatagaatt tctgacttgg ggctaaagga tatgggttac aagtatgtca    840
tcctagatga ctgttggtct agcggcaggg attccgacgg tttcctcgtt gcagacaagc    900
acaaatttcc caacggtatg ggccatgttg cagaccacct gcataataac agctttcttt    960
tcggtatgta ttcgtctgct ggtgagtaca cctgtgctgg gtaccctggg tctctggggc   1020
gtgaggaaga agatgctcaa ttctttgcaa ataaccgcgt tgactacttg aagtatgata   1080
attgttacaa taaaggtcaa tttggtacac cagacgtttc ttaccaccgt tacaaggcca   1140
tgtcagatgc tttgaataaa actggtaggc ctattttcta ttctctatgt aactggggtc   1200
aggatttgac attttactgg ggctctggta tcgccaattc ttggagaatg agcggagata   1260
ttactgctga gttcacccgt ccagatagca gatgtccctg tgacggtgac gaatatgatt   1320
gcaagtacgc cggtttccat tgttctatta tgaatattct taacaaggca gctccaatgg   1380
ggcaaaatgc aggtgttggt ggttggaacg atctggacaa tctagaggtc ggagtcggta   1440
atttgactga cgatgaggaa aaggcccatt tctctatgtg ggcaatggta aagtccccac   1500
ttatcattgg tgccgacgtg aatcacttaa aggcatcttc gtactcgatc tacagtcaag   1560
cctctgtcat cgcaattaat caagatccaa agggtattcc agccacaaga gtctggagat   1620
attatgtttc agacaccgat gaatatggac aaggtgaaat tcaaatgtgg agtggtccgc   1680
ttgacaatgg tgaccaagtg gttgctttat tgaatggagg aagcgtagca agaccaatga   1740
acacgacctt ggaagagatt ttctttgaca gcaatttggg ttcaaaggaa ctgacatcga   1800
cttgggatat ttacgactta tgggccaaca gagttgacaa ctctacggcg tctgctatcc   1860
ttgaacagaa taaggcagcc accggtattc tctacaatgc tacagagcag tcttataaag   1920
acggtttgtc taagaatgat acaagactgt ttggccagaa aattggtagt ctttctccaa   1980
atgctatact taacacaact gttccagctc atggtatcgc cttctatagg ttgagaccct   2040
cggcttaagc tcaatgttga gcaaagcagg acgagaaaaa aaaaaaataat gattgttaag   2100
aagttcatga aaaaaaaaag gaaaaatact caaatactta taacagagtg attaaataat   2160
aaacggcagt ataccctatc aggtattgag atagttttat ttttgtaggt atataatctg   2220
aagcctttga actattttct cgtatatatc atggagtata cattgcatta gcaacattac   2280
atactaggat ctctagacct aataacttcg tatagcatac attatacgaa gttatattaa   2340
gggttgtcga cgatatggat atggatatgg atatggagat gaatttgaat ttagatttgg   2400
gtcttgattt ggggttggaa ttaaaagggg ataacaatga gggttttcct gttgatttaa   2460
acaatggacg tgggaggtga ttgatttaac ctgatccaaa aggggtatgt ctattttta   2520
gagagtgttt ttgtgtcaaa ttatggtaga atgtgtaaag tagtataaac tttcctctca   2580
aatgacgagg tttaaaacac cccccgggtg agccgagccg agaatggggc aattgttcaa   2640
tgtgaaatag aagtatcgag tgagaaactt gggtgttggc cagccaaggg ggggggggaa   2700
ggaaaatggc gcgaatgctc aggtgagatt gttttggaat tgggtgaagc gaggaaatga   2760
gcgacccgga ggttgtgact ttagtggcgg aggaggacgg aggaaaagcc aagagggaag   2820
tgtatataag gggagcaatt tgccaccagg atagaattgg atgagttata attctactgt   2880
atttattgta taatttattt ctccttttgt atcaaacaca ttacaaaaca cacaaaacac   2940
```

-continued

```
acaaacaaac acaattacaa aaattaatta aaaaatgacc atcaccatca ccgtcgaaaa   3000

ggatggttat tacgaagtta acggtactag acaagaacct accgtttcct tgtatgttat   3060

tccagctgct tctaagttga gaagaatgtt gaaagatacc aaggacttga tcgtttgtcc   3120

aggtgtttat gatggtttgt ctgctagaat tgctatggaa gttggtttca agggtttgta   3180

tatgactggt gctggtacta ctgcttcaag attgggtatg gctgatttgg gtttggctca   3240

attgcatgat atgaagacta acgctgaaat gattgctaac ttggacccat ttggtccacc   3300

attgattgct gatatggata ctggttatgg tggtccattg atggtttcta agtccgtcca   3360

acaatatatt caagctggtg ttgctggttt ccacatcgaa gatcaaattc aaaacaagag   3420

atgcggtcac ttgaacggta aaaaagttgt tggtttggaa gaatacttga tgagaattag   3480

agctgccaag ttgaccaagg atagattgca ttctgatatt gtcttgatcg ctagaactga   3540

tgccttgcaa caacatggtt acgatgaatg cattagaaga ttgaaggctg ccagagatat   3600

tggtgctgat gttggtttat tggaaggttt cacctctaaa gaacaagcta gacaagctgt   3660

tcaagatttg gctccatggc ctttgttgtt gaatatggtt gaaaatggtg cctccccatt   3720

gattactaca aaagaagctg aagaaatggg tttcagaatt atgattttct ccttcgctac   3780

tattacccca gcttacatgg gtattaaggc tactttggaa agattgaaaa ccgatggtgt   3840

tgttggtgta ccagaaggtt taggtccaag aactattttc gaagtttgcg gtttgatgga   3900

ctccatgaag gttgatactg aatctggtaa cgatggtttt gctgaaggtg tttgattaat   3960

taacccatgt ctctactggt ggtggtgctt ctttggaatt attggaaggt aaggaattgc   4020

caggtgttgc tttcttatcc gaaaagaaat aaattgaatt gaattgaaat cgatagatca   4080

atttttttct tttctctttc cccatccttt acgctaaaat aatagtttat tttatttttt   4140

gaatattttt tatttatata cgtatatata gactattatt tatcttttaa tgattattaa   4200

gatttttatt aaaaaaaaat tcgctcctct tttaatgcct ttatgcagtt tttttttccc   4260

attcgatatt tctatgttcg ggttcagcgt attttaagtt taataactcg aaaattctgc   4320

gttcgttaag tcgacggatc cgtatcattt gtagcccacg ccacccggaa aaaccaccat   4380

tgtcctcagc agtccgccaa aatatggatg cgctcaatca actttccctc ccccgtcaat   4440

gccaaaagga taacgacaca ctattaagag cgcatcattt gtaaaagccg aggaaggggg   4500

atacgctaac cggagacgtc tcgcctcact ctcggagctg agccgccctc cttaagaaat   4560

tcatgggaag aacacccttc gcggcttctg aacggctcgc cctcgtccat tggtcacctc   4620

acagtggcaa ctaataagga cattatagca atagaaatta aaatggtgca cagaaataca   4680

ataggatcga ataggatagg atacaataag atacggaata ttagactata ctgtgatacg   4740

gtacggtacg atacgctacg atacgatacg atagaggata ccacggatat aacgtagtat   4800

tatttttcat tattggggt tttttctgt ttgaatttc cacgtcaaga gtatcccatc   4860

tgacaggaac cgatggactc gtcacagtac ctatcgcccg agttcaatcc atggacgctt   4920

cgggtgaagg atcttcgtcc gctgttggca agccatggga tcagggcgtc gccaagggac   4980

agaaaggcgg atcttgtacg tctcttcaac acagagctgc gtccgaaact tactgagagt   5040

cttaacacca ataatcccaa aaacaacaac aacaatacag atactataga cactatagac   5100

actatagaca ctactaacan ccctttaaag cgccgccgat taagcaatgt tgatgagccg   5160

tcaattccat atactctgca gcgtacgaag cttcagctgg cggccgcgtt ctatagtgtc   5220

acctaaatcg tatgtgtatg atacataagg ttatgtatta attgtagccg cgttctaacg   5280
```

-continued

```
acaatatgtc catatggtgc actctcagta caatctgctc tgatgccgca tagttaagcc   5340
agccccgaca cccgccaaca cccgctgacg cgccctgacg ggcttgtctg ctcccggcat   5400
ccgcttacag acaagctgtg accgtctccg ggagctgcat gtgtcagagg ttttcaccgt   5460
catcaccgaa acgcgcgaga cgaaagggcc tcgtgatacg cctattttta taggttaatg   5520
tcatgataat aatggtttct tagacgtcag gtggcacttt tcggggaaat gtgcgcggaa   5580
cccctatttg tttatttttc taaatacatt caaatatgta tccgctcatg agacaataac   5640
cctgataaat gcttcaataa tattgaaaaa ggaagagtat gagtattcaa catttccgtg   5700
tcgcccttat tccctttttt gcggcatttt gccttcctgt ttttgctcac ccagaaacgc   5760
tggtgaaagt aaaagatgct gaagatcagt tgggtgcacg agtgggttac atcgaactgg   5820
atctcaacag cggtaagatc cttgagagtt ttcgccccga agaacgtttt ccaatgatga   5880
gcacttttaa agttctgcta tgtggcgcgg tattatcccg tattgacgcc gggcaagagc   5940
aactcggtcg ccgcatacac tattctcaga atgacttggt tgagtactca ccagtcacag   6000
aaaagcatct tacggatggc atgacagtaa gagaattatg cagtgctgcc ataaccatga   6060
gtgataacac tgcggccaac ttacttctga caacgatcgg aggaccgaag gagctaaccg   6120
cttttttgca caacatgggg gatcatgtaa ctcgccttga tcgttgggaa ccggagctga   6180
atgaagccat accaaacgac gagcgtgaca ccacgatgcc tgtagcaatg gcaacaacgt   6240
tgcgcaaact attaactggc gaactactta ctctagcttc ccggcaacaa ttaatagact   6300
ggatggaggc ggataaagtt gcaggaccac ttctgcgctc ggcccttccg gctggctggt   6360
ttattgctga taaatctgga gccggtgagc gtgggtctcg cggtatcatt gcagcactgg   6420
ggccagatgg taagccctcc cgtatcgtag ttatctacac gacggggagt caggcaacta   6480
tggatgaacg aaatagacag atcgctgaga taggtgcctc actgattaag cattggtaac   6540
tgtcagacca agtttactca tatatacttt agattgattt aaaacttcat ttttaattta   6600
aaaggatcta ggtgaagatc ctttttgata atctcatgac caaaatccct taacgtgagt   6660
tttcgttcca ctgagcgtca gaccccgtag aaaagatcaa aggatcttct tgagatcctt   6720
tttttctgcg cgtaatctgc tgcttgcaaa caaaaaaacc accgctacca gcggtggttt   6780
gtttgccgga tcaagagcta ccaactcttt ttccgaaggt aactggcttc agcagagcgc   6840
agataccaaa tactgtcctt ctagtgtagc cgtagttagg ccaccacttc aagaactctg   6900
tagcaccgcc tacatacctc gctctgctaa tcctgttacc agtggctgct gccagtggcg   6960
ataagtcgtg tcttaccggg ttggactcaa gacgatagtt accggataag gcgcagcggt   7020
cgggctgaac ggggggttcg tgcacacagc ccagcttgga gcgaacgacc tacaccgaac   7080
tgagatacct acagcgtgag cattgagaaa gcgccacgct tcccgaaggg agaaaggcgg   7140
acaggtatcc ggtaagcggc agggtcggaa caggagagcg cacgagggag cttccagggg   7200
gaaacgcctg gtatctttat agtcctgtcg ggtttcgcca cctctgactt gagcgtcgat   7260
ttttgtgatg ctcgtcaggg gggcggagcc tatggaaaaa cgccagcaac gcggcctttt   7320
tacggttcct ggccttttgc tggccttttg ctcacatgtt ctttcctgcg ttatcccctg   7380
attctgtgga taaccgtatt accgcctttg agtgagctga taccgctcgc cgcagccgaa   7440
cgaccgagcg cagcgagtca gtgagcgagg aagcggaaga gcgcccaata cgcaaaccgc   7500
ctctccccgc gcgttggccg attcattaat gcaggttaac ctggcttatc gaaattaata   7560
cgactcacta tagggagacc ggcagatccg cggccgcaat agagagtgac ctatccaagc   7620
tttgggggtc taagttttaa tggcccaggg aatcattact ttttttctc aatccttgat   7680
```

```
ggataaaagt attacatacg tacaggattg tgtattagtg tatttcgtta tatgattaaa   7740

caaagtttat agattgtaaa gtagacgtaa agtttagtaa ttcattttaa tgttcatttt   7800

acattcagat gtcattaagc ggctttagag ttgatttcat cagataattt agcttgagca   7860

accaagattt ctggagcatc gaattcatcc aagaataatt caatgactct aatcttatct   7920

tccttgttga atgcttcatc cttcatcaaa gcgtccaagt ccttagcgga tttaacaaca   7980

tggttttcat attgggtctt gtcagcaaag agcttcaata acaattggtg atcccatggt   8040

tgaatttggt tgtagtcctc atgacgaccg tggatcaact tttcgatagt gtaacctctg   8100

ttgtttaaga tgaagatgta tggcttgatg ttccatcttg cagcatctga gattgattgg   8160

acagtcaatt gtaaagaacc atcaccaata aacaaaacag ttcttctttc ttgttcgcca   8220

gtttgtttgt gtgcatcttc agcagcaaat gcagcaccaa ctgcagctgg taaggagaaa   8280

ccaatggaac cccataagac ttgggagata gactttgaat ctcttggtat gggtagccaa   8340

gactagtcga tatcacctaa taacttcgta tagcatacat tatacgaagt tatattaagg   8400

gttctcgag                                                           8409
```

```
<210> SEQ ID NO 4
<211> LENGTH: 8078
<212> TYPE: DNA
<213> ORGANISM: Artificial Sequence
<220> FEATURE:
<223> OTHER INFORMATION: DNA construct pMLV132B
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (5631)..(5631)
<223> OTHER INFORMATION: n is a, c, g, or t

<400> SEQUENCE: 4
```

```
gaacgcggcc gcgagctcta agttttaatg gcccagggaa tcattacttt tttttctcaa     60

tccttgatgg ataaaagtat tacatacgta caggattgtg tattagtgta tttcgttata    120

tgattaaaca aagtttatag attgtaaagt agacgtaaag tttagtaatt cattttaatg    180

ttcattttac attcagatgt cattaagcgg ctttagagtt gatttcatca gataatttag    240

cttgagcaac caagatttct ggagcatcga attcatccaa gaataattca atgactctaa    300

tcttatcttc cttgttgaat gcttcatcct tcatcaaagc gtccaagtcc ttagcggatt    360

taacaacatg gttttcatat tgggtcttgt cagcaaagag cttcaataac aattggtgat    420

cccatggttg aatttggttg tagtcctcat gacgaccgtg gatcaacttt tcgatagtgt    480

aacctctgtt gtttaagatg aagatgtatg gcttgatgtt ccatcttgca gcatctgaga    540

ttgattggac agtcaattgt aaagaaccat caccaataaa caaaacagtt cttctttctt    600

gttcgccagt ttgtttgtgt gcatcttcag cagcaaatgc agcaccaact gcagctggta    660

aggagaaacc aatggaaccc cataagactt gggagataga ctttgaatct cttggtatgg    720

gtagccaaga ctagtcgata tcacctaata acttcgtata gcatacatta tacgaagtta    780

tattaagggt tctcgagaat tcttgctgca acggcaacat caatgtccac gtttacacac    840

ctacatttat atctatattt atatttatat ttatttattt atgctactta gcttctatag    900

ttagttaatg cactcacgat attcaaaatt gacacccttc aactactccc tactattgtc    960

tactactgtc tactactcct ctttactata gctgctccca ataggctcca ccaataggct   1020
```

-continued

```
ctgtcaatac attttgcgcc gccacctttc aggttgtgtc actcctgaag gaccatattg   1080
ggtaatcgtg caatttctgg aagagagtgc cgcgagaagt gaggccccca ctgtaaatcc   1140
tcgagggggc atggagtatg gggcatgnag gatggaggat gggggggggg ggggaaaata   1200
ggtagcgaaa ggacccgcta tcaccccacc cggagaactc gttgccggga agtcatattt   1260
cgacactccg gggagtctat aaaaggcggg ttttgtcttt tgccagttga tgttgctgag   1320
aggacttgtt tgccgtttct tccgatttaa cagtatagaa tcaaccactg ttaattatac   1380
acgttatact aacacaacaa aaacaaaaac aacgacaaca acaacaacaa tgcctgaact   1440
caccgcgacg tctgtcgaga agtttctgat cgaaaagttc gacagcgtct ccgacctgat   1500
gcagctctcg gagggcgaag aatctcgtgc tttcagcttc gatgtaggag ggcgtggata   1560
tgtcctgcgg gtaaatagct gcgccgatgg tttctacaaa gatcgttatg tttatcggca   1620
ctttgcatcg gccgcgctcc cgattccgga agtgcttgac attggggaat tcagcgagag   1680
cctgacctat tgcatctccc gccgtgcaca gggtgtcacg ttgcaagacc tgcctgaaac   1740
cgaactgccc gctgttctgc agccggtcgc ggaggccatg gatgcgatcg ctgcggccga   1800
tcttagccag acgagcgggt tcggcccatt cggaccgcaa ggaatcggtc aatacactac   1860
atggcgtgat ttcatatgcg cgattgctga tccccatgtg tatcactggc aaactgtgat   1920
ggacgacacc gtcagtgcgt ccgtcgcgca ggctctcgat gagctgatgc tttgggccga   1980
ggactgcccc gaagtccggc acctcgtgca cgcggatttc ggctccaaca atgtcctgac   2040
ggacaatggc cgcataacag cggtcattga ctggagcgag gcgatgttcg gggattccca   2100
atacgaggtc gccaacatct tcttctggag gccgtggttg gcttgtatgg agcagcagac   2160
gcgctacttc gagcggaggc atccggagct tgcaggatcg ccgcggctcc gggcgtatat   2220
gctccgcatt ggtcttgacc aactctatca gagcttggtt gacggcaatt tcgatgatgc   2280
agcttgggcg cagggtcgat gcgacgcaat cgtccgatcc ggagccggga ctgtcgggcg   2340
tacacaaatc gcccgcagaa gcgcggccgt ctggaccgat ggctgtgtag aagtactcgc   2400
cgatagtgga aaccgacgcc ccagcactcg tccgagggca aaggaataga gtagtaagct   2460
caatgttgag caaagcagga cgagaaaaaa aaaaataatg attgttaaga agttcatgaa   2520
aaaaaaaagg aaaaatactc aaatacttat aacagagtga ttaaataata aacggcagta   2580
taccctatca ggtattgaga tagttttatt tttgtaggta tataatctga agcctttgaa   2640
ctattttctc gtatatatca tggagtatac attgcattag caacattaca tactaggatc   2700
tctagaccta ataacttcgt atagcataca ttatacgaag ttatattaag ggttgtcgac   2760
ggatccgtgt ggaagaacga ttacaacagg tgttgtcctc tgaggacata aaatacacac   2820
cgagattcat caactcattg ctggagttag catatctaca attgggtgaa atggggagcg   2880
atttgcaggc atttgctcgg catgccggta gaggtgtggt caataagagc gacctcatgc   2940
tatacctgag aaagcaacct gacctacagg aaagagttac tcaagaataa gaattttcgt   3000
tttaaaacct aagagtcact ttaaaatttg tatacactta tttttttttat aacttattta   3060
ataataaaaa tcataaatca taagaaattc gcttatttag aagtgtcaac aacgtatcta   3120
ccaacgattt gacccttttc catcttttcg taaatttctg gcaaggtaga caagccgaca   3180
accttgattg gagacttgac caaacctctg gcgaagaagt ccaaagcttg gaagatcttt   3240
aaacgaagat aggtatgttg tcccaatccc aaggatcatt gaatcttaaa cctatgtcca   3300
acttggcaat gttatctaag tcatctttag tcaagtcgaa atcgacaact gacaaatttt   3360
gtgccaatct ttcagggttg ttagactttg gaattactgc gatgtttctt tgtgtagccc   3420
```

-continued

```
atcttaacaa gacttgggct ggacttttac cgtgtttatc tgcgatggac ttaatagttt   3480

catgttcgaa caaggtaggt gtgttcaatg ctctctttga ttccaattcc aagaaagatt   3540

gtggaccaaa tgaagagtaa cctgtaatag cgataccggc cttttggacg tattctatca   3600

atttaggttg ttgcaaatat gggtgatgtt caatttgcaa aacggcaggt ttgatggttg   3660

cacctctgat caaatcatag atcaaagcac ctgtaaagtt actgataccg atggacttaa   3720

ttttaccagc ttcaactaac ttttccaagg ctttccaagt gtctaacaat ggtacatctt   3780

cgtaatggaa attgtcaccg tcaccgcagt aaaaaccagg tggatacttt tcttcgatag   3840

gtacgaattt aaaagcgatt gggaagtgga ttaaaaacaa gtcgacgtaa tccaaattca   3900

agtctgacaa agtcttgttc aaagcggttt caacattttt aggatcatgg aagttgttcc   3960

acaacttaga tgtaataaac aattcttctc tcttgaccaa accatctttt atagctctgt   4020

taataccttc accaacttcc ttttcgttac catagtcttc ggcaccatcg aataatctgt   4080

aaccggtctt gattgcgtta tatatttgat ctgcagctgt agcattagta actttccaac   4140

aaccaaaacc tactaaaggc atttcgtaac cagagtttaa tttaatagtt ggggtgttaa   4200

ctgtagtgga cattctagat cttgttgttg ttgttgtcgt tgtttttgtt tttgttgtgt   4260

tagtataacg tgtataatta acagtggttg attctatact gttaaatcgg aagaaacggc   4320

aaacaagtcc tctcagcaac atcaactggc aaaagacaaa acccgccttt tatagactcc   4380

ccggagtgtc gaaatatgac ttcccggcaa cgagttctcc gggtggggtg atagcgggtc   4440

ctttcgctac ctatttttcg cccccccca tcctccatcc tccatgcccc atactccatg   4500

ccccctcgag gatttacagt gggggcctca cttctcgcgg actctcttcc agaaattgca   4560

cgattaccca atatggtcct tcaggagtga cacaacctga aaggtggcgg cgcaaaatgt   4620

attggcagag cctattggtg gagcctattg ggagcagcta tagtaaagag gagtagtaga   4680

cagtagtaga caatagtagg gagtagttga agggtgtcaa ttttgaatat cgtgagtgca   4740

ttaactaact atagaagcta agtagcataa ataaataaat ataaatataa atatagatat   4800

aaatgtaggt gtgtaaacgt ggacattgat gttgccgttg cagcaaggat ccgtatcatt   4860

tgtagcccac gccacccgga aaaaccacca ttgtcctcag cagtccgcca aaatatggat   4920

gcgctcaatc aactttccct cccccgtcaa tgccaaaagg ataacgacac actattaaga   4980

gcgcatcatt tgtaaaagcc gaggaagggg gatacgctaa ccggagacgt ctcgcctcac   5040

tctcggagct gagccgccct ccttaagaaa ttcatgggaa gaacaccctt cgcggcttct   5100

gaacggctcg ccctcgtcca ttggtcacct cacagtggca actaataagg acattatagc   5160

aatagaaatt aaaatggtgc acagaaatac aataggatcg aataggatag gatacaataa   5220

gatacggaat attagactat actgtgatac ggtacggtac gatacgctac gatacgatac   5280

gatagaggat accacggata taacgtagta ttatttttca ttattggggg tttttttctg   5340

tttgaatttt ccacgtcaag agtatcccat ctgacaggaa ccgatggact cgtcacagta   5400

cctatcgccc gagttcaatc catggacgct tcgggtgaag gatcttcgtc cgctgttggc   5460

aagccatggg atcagggcgt cgccaaggga cagaaaggcg gatcttgtac gtctcttcaa   5520

cacagagctg cgtccgaaac ttactgagag tcttaacacc aataatccca aaaacaacaa   5580

caacaataca gatactatag acactataga cactatagac actactaaca nccctttaaa   5640

gcgccgccga ttaagcaatg ttgatgagcc gtcaattcca tatactcagc tggcggccgc   5700

ggatctgccg gtctccctat agtgagtcgt attaatttcg ataagccagg ttaacctgca   5760
```

-continued

```
ttaatgaatc ggccaacgcg cggggagagg cggtttgcgt attgggcgct cttccgcttc   5820
ctcgctcact gactcgctgc gctcggtcgt tcggctgcgg cgagcggtat cagctcactc   5880
aaaggcggta atacggttat ccacagaatc aggggataac gcaggaaaga acatgtgagc   5940
aaaaggccag caaaaggcca ggaaccgtaa aaaggccgcg ttgctggcgt ttttccatag   6000
gctccgcccc cctgacgagc atcacaaaaa tcgacgctca agtcagaggt ggcgaaaccc   6060
gacaggacta taaagatacc aggcgtttcc ccctggaagc tccctcgtgc gctctcctgt   6120
tccgaccctg ccgcttaccg gatacctgtc cgcctttctc ccttcgggaa gcgtggcgct   6180
ttctcaatgc tcacgctgta ggtatctcag ttcggtgtag gtcgttcgct ccaagctggg   6240
ctgtgtgcac gaaccccccg ttcagcccga ccgctgcgcc ttatccggta actatcgtct   6300
tgagtccaac ccggtaagac acgacttatc gccactggca gcagccactg gtaacaggat   6360
tagcagagcg aggtatgtag gcggtgctac agagttcttg aagtggtggc ctaactacgg   6420
ctacactaga aggacagtat ttggtatctg cgctctgctg aagccagtta ccttcggaaa   6480
aagagttggt agctcttgat ccggcaaaca aaccaccgct ggtagcggtg gtttttttgt   6540
ttgcaagcag cagattacgc gcagaaaaaa aggatctcaa gaagatcctt tgatcttttc   6600
tacggggtct gacgctcagt ggaacgaaaa ctcacgttaa gggattttgg tcatgagatt   6660
atcaaaaagg atcttcacct agatcctttt aaattaaaaa tgaagtttta aatcaatcta   6720
aagtatatat gagtaaactt ggtctgacag ttaccaatgc ttaatcagtg aggcacctat   6780
ctcagcgatc tgtctatttc gttcatccat agttgcctga ctccccgtcg tgtagataac   6840
tacgatacgg gagggcttac catctggccc cagtgctgca atgataccgc gagacccacg   6900
ctcaccggct ccagatttat cagcaataaa ccagccagcc ggaagggccg agcgcagaag   6960
tggtcctgca actttatccg cctccatcca gtctattaat tgttgccggg aagctagagt   7020
aagtagttcg ccagttaata gtttgcgcaa cgttgttgcc attgctacag gcatcgtggt   7080
gtcacgctcg tcgtttggta tggcttcatt cagctccggt tcccaacgat caaggcgagt   7140
tacatgatcc cccatgttgt gcaaaaaagc ggttagctcc ttcggtcctc cgatcgttgt   7200
cagaagtaag ttggccgcag tgttatcact catggttatg gcagcactgc ataattctct   7260
tactgtcatg ccatccgtaa gatgcttttc tgtgactggt gagtactcaa ccaagtcatt   7320
ctgagaatag tgtatgcggc gaccgagttg ctcttgcccg gcgtcaatac gggataatac   7380
cgcgccacat agcagaactt taaaagtgct catcattgga aaacgttctt cggggcgaaa   7440
actctcaagg atcttaccgc tgttgagatc cagttcgatg taacccactc gtgcacccaa   7500
ctgatcttca gcatctttta ctttcaccag cgtttctggg tgagcaaaaa caggaaggca   7560
aaatgccgca aaaaagggaa taagggcgac acggaaatgt tgaatactca tactcttcct   7620
ttttcaatat tattgaagca tttatcaggg ttattgtctc atgagcggat acatatttga   7680
atgtatttag aaaaataaac aaataggggt tccgcgcaca tttccccgaa aagtgccacc   7740
tgacgtctaa gaaaccatta ttatcatgac attaacctat aaaaataggc gtatcacgag   7800
gccctttcgt ctcgcgcgtt tcggtgatga cggtgaaaac ctctgacaca tgcagctccc   7860
ggagacggtc acagcttgtc tgtaagcgga tgccgggagc agacaagccc gtcagggcgc   7920
gtcagcgggt gttggcgggt gtcggggctg gcttaactat gcggcatcag agcagattgt   7980
actgagagtg caccatatgg acatattgtc gttagaacgc ggctacaatt aatacataac   8040
cttatgtatc atacacatac gatttaggtg acactata                           8078
```

```
<210> SEQ ID NO 5
<211> LENGTH: 10645
<212> TYPE: DNA
<213> ORGANISM: Artificial Sequence
<220> FEATURE:
<223> OTHER INFORMATION: DNA construct pMIPk118
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (8198)..(8198)
<223> OTHER INFORMATION: n is a, c, g, or t

<400> SEQUENCE: 5

gaacgcggcc gcgagctcta agttttaatg gcccagggaa tcattacttt tttttctcaa     60

tccttgatgg ataaaagtat tacatacgta caggattgtg tattagtgta tttcgttata    120

tgattaaaca aagtttatag attgtaaagt agacgtaaag tttagtaatt cattttaatg    180

ttcattttac attcagatgt cattaagcgg ctttagagtt gatttcatca gataatttag    240

cttgagcaac caagatttct ggagcatcga attcatccaa gaataattca atgactctaa    300

tcttatcttc cttgttgaat gcttcatcct tcatcaaagc gtccaagtcc ttagcggatt    360

taacaacatg gttttcatat tgggtcttgt cagcaaagag cttcaataac aattggtgat    420

cccatggttg aatttggttg tagtcctcat gacgaccgtg gatcaacttt tcgatagtgt    480

aacctctgtt gtttaagatg aagatgtatg gcttgatgtt ccatcttgca gcatctgaga    540

ttgattggac agtcaattgt aaagaaccat caccaataaa caaaacagtt cttctttctt    600

gttcgccagt ttgtttgtgt gcatcttcag cagcaaatgc agcaccaact gcagctggta    660

aggagaaacc aatggaaccc cataagactt gggagataga ctttgaatct cttggtatgg    720

gtagccaaga ctagtcgata tcacctaata acttcgtata gcatacatta tacgaagtta    780

tattaagggt tctcgagaat tcttgctgca acggcaacat caatgtccac gtttacacac    840

ctacatttat atctatattt atatttatat ttatttattt atgctactta gcttctatag    900

ttagttaatg cactcacgat attcaaaatt gacacccttc aactactccc tactattgtc    960

tactactgtc tactactcct ctttactata gctgctccca ataggctcca ccaataggct   1020

ctgtcaatac attttgcgcc gccacctttc aggttgtgtc actcctgaag gaccatattg   1080

ggtaatcgtg caatttctgg aagagagtgc cgcgagaagt gaggccccca ctgtaaatcc   1140

tcgagggggc atggagtatg gggcatgnag gatggaggat gggggggggg ggggaaaata   1200

ggtagcgaaa ggacccgcta tcaccccacc cggagaactc gttgccggga agtcatattt   1260

cgacactccg gggagtctat aaaaggcggg ttttgtcttt tgccagttga tgttgctgag   1320

aggacttgtt tgccgtttct tccgatttaa cagtatagaa tcaaccactg ttaattatac   1380

acgttatact aacacaacaa aaacaaaaac aacgacaaca acaacaacaa tgcctgaact   1440

caccgcgacg tctgtcgaga agtttctgat cgaaaagttc gacagcgtct ccgacctgat   1500

gcagctctcg gagggcgaag aatctcgtgc tttcagcttc gatgtaggag ggcgtggata   1560

tgtcctgcgg gtaaatagct gcgccgatgg tttctacaaa gatcgttatg tttatcggca   1620

ctttgcatcg gccgcgctcc cgattccgga agtgcttgac attggggaat tcagcgagag   1680

cctgacctat tgcatctccc gccgtgcaca gggtgtcacg ttgcaagacc tgcctgaaac   1740

cgaactgccc gctgttctgc agccggtcgc ggaggccatg gatgcgatcg ctgcggccga   1800

tcttagccag acgagcgggt tcggcccatt cggaccgcaa ggaatcggtc aatacactac   1860
```

-continued

```
atggcgtgat ttcatatgcg cgattgctga tccccatgtg tatcactggc aaactgtgat   1920
ggacgacacc gtcagtgcgt ccgtcgcgca ggctctcgat gagctgatgc tttgggccga   1980
ggactgcccc gaagtccggc acctcgtgca cgcggatttc ggctccaaca atgtcctgac   2040
ggacaatggc cgcataacag cggtcattga ctggagcgag gcgatgttcg gggattccca   2100
atacgaggtc gccaacatct tcttctggag gccgtggttg gcttgtatgg agcagcagac   2160
gcgctacttc gagcggaggc atccggagct tgcaggatcg ccgcggctcc gggcgtatat   2220
gctccgcatt ggtcttgacc aactctatca gagcttggtt gacggcaatt tcgatgatgc   2280
agcttgggcg cagggtcgat gcgacgcaat cgtccgatcc ggagccggga ctgtcgggcg   2340
tacacaaatc gcccgcagaa gcgcggccgt ctggaccgat ggctgtgtag aagtactcgc   2400
cgatagtgga aaccgacgcc ccagcactcg tccgagggca aaggaataga gtagtaagct   2460
caatgttgag caaagcagga cgagaaaaaa aaaaataatg attgttaaga agttcatgaa   2520
aaaaaaaagg aaaaatactc aaatacttat aacagagtga ttaaataata aacggcagta   2580
taccctatca ggtattgaga tagttttatt tttgtaggta tataatctga agcctttgaa   2640
ctattttctc gtatatatca tggagtatac attgcattag caacattaca tactaggatc   2700
tctagaccta ataacttcgt atagcataca ttatacgaag ttatattaag ggttgtcgac   2760
ggatccgtgt ggaagaacga ttacaacagg tgttgtcctc tgaggacata aaatacacac   2820
cgagattcat caactcattg ctggagttag catatctaca attgggtgaa atggggagcg   2880
atttgcaggc atttgctcgg catgccggta gaggtgtggt caataagagc gacctcatgc   2940
tatacctgag aaagcaacct gacctacagg aaagagttac tcaagaataa gaattttcgt   3000
tttaaaacct aagagtcact ttaaaatttg tatacactta ttttttttat aacttattta   3060
ataataaaaa tcataaatca taagaaattc gcttatttag aagtgtcaac aacgtatcta   3120
ccaacgattt gacccttttc catcttttcg taaatttctg gcaaggtaga caagccgaca   3180
accttgattg gagacttgac caaacctctg gcgaagaagt ccaaagcttg gaagatctta   3240
cttttttttgg gatgggggta gggtttcttc ttctaggaca accaacaaat ctgatgcgtc   3300
aacactttca ccatccttaa tgaaaacgtc tttaacttga ccatctgctg gtgaagagac   3360
aaccatttcc attttcatgg cactcaaaac agcaatcgat tcgccctttt tcaccaaaga   3420
ccctttatgt actttaactt ctatgataac accagccatt ggtgcaccga tttggtgagt   3480
atcgtggaca tcagcctttg gtttagcaac agattgtatg ttttgtgact tgtctgcaac   3540
tctgatcttt cttaattcac cgttcaattc aaaatacact tctctttgcc cagttttctt   3600
atttaagtca ccaacagctt gcaatttgat aatcaaagtc ttaccttgtt cgatggtgac   3660
ttcgatttct tcatcaggtt ctgctggtgc taggaaattt ttggttggta gaactgataa   3720
atcaccgtat gtttctctga tcttttggaa atcttcatag acccttggat acatattgta   3780
agaagcaaca tcgcattcat caatatcacc gaatctgttc tgcaagtctt ctctaatttt   3840
ttcgagatca aatggttcta attctaaacc tggacggcac gtcaactttc ttctcttgtt   3900
tctcaataca tcagatctta atggttctgg gaacccaccg tatggttgac caattaaacc   3960
ttcaaaaaag tccataacag agtcaggaaa gtccaaagaa ttagctaaac gtctaatatc   4020
gtcggaagtc agtttgttag aaaccatgaa ttgagctaaa tcaccgacaa ccttagaagt   4080
tggggtaact ttaacaatat ctcccagtag gtaattggct tctctgtaag ctcttttagt   4140
ttcagcccat tgttcaccaa gacccagttg ttgagcttgg aataacaagt tagtcaattg   4200
accacctggg atttcatgtt ggtaaacttc tggatctggt cccttcaagt cggcctcgaa   4260
```

```
acaagaatac aacagtctca tttcggccca gtatgcatct aattcacgaa catgctcaac   4320
gttaatccca gtatcaatgt taccttctaa tgaagccaac agtgcattaa ttgatggttg   4380
ggaagttaag cccgacattg aattgatagc tacatcgaca acatcagcac ctgctagggc   4440
acatgcagtc atagacgcaa cagcagtacc tgcggagtca tgactgtgaa catgaattgg   4500
taaatccgga tatctggttc ttagggagcc aattaataat ttggcagcgg ccggtttcat   4560
agtacctgcc atatccttaa tacccaagat atgtgtaccc atttgaacta ttttttcaac   4620
aacttctagg tagtagtcta agttgtattt cttacctggc tgaagcatgt caccagagta   4680
acaaacagta gcttcgacaa caccaccggc cttcttgaca gcattcacac caacttttaa   4740
ttgttctaaa tcattcaagg catcaaaaac tctaaatata tcaacaccat tatccttggc   4800
ttgcttgaca aaatggtcaa tagcattgtc aggtaatgaa gagtaagcca caccgttggc   4860
accacgtaat aacatttgga atggaatatt aggcaccaga gatcttaatt ttctcagacg   4920
ttcccatgga tcctcatgca agaatctcat tgcaacgtcg aatgtagcac caccccaaca   4980
ttctaaagcg aaagcacctg caagggcatg tgcggttgtt ggagcgattg tagccaaatc   5040
gtgggttctg actcttgttg caagtagaga ttgatgagcg tctctccagg tggtgtccat   5100
cagtagagta ccattgaact gtctgacttg cttggcaaat tcagatggtc cctttttccag   5160
tagcacttgt ctccatccgg atggtggtgc agactttgta acgttgatga cattgccctg   5220
agcatcgtgc aaatgggggga cacttggatt tgattttagt tttggcaagc caatttgacc   5280
cttaatagaa gaaccgttaa ctgccaagtc tgccaaatag tgtaacagtt tttgcgctct   5340
gttttgtgac gataccattt ggaacagttg tggggtgtcg tcaataaaag tcgtccagta   5400
tgtaccctca ataaaaactg gattggtcaa aagagtcaat aggaagggaa tgttggtctt   5460
aacacctctg attctgaatt cgatcagggc acgaatcatc ttcctacgga cgatttcata   5520
agtagaacca gagcatgaac atttgaccag cattgagtcg tagtgaggcg agatagtagc   5580
acctgcataa gcgttaccac cgtccaatct cacaccatta ccaccggcag aacgatagac   5640
ctccaggcga ccggtatccg gttggaaatt cttagaggga tcttcagtgg taatacgaca   5700
ttggatggaa aacccacggg tggtgatttt atcctgtaat agacctagtt gagtcaaagt   5760
ggcacctgcg gcaatctgga tttgggcaga aacaatgtca ataccggtga tttcttcagt   5820
gatggtatgc tccacttgaa ttcttggatt aatttcaatg aaatagtgtc tgttttggtt   5880
gtcaaccaag aattcggcgg tacctgcgtt tctgtaacca cataccttag ctaatttaac   5940
agcatctgtc aaaatagcgt cacgaacttc acggggcaaa gtctttgctg gagcgacttc   6000
gacaactttt tggtgtcttc tttgcacaga acagtctctt tcgaaaagat gaaccacgtt   6060
tccgtggtta tcagccaaca attgaacttc aatatgcttt ggcttgtcca agaatctttc   6120
cacaaagcag gtaccattac cgaaggcagt acgggcttcg gaggtagcac gttgaaaggc   6180
atctgccacg tcgtcacctt ctctaacgac tctcatacct ctaccaccac caccaaaggc   6240
ggccttaatg atcaccgggt agccgtattc attaacgaag tcaagtgcct cttgcacagt   6300
ttcgataggt cctggagtac cgggaacggt aggaacgtta gctcttgctg ccaagtgtct   6360
ggcagagact ttgtcaccca cagagtcaat aacttcagct ggagggccga tccaagtgat   6420
accggccttc actactttgt cggcaaattc cgaattttca gacaagaacc cataacctgg   6480
atggatgaaa tccaccttat gcttctttgc aatttcgatg atctcgtcca ttgccaagta   6540
agcacccaca ggtgtatact ggccctcctc cccgataaca tacgcttcgt ccgccttcaa   6600
```

```
cctgtgcatt gaaagacggt cctcatggga gtatatggcg atggttctca tagacagctc   6660
atgagcagat ctaaaaattc taatcggaat ttcacctcta ttggcgacca agatcttatt   6720
cttttcgccg agcaaactga aattgtccct aagaccggcc aatttcttgc tactgctcat   6780
tctagatctt gttgttgttg ttgtcgttgt ttttgttttt gttgtgttag tataacgtgt   6840
ataattaaca gtggttgatt ctatactgtt aaatcggaag aaacggcaaa caagtcctct   6900
cagcaacatc aactggcaaa agacaaaacc cgccttttat agactccccg gagtgtcgaa   6960
atatgacttc ccggcaacga gttctccggg tggggtgata gcgggtcctt tcgctaccta   7020
tttttcgccc ccccccatcc tccatcctcc atgccccata ctccatgccc cctcgaggat   7080
ttacagtggg ggcctcactt ctcgcggact ctcttccaga aattgcacga ttacccaata   7140
tggtccttca ggagtgacac aacctgaaag gtggcggcgc aaaatgtatt ggcagagcct   7200
attggtggag cctattggga gcagctatag taaagaggag tagtagacag tagtagacaa   7260
tagtagggag tagttgaagg gtgtcaattt tgaatatcgt gagtgcatta actaactata   7320
gaagctaagt agcataaata aataaatata aatataaata tagatataaa tgtaggtgtg   7380
taaacgtgga cattgatgtt gccgttgcag caaggatccg tatcatttgt agcccacgcc   7440
acccggaaaa accaccattg tcctcagcag tccgccaaaa tatggatgcg ctcaatcaac   7500
tttccctccc ccgtcaatgc caaaaggata acgacacact attaagagcg catcatttgt   7560
aaaagccgag gaagggggat acgctaaccg gagacgtctc gcctcactct cggagctgag   7620
ccgccctcct taagaaattc atgggaagaa cacccttcgc ggcttctgaa cggctcgccc   7680
tcgtccattg gtcacctcac agtggcaact aataaggaca ttatagcaat agaaattaaa   7740
atggtgcaca gaaatacaat aggatcgaat aggataggat acaataagat acggaatatt   7800
agactatact gtgatacggt acggtacgat acgctacgat acgatacgat agaggatacc   7860
acggatataa cgtagtatta tttttcatta ttgggggttt ttttctgttt gaattttcca   7920
cgtcaagagt atcccatctg acaggaaccg atggactcgt cacagtacct atcgcccgag   7980
ttcaatccat ggacgcttcg ggtgaaggat cttcgtccgc tgttggcaag ccatgggatc   8040
agggcgtcgc caagggacag aaaggcggat cttgtacgtc tcttcaacac agagctgcgt   8100
ccgaaactta ctgagagtct taacaccaat aatcccaaaa acaacaacaa caatacagat   8160
actatagaca ctatagacac tatagacact actaacancc ctttaaagcg ccgccgatta   8220
agcaatgttg atgagccgtc aattccatat actcagctgg cggccgcgga tctgccggtc   8280
tccctatagt gagtcgtatt aatttcgata agccaggtta acctgcatta atgaatcggc   8340
caacgcgcgg ggagaggcgg tttgcgtatt gggcgctctt ccgcttcctc gctcactgac   8400
tcgctgcgct cggtcgttcg gctgcggcga gcggtatcag ctcactcaaa ggcggtaata   8460
cggttatcca cagaatcagg ggataacgca ggaaagaaca tgtgagcaaa aggccagcaa   8520
aaggccagga accgtaaaaa ggccgcgttg ctggcgtttt tccataggct ccgcccccct   8580
gacgagcatc acaaaaatcg acgctcaagt cagaggtggc gaaacccgac aggactataa   8640
agataccagg cgtttccccc tggaagctcc ctcgtgcgct ctcctgttcc gaccctgccg   8700
cttaccggat acctgtccgc ctttctccct tcgggaagcg tggcgctttc tcaatgctca   8760
cgctgtaggt atctcagttc ggtgtaggtc gttcgctcca agctgggctg tgtgcacgaa   8820
ccccccgttc agcccgaccg ctgcgcctta tccggtaact atcgtcttga gtccaacccg   8880
gtaagacacg acttatcgcc actggcagca gccactggta acaggattag cagagcgagg   8940
tatgtaggcg gtgctacaga gttcttgaag tggtggccta actacggcta cactagaagg   9000
```

```
acagtatttg gtatctgcgc tctgctgaag ccagttacct tcggaaaaag agttggtagc   9060
tcttgatccg gcaaacaaac caccgctggt agcggtggtt tttttgtttg caagcagcag   9120
attacgcgca gaaaaaaagg atctcaagaa gatcctttga tcttttctac ggggtctgac   9180
gctcagtgga acgaaaactc acgttaaggg attttggtca tgagattatc aaaaaggatc   9240
ttcacctaga tccttttaaa ttaaaaatga agttttaaat caatctaaag tatatatgag   9300
taaacttggt ctgacagtta ccaatgctta atcagtgagg cacctatctc agcgatctgt   9360
ctatttcgtt catccatagt tgcctgactc cccgtcgtgt agataactac gatacgggag   9420
ggcttaccat ctggccccag tgctgcaatg ataccgcgag acccacgctc accggctcca   9480
gatttatcag caataaacca gccagccgga agggccgagc gcagaagtgg tcctgcaact   9540
ttatccgcct ccatccagtc tattaattgt tgccgggaag ctagagtaag tagttcgcca   9600
gttaatagtt tgcgcaacgt tgttgccatt gctacaggca tcgtggtgtc acgctcgtcg   9660
tttggtatgg cttcattcag ctccggttcc caacgatcaa ggcgagttac atgatccccc   9720
atgttgtgca aaaaagcggt tagctccttc ggtcctccga tcgttgtcag aagtaagttg   9780
gccgcagtgt tatcactcat ggttatggca gcactgcata attctcttac tgtcatgcca   9840
tccgtaagat gcttttctgt gactggtgag tactcaacca agtcattctg agaatagtgt   9900
atgcggcgac cgagttgctc ttgcccggcg tcaatacggg ataataccgc gccacatagc   9960
agaactttaa aagtgctcat cattggaaaa cgttcttcgg ggcgaaaact ctcaaggatc  10020
ttaccgctgt tgagatccag ttcgatgtaa cccactcgtg cacccaactg atcttcagca  10080
tcttttactt tcaccagcgt ttctgggtga gcaaaaacag gaaggcaaaa tgccgcaaaa  10140
aagggaataa gggcgacacg gaaatgttga atactcatac tcttcctttt tcaatattat  10200
tgaagcattt atcagggtta ttgtctcatg agcggataca tatttgaatg tatttagaaa  10260
aataaacaaa taggggttcc gcgcacattt ccccgaaaag tgccacctga cgtctaagaa  10320
accattatta tcatgacatt aacctataaa aataggcgta tcacgaggcc ctttcgtctc  10380
gcgcgtttcg gtgatgacgg tgaaaacctc tgacacatgc agctcccgga gacggtcaca  10440
gcttgtctgt aagcggatgc cgggagcaga caagcccgtc agggcgcgtc agcgggtgtt  10500
ggcgggtgtc ggggctggct taactatgcg gcatcagagc agattgtact gagagtgcac  10560
catatggaca tattgtcgtt agaacgcggc tacaattaat acataacctt atgtatcata  10620
cacatacgat ttaggtgaca ctata                                        10645
```

<210> SEQ ID NO 6
<211> LENGTH: 12689
<212> TYPE: DNA
<213> ORGANISM: Artificial Sequence
<220> FEATURE:
<223> OTHER INFORMATION: DNA construct pMLV209

<400> SEQUENCE: 6

```
aaggaattac tggagttagt tgaagcatta ggtcccaaaa tttgtttact aaaaacacat     60
gtggatatct tgactgattt ttccatggag ggcacagtta agccgctaaa ggcattatcc    120
gccaagtaca attttttact cttcgaagac agaaaatttg ctgacattgg taatacagtc    180
aaattgcagt actctgcggg tgtatacaga atagcagaat gggcagacat tacgaatgca    240
cacggtgtgg tgggcccagg tattgttagc ggtttgaagc aggcggcaga agaagtaaca    300
aaggaaccta gaggcctttt gatgttagca gaattgtcat gcaagggctc cctatctact    360
```

-continued

```
ggagaatata ctaagggtac tgttgacatt gcgaagagcg acaaagattt tgttatcggc    420
tttattgctc aaagagacat gggtggaaga gatgaaggtt acgattggtt gattatgaca    480
cccggtgtgg gtttagatga caagggagac gcattgggtc aacagtatag aaccgtggat    540
gatgtggtct ctacaggatc tgacattatt attgttggaa gaggactatt tgcaaaggga    600
agggatgcta aggtagaggg tgaacgttac agaaaagcag gctgggaagc atatttgaga    660
agatgcggcc agcaaaacta aaaaactgta ttataagtaa atgcatgtat actaaactca    720
caaattagag cttcaattta attatatcag ttattaccca attctcatgt ttgacagctt    780
atcatcggat cgatccaata tcaaaggaaa tgatagcatt gaaggatgag actaatccaa    840
ttgaggagtg gcagcatata gaacagctaa agggtagtgc tgaaggaagc atacgatacc    900
ccgcatggaa tgggataata tcacaggagg tactagacta cctttcatcc tacataaata    960
gacgcatata agtacgcatt taagcataaa cacgcactat gccgttcttc tcatgtatat   1020
atatatacag gcaacacgca gatataggtg cgacgtgaac agtgagctgt atgtgcgcag   1080
ctcgcgttgc attttcggaa gcgctcgttt tcggaaacgc tttgaagttc ctattccgaa   1140
gttcctattc tctagctaga aagtatagga acttcagagc gcttttgaaa accaaaagcg   1200
ctctgaagac gcactttcaa aaaaccaaaa acgcaccgga ctgtaacgag ctactaaaat   1260
attgcgaata ccgcttccac aaacattgct caaaagtatc tctttgctat atatctctgt   1320
gctatatccc tatataacct acccatccac ctttcgctcc ttgaacttgc atctaaactc   1380
gacctctaca tttttatgt ttatctctag tattactctt tagacaaaaa aattgtagta   1440
agaactattc atagagtgaa tcgaaaacaa tacgaaaatg taaacatttc ctatacgtag   1500
tatatagaga caaaatagaa gaaaccgttc ataattttct gaccaatgaa gaatcatcaa   1560
cgctatcact ttctgttcac aaagtatgcg caatccacat cggtatagaa tataatcggg   1620
gatgccttta tcttgaaaaa atgcacccgc agcttcgcta gtaatcagta aacgcgggaa   1680
gtggagtcag gctttttta tggaagagaa aatagacacc aaagtagcct tcttctaacc   1740
ttaacggacc tacagtgcaa aaagttatca agagactgca ttatagagcg cacaaaggag   1800
aaaaaaagta atctaagatg ctttgttaga aaaatagcgc tctcgggatg catttttgta   1860
gaacaaaaaa gaagtataga ttctttgttg gtaaaatagc gctctcgcgt tgcatttctg   1920
ttctgtaaaa atgcagctca gattctttgt ttgaaaaatt agcgctctcg cgttgcattt   1980
ttgttttaca aaaatgaagc acagattctt cgttggtaaa atagcgcttt cgcgttgcat   2040
ttctgttctg taaaaatgca gctcagattc tttgtttgaa aaattagcgc tctcgcgttg   2100
catttttgtt ctacaaaatg aagcacagat gcttcgttaa caaagatatg ctattgaagt   2160
gcaagatgga aacgcagaaa atgaaccggg gatgcgacgt gcaagattac ctatgcaata   2220
gatgcaatag tttctccagg aaccgaaata catacattgt cttccgtaaa gcgctagact   2280
atatattatt atacaggttc aaatatacta tctgtttcag ggaaaactcc caggttcgga   2340
tgttcaaaat tcaatgatgg gtaacaagta cgatccgata tatgcggtgt gaaataccgc   2400
acagatgcgt aaggagaaaa taccgcatca ggcgccattc gccattcagg ctgcgcaact   2460
gttgggaagg gcgatcggtg cgggcctctt cgctattacg ccagctggcg aaagggggat   2520
gtgctgcaag gcgattaagt tgggtaacgc cagggttttc ccagtcacga cgttgtaaaa   2580
cgacggccag tggcggccgc ttaacaagaa tgggttggcg gactcgtcaa tggagagtac   2640
aatgccaaag ttctccttga ggttatttaa tcttccacag gttcaaggca ttctggcagc   2700
ttctcaattg ggaagttttc gtagatgata cggtaggtgg tggtaaatag tgggaactca   2760
```

```
tctgtcctgc ccatgttgga gaggaactcg taaacttccc tagttgtgtg gataccttga   2820
caggattggc cattcaacaa cttttcttca gcctccgttg cagagacaga atgttgtgcc   2880
atatatctac caactctaac gttacggccg ccggcacagg tagtgattag gtcggcaaca   2940
cctgcagatt catgagtaaa ggttgcagca tgacagccat cgaaaaaagt cttggcaaat   3000
tgaatggttt ccaccaaacc tattctcatg actgcagcct ttgcattatc accccaacct   3060
aaaccttcga caaatgatat cacctaataa cttcgtatag catacattat acgaagttat   3120
attaagggtt ctcgagaatt cttgctgcaa cggcaacatc aatgtccacg tttacacacc   3180
tacatttata tctatattta tatttatatt tatttattta tgctacttag cttctatagt   3240
tagttaatgc actcacgata ttcaaaattg acacccttca actactccct actattgtct   3300
actactgtct actactcctc tttactatag ctgctcccaa taggctccac caataggctc   3360
tgtcaataca ttttgcgccg ccacctttca ggttgtgtca ctcctgaagg accatattgg   3420
gtaatcgtgc aatttctgga agagagtgcc gcgagaagtg aggcccccac tgtaaatcct   3480
cgagggggca tggagtatgg ggcatggagg atggaggatg gggggggggg gggaaaatag   3540
gtagcgaaag gacccgctat caccccaccc ggagaactcg ttgccgggaa gtcatatttc   3600
gacactccgg ggagtctata aaaggcgggt tttgtctttt gccagttgat gttgctgaga   3660
ggacttgttt gccgtttctt ccgatttaac agtatagaat caaccactgt taattataca   3720
cgttatacta acacaacaaa aacaaaaaca acgacaacaa caacaacaat gcctgaactc   3780
accgcgacgt ctgtcgagaa gtttctgatc gaaaagttcg acagcgtctc cgacctgatg   3840
cagctctcgg agggcgaaga atctcgtgct ttcagcttcg atgtaggagg gcgtggatat   3900
gtcctgcggg taaatagctg cgccgatggt ttctacaaag atcgttatgt ttatcggcac   3960
tttgcatcgg ccgcgctccc gattccggaa gtgcttgaca ttggggaatt cagcgagagc   4020
ctgacctatt gcatctcccg ccgtgcacag ggtgtcacgt tgcaagacct gcctgaaacc   4080
gaactgcccg ctgttctgca gccggtcgcg gaggccatgg atgcgatcgc tgcggccgat   4140
cttagccaga cgagcgggtt cggcccattc ggaccgcaag gaatcggtca atacactaca   4200
tggcgtgatt tcatatgcgc gattgctgat ccccatgtgt atcactggca aactgtgatg   4260
gacgacaccg tcagtgcgtc cgtcgcgcag gctctcgatg agctgatgct ttgggccgag   4320
gactgccccg aagtccggca cctcgtgcac gcggatttcg gctccaacaa tgtcctgacg   4380
gacaatggcc gcataacagc ggtcattgac tggagcgagg cgatgttcgg ggattcccaa   4440
tacgaggtcg ccaacatctt cttctggagg ccgtggttgg cttgtatgga gcagcagacg   4500
cgctacttcg agcggaggca tccggagctt gcaggatcgc cgcggctccg ggcgtatatg   4560
ctccgcattg gtcttgacca actctatcag agcttggttg acggcaattt cgatgatgca   4620
gcttgggcgc agggtcgatg cgacgcaatc gtccgatccg gagccgggac tgtcgggcgt   4680
acacaaatcg cccgcagaag cgcggccgtc tggaccgatg gctgtgtaga agtactcgcc   4740
gatagtggaa accgacgccc cagcactcgt ccgagggcaa aggaatagag tagtaagctc   4800
aatgttgagc aaagcaggac gagaaaaaaa aaaataatga ttgttaagaa gttcatgaaa   4860
aaaaaaagga aaaatactca aatacttata acagagtgat taaataataa acggcagtat   4920
accctatcag gtattgagat agttttattt ttgtaggtat ataatctgaa gcctttgaac   4980
tattttctcg tatatatcat ggagtataca ttgcattagc aacattacat actaggatct   5040
ctagacctaa taacttcgta tagcatacat tatacgaagt tatattaagg gttgtcgacg   5100
```

-continued

```
gatcctgatg ctttactgtg atctctgata ctctctgata ctctttgata ctcttttcca   5160
tgcatgtttc gcttttccct cagctactgc ttcacctccc ctcccctccc ctctccccct   5220
tctttctccc gtttctgtgt acaacttctt tatagaccca ctaaccccca acactgtatt   5280
taacacatcc ccattgacct tcattgacct tcattgaccc tcccccaccc tttccctccc   5340
ccaccagcgt atttcccttt tctctcccca ttctctctgc tcttctcggc tcgttgtcgc   5400
tcgcggtcat ttttttttcgc ccttcttttc ccgcttttcc cgtagctggt gtagtccgaa   5460
actgtgctga tcttcttcct catatgggac catctgggta gagctcctct atttattatc   5520
cgaccctatt ccaccttcct tgcttggttg acaatttaag atgaagttcc tcccatttct   5580
tttgtactcc ttttctcctc tcttgtattt ttgtctcctt ttcttgtttc ttccctctgt   5640
aagccatcca aagaacagaa cccatctttc tcgtgctgct taaactaaac cgaacccaca   5700
cgcaatctta aaagaaccat taattaaatg acaagtgccg ctactgttac tgcttcgttc   5760
aacgatactt ttagcgtatc cgataatgtc gccgttattg ttcctgaaac ggacactcag   5820
gtgacctaca gggatctatc ccacatggtg ggtcacttcc agaccatgtt cacaaatcct   5880
aattctccat tgtacggagc tgttttcaga caagatacag tggcgatatc catgcgtaat   5940
gggctggaat ttatcgtcgc tttcctcggt gctactatgg acgctaaaat tggcgcgccc   6000
ttgaatccca attataagga aaaggagttc aatttttatt tgaatgacct gaaatctaag   6060
gcgatttgcg tcccaaaggg taccacaaag ttacagagtt ctgaaattct aaaatctgcc   6120
tccacgtttg gatgttttat cgtagagctg gccttcgatg cgaccaggtt tagggtagag   6180
tatgatatat actctccaga ggacaactac aaaagggtta tttaccggtc tttgaacaac   6240
gccaaatttg tcaacacaaa tcccgttaaa ttccctgggt ttgcccgttc cagtgacgtt   6300
gccctgattt tgcataccag tggtaccacc tccactccaa aaacggtgcc tttgttacat   6360
ttgaacattg tgagaagcac gttgaacatt gctaacactt acaagctaac gcccttggac   6420
agatcttatg tcgtgatgcc tcttttccac gtccatgggt taattggtgt tttactttcc   6480
acttttagaa ctcagggttc tgttgtggtt cccgatggat tccatccaaa gttattctgg   6540
gaccaatttg ttaagtacaa ctgtaattgg ttcagttgcg ttcccacaat aagcatgatt   6600
atgctgaaca tgcccaaacc aaacccttc ccacacatta gattcatcag atcgtgttct   6660
tctgctttgg ctccagcaac gttccataag ctggagaagg aattcaatgc acctgtcttg   6720
gaggcctatg cgatgaccga agcatcacat caaatgacct caaacaatct gcctccagga   6780
aagagaaagc ctggtactgt gggccagcca caaggagtca ccgtcgtcat tctagatgac   6840
aatgacaatg tcttgccccc gggcaaagtc ggcgaagttt ccatcagagg cgaaaacgtc   6900
actttggggt atgctaataa tccaaaagct aacaaggaga acttcaccaa gagagagaac   6960
tatttcagaa ccggtgacca aggttatttc gaccctgagg ggtttttggt ccttacaggc   7020
agaatcaaag agcttatcaa caggggtggt gaaaagattt cacccattga gctcgacggc   7080
attatgctat cgcatccaaa gatcgatgaa gccgttgcat ttggtgttcc cgacgatatg   7140
tacggccaag tagttcaagc cgccattgtt ttgaagaagg gagaaaaaat gacctacgaa   7200
gaactggtga acttcttaaa gaagcaccta gcctctttca aaattccaac caaggtgtac   7260
tttgttgata agctaccaaa aaccgctaca ggtaaaatcc agagaagagt tatcgcagaa   7320
acttttgcta agagcagcag aaataagtag ttaattaagc gatttaaatc tctaattatt   7380
agttaaagtt ttataagcat ttttatgtaa cgaaaaataa attggttcat attattactg   7440
cactgtcact taccatggaa agaccagaca agaagttgcc gacagtctgt tgaattggcc   7500
```

```
tggttaggct taagtctggg tccgcttctt tacaaatttg gagaatttct cttaaacgat   7560
atgtatattc ttttcgttgg aaaagatttc ttccaaaaaa aaaaccgatg aattagtgga   7620
accaaggaaa aaaaaagagg tatccttgat taaggaacac tgtttaaaca gtgtggtttc   7680
caaaaccctg aaactgcatt agtgtaatac aagactagac acctcgatac aaataatggt   7740
tactcaattc aaaactgcct ttgaaacatc atgaaaactg tttcaccctc tgtgaagcat   7800
aaacactaga aagccaatga agagctctac aagcctcata tgggttcaat gggtctgcaa   7860
tgaccgcata cgggcttgga caattacctt ctattgaatt tctgagaaga gatacatctg   7920
accagcaatg taagcagaca atcccaattc tgtaaacaac ctctttgtcc ataattcccc   7980
atcagaagag tgaaaaatgc cctcaaaatg catgcgccac tcccacctct caactgcact   8040
gcgccacctc tgagggtcct ttcaggggtc gactaccccg gacacctcgc agaggagcga   8100
ggtcacgtac ttttaaaatg gcagagacgc gcagtttctt gaagaaagga taaaaatgaa   8160
atggtgcgga aatgcgaaaa tgatgaaaaa ttttcttggt ggcgaggaaa ttgagtgcaa   8220
taattggcac gaggttgttg ccacccgagt gtgagtatat atcctagttt ctgcactttt   8280
cttcttcttt tctttgcgtt ttcttttcaa cttttttta ctttttcctt caacagacaa   8340
atctaactta tatagatcta tgtccattgc tatagttggt gctggtgcta ttggtggtta   8400
tttgggtgtt agattggctg aagctggtga agatgttact ttcattgcta gatcaaacgc   8460
tgctgctatt caagctgatg gtatgagatt gattgaagaa gatggtactg aaatccactc   8520
caagtctgtt aaggctacta gatcaatgca agaagctggt gttcatgaag ttgttttgtt   8580
gactgttaag gcccatcaag ttggtccaat tgctgctgac ttgcatcatt tgattggtcc   8640
agatactgtt gttgtcacta tgcaaaatgg tattccttgg tggtatttct tgggtggtta   8700
ttctggtgat catgctggta ctagattgga atctgctgat ccaggtggtt tgattgctga   8760
tcacttagat ccaaaacacg ttatcggttc tgttgtttat ccagctactg ttttgactga   8820
tccaggtact gttaaggtta tcgaaggtaa tagattcggt ttgggtgaat tggatggttc   8880
caaatctgaa agagttttgg ccttgtctca aagattggct agagctggtt ttagagcacc   8940
agttacatct gatattagag ccgaaatttg gttgaagttg tggggtaatt tgtccttcaa   9000
tccaatttct gctttgaccc atgctacctt ggaagatata tgtagatttc cagataccag   9060
agctattgct gctgaaatga tgagagaagc tgaagttatt gctaacaagt tgggtgttac   9120
tttcagattg ggtatcgata agagaattgc tggtgctgaa aaagttggtc cacataagac   9180
ttctatgttg caagatgttg aagccggtag accaattgaa ttggaagctt tggttggttc   9240
cgttatcgaa ttgggtagat tgactggtac tccaactcca catattgata ctgttttcgc   9300
cttgatgaga ttattggccc aatctttgga aagagcacaa ggtagattgg ctattcaagg   9360
tgcttaaaga tctgttaatt caaattaatt gatatagttt tttaatgagt attgaatctg   9420
tttagaaata atggaatatt atttttattt atttatttat attattggtc ggctcttttc   9480
ttctgaaggt caatgacaaa atgatatgaa ggaaataatg atttctaaaa ttttacaacg   9540
taagatattt ttacaaaagc ctagctcatc ttttgtcatg cactatttta ctcacgcttg   9600
aaattaacgg ccagtccact gcggagtcat ttcaaagtca tcctaatcga tctatcgttt   9660
ttgatagctc attgagatga tatcggatcc attcttggta aaaattggtg aggaatatta   9720
aagacaatca agtctgagcc tgcacaagcc tcaacaatgt ctggaactgc aacaacgtta   9780
actggcaact tgatacctgg caagtacttg acgttttcgt gtttggtatt tatgatttca   9840
```

```
gtcaactttt cgccttcaat caattcttca tagacccaca tattaacatc tctttgaaat   9900
tgacgaggtc tctcaacggt gttttccgct ataaccttgg caattgtaca cccccagtta   9960
ccggaaccaa caaccgtcac cttgaacgga tgttccggat agtcttctgg ttgtaatgat  10020
gtagaatctt ttctgtttgg cttgattgtg gacgcaatag tagataatct ttcagcaggg  10080
gacaccagcg gccgctggcg taatcatggt catagctgtt tcctgtgtga aattgttatc  10140
cgctcacaat tccacacaac atacgagccg gaagcataaa gtgtaaagcc tggggtgcct  10200
aatgagtgag ctaactcaca ttaattgcgt tgcgctcact gcccgctttc cagtcgggaa  10260
acctgtcgtg ccagctgcat taatgaatcg gccaacgcgc ggggagaggc ggtttgcgta  10320
ttgggcgctc ttccgcttcc tcgctcactg actcgctgcg ctcggtcgtt cggctgcggc  10380
gagcggtatc agctcactca aaggcggtaa tacggttatc cacagaatca ggggataacg  10440
caggaaagaa catgtgagca aaaggccagc aaaaggccag gaaccgtaaa aaggccgcgt  10500
tgctggcgtt tttccatagg ctccgccccc ctgacgagca tcacaaaaat cgacgctcaa  10560
gtcagaggtg gcgaaacccg acaggactat aaagatacca ggcgtttccc cctggaagct  10620
ccctcgtgcg ctctcctgtt ccgaccctgc cgcttaccgg atacctgtcc gcctttctcc  10680
cttcgggaag cgtggcgctt tctcatagct cacgctgtag gtatctcagt tcggtgtagg  10740
tcgttcgctc caagctgggc tgtgtgcacg aaccccccgt tcagcccgac cgctgcgcct  10800
tatccggtaa ctatcgtctt gagtccaacc cggtaagaca cgacttatcg ccactggcag  10860
cagccactgg taacaggatt agcagagcga ggtatgtagg cggtgctaca gagttcttga  10920
agtggtggcc taactacggc tacactagaa ggacagtatt tggtatctgc gctctgctga  10980
agccagttac cttcggaaaa agagttggta gctcttgatc cggcaaacaa accaccgctg  11040
gtagcggtgg tttttttgtt tgcaagcagc agattacgcg cagaaaaaaa ggatctcaag  11100
aagatccttt gatcttttct acggggtctg acgctcagtg gaacgaaaac tcacgttaag  11160
ggattttggt catgagatta tcaaaaagga tcttcaccta gatcctttta aattaaaaat  11220
gaagttttaa atcaatctaa agtatatatg agtaaacttg gtctgacagt taccaatgct  11280
taatcagtga ggcacctatc tcagcgatct gtctatttcg ttcatccata gttgcctgac  11340
tccccgtcgt gtagataact acgatacggg agggcttacc atctggcccc agtgctgcaa  11400
tgataccgcg agacccacgc tcaccggctc cagatttatc agcaataaac cagccagccg  11460
gaagggccga gcgcagaagt ggtcctgcaa ctttatccgc ctccatccag tctattaatt  11520
gttgccggga agctagagta agtagttcgc cagttaatag tttgcgcaac gttgttgcca  11580
ttgctacagg catcgtggtg tcacgctcgt cgtttggtat ggcttcattc agctccggtt  11640
cccaacgatc aaggcgagtt acatgatccc ccatgttgtg caaaaaagcg gttagctcct  11700
tcggtcctcc gatcgttgtc agaagtaagt tggccgcagt gttatcactc atggttatgg  11760
cagcactgca taattctctt actgtcatgc catccgtaag atgcttttct gtgactggtg  11820
agtactcaac caagtcattc tgagaatagt gtatgcggcg accgagttgc tcttgcccgg  11880
cgtcaatacg ggataatacc gcgccacata gcagaacttt aaaagtgctc atcattggaa  11940
aacgttcttc ggggcgaaaa ctctcaagga tcttaccgct gttgagatcc agttcgatgt  12000
aacccactcg tgcacccaac tgatcttcag catcttttac tttcaccagc gtttctgggt  12060
gagcaaaaac aggaaggcaa aatgccgcaa aaaagggaat aagggcgaca cggaaatgtt  12120
gaatactcat actcttcctt tttcaatatt attgaagcat ttatcagggt tattgtctca  12180
tgagcggata catatttgaa tgtatttaga aaaataaaca aataggggtt ccgcgcacat  12240
```

```
ttccccgaaa agtgccacct gacgtctaag aaaccattat tatcatgaca ttaacctata  12300

aaaataggcg tatcacgagg ccctttcgtc ttcaagaatt agcttttcaa ttcaattcat  12360

catttttttt ttattctttt ttttgatttc ggtttctttg aaattttttt gattcggtaa  12420

tctccgaaca gaaggaagaa cgaaggaagg agcacagact tagattggta tatatacgca  12480

tatgtagtgt tgaagaaaca tgaaattgcc cagtattctt aacccaactg cacagaacaa  12540

aaacatgcag gaaacgaaga taaatcatgt cgaaagctac atataaggaa cgtgctgcta  12600

ctcatcctag tcctgttgct gccaagctat ttaatatcat gcacgaaaag caaacaaact  12660

tgtgtgcttc attggatgtt cgtaccacc                                   12689
```

<210> SEQ ID NO 7
<211> LENGTH: 8454
<212> TYPE: DNA
<213> ORGANISM: Artificial Sequence
<220> FEATURE:
<223> OTHER INFORMATION: DNA construct pMIPk114
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (5165)..(5165)
<223> OTHER INFORMATION: n is a, c, g, or t

<400> SEQUENCE: 7

```
aattcttgct gcaacggcaa catcaatgtc cacgtttaca cacctacatt tatatctata     60

tttatattta tatttattta tttatgctac ttagcttcta tagttagtta atgcactcac    120

gatattcaaa attgacaccc ttcaactact ccctactatt gtctactact gtctactact    180

cctctttact atagctgctc ccaataggct ccaccaatag gctctgtcaa tacattttgc    240

gccgccacct ttcaggttgt gtcactcctg aaggaccata ttgggtaatc gtgcaatttc    300

tggaagagag tgccgcgaga agtgaggccc ccactgtaaa tcctcgaggg ggcatggagt    360

atggggcatg naggatggag gatggggggg ggggggggaaa ataggtagcg aaaggacccg    420

ctatcacccc acccggagaa ctcgttgccg ggaagtcata tttcgacact ccggggagtc    480

tataaaaggc gggttttgtc ttttgccagt tgatgttgct gagaggactt gtttgccgtt    540

tcttccgatt taacagtata gaatcaacca ctgttaatta tacacgttat actaacacaa    600

caaaaacaaa aacaacgaca acaacaacaa caatgtttgc tttctacttt ctcaccgcat    660

gcaccacttt gaagggtgtt ttcggagttt ctccgagtta caatggtctt ggtctcaccc    720

cacagatggg ttgggacagc tggaatacgt ttgcctgcga tgtcagtgaa cagctacttc    780

tagacactgc tgatagaatt tctgacttgg ggctaaagga tatgggttac aagtatgtca    840

tcctagatga ctgttggtct agcggcaggg attccgacgg tttcctcgtt gcagacaagc    900

acaaatttcc caacggtatg ggccatgttg cagaccacct gcataataac agctttcttt    960

tcggtatgta ttcgtctgct ggtgagtaca cctgtgctgg gtaccctggg tctctggggc   1020

gtgaggaaga agatgctcaa ttctttgcaa ataaccgcgt tgactacttg aagtatgata   1080

attgttacaa taaaggtcaa tttggtacac cagacgtttc ttaccaccgt tacaaggcca   1140

tgtcagatgc tttgaataaa actggtaggc ctattttcta ttctctatgt aactggggtc   1200

aggatttgac attttactgg ggctctggta tcgccaattc ttggagaatg agcggagata   1260

ttactgctga gttcacccgt ccagatagca gatgtccctg tgacggtgac gaatatgatt   1320
```

-continued

```
gcaagtacgc cggtttccat tgttctatta tgaatattct taacaaggca gctccaatgg   1380
ggcaaaatgc aggtgttggt ggttggaacg atctggacaa tctagaggtc ggagtcggta   1440
atttgactga cgatgaggaa aaggcccatt tctctatgtg ggcaatggta aagtccccac   1500
ttatcattgg tgccgacgtg aatcacttaa aggcatcttc gtactcgatc tacagtcaag   1560
cctctgtcat cgcaattaat caagatccaa agggtattcc agccacaaga gtctggagat   1620
attatgtttc agacaccgat gaatatggac aaggtgaaat tcaaatgtgg agtggtccgc   1680
ttgacaatgg tgaccaagtg gttgctttat tgaatggagg aagcgtagca agaccaatga   1740
acacgacctt ggaagagatt ttctttgaca gcaatttggg ttcaaaggaa ctgacatcga   1800
cttgggatat ttacgactta tgggccaaca gagttgacaa ctctacggcg tctgctatcc   1860
ttgaacagaa taaggcagcc accggtattc tctacaatgc tacagagcag tcttataaag   1920
acggtttgtc taagaatgat acaagactgt ttggccagaa aattggtagt ctttctccaa   1980
atgctatact taacacaact gttccagctc atggtatcgc cttctatagg ttgagaccct   2040
cggcttaagc tcaatgttga gcaaagcagg acgagaaaaa aaaaaataat gattgttaag   2100
aagttcatga aaaaaaaaag gaaaaatact caaatactta taacagagtg attaaataat   2160
aaacggcagt ataccctatc aggtattgag atagttttat ttttgtaggt atataatctg   2220
aagcctttga actattttct cgtatatatc atggagtata cattgcatta gcaacattac   2280
atactaggat ctctagacct aataacttcg tatagcatac attatacgaa gttatattaa   2340
gggttgtcga cgatatggat atggatatgg atatggagat gaatttgaat ttagatttgg   2400
gtcttgattt ggggttggaa ttaaaagggg ataacaatga gggttttcct gttgatttaa   2460
acaatggacg tgggaggtga ttgatttaac ctgatccaaa aggggtatgt ctatttttta   2520
gagagtgttt ttgtgtcaaa ttatggtaga atgtgtaaag tagtataaac tttcctctca   2580
aatgacgagg tttaaaacac cccccgggtg agccgagccg agaatggggc aattgttcaa   2640
tgtgaaatag aagtatcgag tgagaaactt gggtgttggc cagccaaggg ggggggggaa   2700
ggaaaatggc gcgaatgctc aggtgagatt gttttggaat tgggtgaagc gaggaaatga   2760
gcgacccgga ggttgtgact ttagtggcgg aggaggacgg aggaaaagcc aagagggaag   2820
tgtatataag gggagcaatt tgccaccagg atagaattgg atgagttata attctactgt   2880
atttattgta taatttattt ctccttttgt atcaaacaca ttacaaaaca cacaaaacac   2940
acaaacaaac acaattacaa aaattaatta aaaaatgaag gttgacaccc cagactccgc   3000
ttctactatt tctatgacta acaccattac catcaccgtt gaacaagatg gtatctacga   3060
aatcaatggt gctagacaag aaccagttgt caacttgaat atggttactg gtgcttccaa   3120
gttgagaaag caattgagag aaactaacga attattggtt tgcccaggtg tttacgatgg   3180
tttgtctgct agaattgcta tcaacttggg tttcaagggt atgtatatga ctggtgctgg   3240
tactactgct tcaagattgg gtatggctga tttgggtttg gctcatatct atgacatgaa   3300
gactaacgct gaaatgattg ctaatttgga cccatacggt ccacctttga ttgctgatat   3360
ggatacaggt tatggtggtc cattgatggt tgctagatct gtccaacaat atattcaagc   3420
tggtgttgcc ggtttccata tcgaagatca aattcaaaac aagagatgcg gtcatttggc   3480
tggtaaaaga gttgttacta tggacgaata cttgaccaga attagagctg ctaagttgac   3540
caaggataga ttgagatctg acatcgtttt gattgcaaga actgatgcct tgcaacaaca   3600
tggttacgat gaatgcatta gaagattgaa ggctgctaga gatttgggtg ctgatgttgg   3660
tttgttggaa ggtttcactt ctaaagaaat ggccagaaga tgcgttcaag atttggctcc   3720
```

```
atggcctttg ttgttgaaca tggttgaaaa tggtgcaggt ccagttatct ctgttgatga   3780
agctagagaa atgggtttca gaattatgat tttctccttc gcttgtatta ccccagctta   3840
catgggtatt actgctgctt tggaaagatt gaaaaaggat ggtgttgtag gtttgccaga   3900
aggtatgggt cctaaaaagt tgtttgaagt ttgcggtttg atggactccg ttagagttga   3960
tactgaagct ggtggtgatg gttttgctaa cggtgtttga ttaattaacc catgtctcta   4020
ctggtggtgg tgcttctttg gaattattgg aaggtaagga attgccaggt gttgctttct   4080
tatccgaaaa gaaataaatt gaattgaatt gaaatcgata gatcaatttt tttcttttct   4140
ctttccccat cctttacgct aaaataatag tttattttat tttttgaata tttttttattt   4200
atatacgtat atatagacta ttatttatct tttaatgatt attaagattt ttattaaaaa   4260
aaaattcgct cctcttttaa tgcctttatg cagttttttt ttcccattcg atatttctat   4320
gttcgggttc agcgtatttt aagtttaata actcgaaaat tctgcgttcg ttaagtcgac   4380
ggatccgtat catttgtagc ccacgccacc cggaaaaacc accattgtcc tcagcagtcc   4440
gccaaaatat ggatgcgctc aatcaacttt ccctcccccg tcaatgccaa aaggataacg   4500
acacactatt aagagcgcat catttgtaaa agccgaggaa gggggatacg ctaaccggag   4560
acgtctcgcc tcactctcgg agctgagccg ccctccttaa gaaattcatg ggaagaacac   4620
ccttcgcggc ttctgaacgg ctcgccctcg tccattggtc acctcacagt ggcaactaat   4680
aaggacatta tagcaataga aattaaaatg gtgcacagaa atacaatagg atcgaatagg   4740
ataggataca ataagatacg gaatattaga ctatactgtg atacggtacg gtacgatacg   4800
ctacgatacg atacgataga ggataccacg gatataacgt agtattattt ttcattattg   4860
ggggtttttt tctgtttgaa ttttccacgt caagagtatc ccatctgaca ggaaccgatg   4920
gactcgtcac agtacctatc gcccgagttc aatccatgga cgcttcgggt gaaggatctt   4980
cgtccgctgt tggcaagcca tgggatcagg gcgtcgccaa gggacagaaa ggcggatctt   5040
gtacgtctct tcaacacaga gctgcgtccg aaacttactg agagtcttaa caccaataat   5100
cccaaaaaca acaacaacaa tacagatact atagacacta tagacactat agacactact   5160
aacanccctt taaagcgccg ccgattaagc aatgttgatg agccgtcaat tccatatact   5220
ctgcagcgta cgaagcttca gctggcggcc gcgttctata gtgtcaccta aatcgtatgt   5280
gtatgataca taaggttatg tattaattgt agccgcgttc taacgacaat atgtccatat   5340
ggtgcactct cagtacaatc tgctctgatg ccgcatagtt aagccagccc cgacacccgc   5400
caacacccgc tgacgcgccc tgacgggctt gtctgctccc ggcatccgct tacagacaag   5460
ctgtgaccgt ctccgggagc tgcatgtgtc agaggttttc accgtcatca ccgaaacgcg   5520
cgagacgaaa gggcctcgtg atacgcctat ttttataggt taatgtcatg ataataatgg   5580
tttcttagac gtcaggtggc acttttcggg gaaatgtgcg cggaacccct atttgtttat   5640
ttttctaaat acattcaaat atgtatccgc tcatgagaca ataaccctga taaatgcttc   5700
aataatattg aaaaaggaag agtatgagta ttcaacattt ccgtgtcgcc cttattccct   5760
tttttgcggc attttgcctt cctgtttttg ctcacccaga aacgctggtg aaagtaaaag   5820
atgctgaaga tcagttgggt gcacgagtgg gttacatcga actggatctc aacagcggta   5880
agatccttga gagttttcgc cccgaagaac gttttccaat gatgagcact tttaaagttc   5940
tgctatgtgg cgcggtatta tcccgtattg acgccgggca agagcaactc ggtcgccgca   6000
tacactattc tcagaatgac ttggttgagt actcaccagt cacagaaaag catcttacgg   6060
```

-continued

```
atggcatgac agtaagagaa ttatgcagtg ctgccataac catgagtgat aacactgcgg   6120
ccaacttact tctgacaacg atcggaggac cgaaggagct aaccgctttt ttgcacaaca   6180
tgggggatca tgtaactcgc cttgatcgtt gggaaccgga gctgaatgaa gccataccaa   6240
acgacgagcg tgacaccacg atgcctgtag caatggcaac aacgttgcgc aaactattaa   6300
ctggcgaact acttactcta gcttcccggc aacaattaat agactggatg gaggcggata   6360
aagttgcagg accacttctg cgctcggccc ttccggctgg ctggtttatt gctgataaat   6420
ctggagccgg tgagcgtggg tctcgcggta tcattgcagc actggggcca gatggtaagc   6480
cctcccgtat cgtagttatc tacacgacgg ggagtcaggc aactatggat gaacgaaata   6540
gacagatcgc tgagataggt gcctcactga ttaagcattg gtaactgtca gaccaagttt   6600
actcatatat actttagatt gatttaaaac ttcattttta atttaaaagg atctaggtga   6660
agatcctttt tgataatctc atgaccaaaa tcccttaacg tgagttttcg ttccactgag   6720
cgtcagaccc cgtagaaaag atcaaaggat cttcttgaga tccttttttt ctgcgcgtaa   6780
tctgctgctt gcaaacaaaa aaaccaccgc taccagcggt ggtttgtttg ccggatcaag   6840
agctaccaac tctttttccg aaggtaactg gcttcagcag agcgcagata ccaaatactg   6900
tccttctagt gtagccgtag ttaggccacc acttcaagaa ctctgtagca ccgcctacat   6960
acctcgctct gctaatcctg ttaccagtgg ctgctgccag tggcgataag tcgtgtctta   7020
ccgggttgga ctcaagacga tagttaccgg ataaggcgca gcggtcgggc tgaacggggg   7080
gttcgtgcac acagcccagc ttggagcgaa cgacctacac cgaactgaga tacctacagc   7140
gtgagcattg agaaagcgcc acgcttcccg aagggagaaa ggcggacagg tatccggtaa   7200
gcggcagggt cggaacagga gagcgcacga gggagcttcc agggggaaac gcctggtatc   7260
tttatagtcc tgtcgggttt cgccacctct gacttgagcg tcgatttttg tgatgctcgt   7320
caggggggcg gagcctatgg aaaaacgcca gcaacgcggc ctttttacgg ttcctggcct   7380
tttgctggcc ttttgctcac atgttctttc ctgcgttatc ccctgattct gtggataacc   7440
gtattaccgc ctttgagtga gctgataccg ctcgccgcag ccgaacgacc gagcgcagcg   7500
agtcagtgag cgaggaagcg gaagagcgcc caatacgcaa accgcctctc cccgcgcgtt   7560
ggccgattca ttaatgcagg ttaacctggc ttatcgaaat taatacgact cactataggg   7620
agaccggcag atccgcggcc gcaatagaga gtgacctatc caagctttgg gggtctaagt   7680
tttaatggcc agggaatca ttactttttt ttctcaatcc ttgatggata aaagtattac   7740
atacgtacag gattgtgtat tagtgtattt cgttatatga ttaaacaaag tttatagatt   7800
gtaaagtaga cgtaaagttt agtaattcat tttaatgttc attttacatt cagatgtcat   7860
taagcggctt tagagttgat ttcatcagat aatttagctt gagcaaccaa gatttctgga   7920
gcatcgaatt catccaagaa taattcaatg actctaatct tatcttcctt gttgaatgct   7980
tcatccttca tcaaagcgtc caagtcctta gcggatttaa caacatggtt ttcatattgg   8040
gtcttgtcag caaagagctt caataacaat tggtgatccc atggttgaat ttggttgtag   8100
tcctcatgac gaccgtggat caacttttcg atagtgtaac ctctgttgtt taagatgaag   8160
atgtatggct tgatgttcca tcttgcagca tctgagattg attggacagt caattgtaaa   8220
gaaccatcac caataaacaa aacagttctt ctttcttgtt cgccagtttg tttgtgtgca   8280
tcttcagcag caaatgcagc accaactgca gctggtaagg agaaaccaat ggaaccccat   8340
aagacttggg agatagactt tgaatctctt ggtatgggta gccaagacta gtcgatatca   8400
cctaataact tcgtatagca tacattatac gaagttatat taagggttct cgag         8454
```

<210> SEQ ID NO 8
<211> LENGTH: 11903
<212> TYPE: DNA
<213> ORGANISM: Artificial Sequence
<220> FEATURE:
<223> OTHER INFORMATION: DNA construct pMIPk120
<220> FEATURE:
<221> NAME/KEY: misc_feature
<222> LOCATION: (1168)..(1168)
<223> OTHER INFORMATION: n is a, c, g, or t
<220> FEATURE:
<221> NAME/KEY: misc_feature
<222> LOCATION: (9456)..(9456)
<223> OTHER INFORMATION: n is a, c, g, or t

<400> SEQUENCE: 8

```
gaacgcggcc gcgagctcta agttttaatg gcccagggaa tcattacttt tttttctcaa      60
tccttgatgg ataaaagtat tacatacgta caggattgtg tattagtgta tttcgttata     120
tgattaaaca aagtttatag attgtaaagt agacgtaaag tttagtaatt cattttaatg     180
ttcattttac attcagatgt cattaagcgg ctttagagtt gatttcatca gataatttag     240
cttgagcaac caagatttct ggagcatcga attcatccaa gaataattca atgactctaa     300
tcttatcttc cttgttgaat gcttcatcct tcatcaaagc gtccaagtcc ttagcggatt     360
taacaacatg gttttcatat tgggtcttgt cagcaaagag cttcaataac aattggtgat     420
cccatggttg aatttggttg tagtcctcat gacgaccgtg gatcaacttt tcgatagtgt     480
aacctctgtt gtttaagatg aagatgtatg gcttgatgtt ccatcttgca gcatctgaga     540
ttgattggac agtcaattgt aaagaaccat caccaataaa caaaacagtt cttctttctt     600
gttcgccagt ttgtttgtgt gcatcttcag cagcaaatgc agcaccaact gcagctggta     660
aggagaaacc aatggaaccc cataagactt gggagataga ctttgaatct cttggtatgg     720
gtagccaaga ctagtcgata tcacctaata acttcgtata gcatacatta tacgaagtta     780
tattaagggt tctcgagaat tcttgctgca acggcaacat caatgtccac gtttacacac     840
ctacatttat atctatattt atatttatat ttatttattt atgctactta gcttctatag     900
ttagttaatg cactcacgat attcaaaatt gacacccttc aactactccc tactattgtc     960
tactactgtc tactactcct ctttactata gctgctccca ataggctcca ccaataggct    1020
ctgtcaatac attttgcgcc gccacctttc aggttgtgtc actcctgaag gaccatattg    1080
ggtaatcgtg caatttctgg aagagagtgc cgcgagaagt gaggccccca ctgtaaatcc    1140
tcgagggggc atggagtatg ggcatgnag gatggaggat gggggggggg ggggaaaata    1200
ggtagcgaaa ggacccgcta tcaccccacc cggagaactc gttgccggga agtcatattt    1260
cgacactccg gggagtctat aaaaggcggg ttttgtcttt tgccagttga tgttgctgag    1320
aggacttgtt tgccgtttct tccgatttaa cagtatagaa tcaaccactg ttaattatac    1380
acgttatact aacacaacaa aaacaaaaac aacgacaaca acaacaacaa tgcctgaact    1440
caccgcgacg tctgtcgaga agtttctgat cgaaaagttc gacagcgtct ccgacctgat    1500
gcagctctcg gagggcgaag aatctcgtgc tttcagcttc gatgtaggag ggcgtggata    1560
tgtcctgcgg gtaaatagct gcgccgatgg tttctacaaa gatcgttatg tttatcggca    1620
ctttgcatcg gccgcgctcc cgattccgga agtgcttgac attggggaat tcagcgagag    1680
cctgacctat tgcatctccc gccgtgcaca gggtgtcacg ttgcaagacc tgcctgaaac    1740
cgaactgccc gctgttctgc agccggtcgc ggaggccatg gatgcgatcg ctgcggccga    1800
```

-continued

```
tcttagccag acgagcgggt tcggcccatt cggaccgcaa ggaatcggtc aatacactac   1860
atggcgtgat ttcatatgcg cgattgctga tccccatgtg tatcactggc aaactgtgat   1920
ggacgacacc gtcagtgcgt ccgtcgcgca ggctctcgat gagctgatgc tttgggccga   1980
ggactgcccc gaagtccggc acctcgtgca cgcggatttc ggctccaaca atgtcctgac   2040
ggacaatggc cgcataacag cggtcattga ctggagcgag gcgatgttcg gggattccca   2100
atacgaggtc gccaacatct tcttctggag gccgtggttg gcttgtatgg agcagcagac   2160
gcgctacttc gagcggaggc atccggagct tgcaggatcg ccgcggctcc gggcgtatat   2220
gctccgcatt ggtcttgacc aactctatca gagcttggtt gacggcaatt tcgatgatgc   2280
agcttgggcg cagggtcgat gcgacgcaat cgtccgatcc ggagccggga ctgtcgggcg   2340
tacacaaatc gcccgcagaa gcgcggccgt ctggaccgat ggctgtgtag aagtactcgc   2400
cgatagtgga aaccgacgcc ccagcactcg tccgagggca aaggaataga gtagtaagct   2460
caatgttgag caaagcagga cgagaaaaaa aaaaataatg attgttaaga agttcatgaa   2520
aaaaaaaagg aaaaatactc aaatacttat aacagagtga ttaaataata aacggcagta   2580
taccctatca ggtattgaga tagttttatt tttgtaggta tataatctga agcctttgaa   2640
ctattttctc gtatatatca tggagtatac attgcattag caacattaca tactaggatc   2700
tctagaccta ataacttcgt atagcataca ttatacgaag ttatattaag ggttgtcgac   2760
accatcctag aacttcaatt caccacgttc agggtaatat attttaaccg ccgacgttct   2820
cgccataact tttaaacagt gataactagt attgaaactt agaagagaaa agggtaaagt   2880
taatgcttaa tcttgtcttg gcttaaaaag taatatgtac ttatttacgt cttcacaaaa   2940
tctagcagaa aaacggtagt atttatgtat attcaaaaaa aaatcattat cctcatcaag   3000
attgctttat gtttaaacct attttggggt aacttttgtg taagtgctaa ctgtttgcag   3060
tagaccgtcc tctacgttgt aaagcagacc gtatacctgt aattctccat tttgtacagc   3120
agtttgcaca gtagggtttt caataatcct attaaactgc cttttgacgt tacagtgcga   3180
caggtaatga gatttttcac gttgcgtttt caaatggatc aaattttgtg actcttcatg   3240
gtacatggtg tcaatatcgt ctaagtactt gtacagatga gaacagttaa cttttggtaa   3300
ggcttccctt tggttagtta aacatgtctt tataccacca caatcagtgt ggccacaaat   3360
aataactttg ttaactttta gacaaataat ggcaaactct aaagtggcct tcaaagttaa   3420
atcctctgag tgacatatgt tagcaacatt tttccaagtg aacacttcgc cgggcaagac   3480
acctaaacag ttttcgttgt aacgcgaatc ggagcagccg atgaaaagag tgtgagggga   3540
ctggcccttc gcattgtgat ctgggaacaa agttggctgt atgttgttca tctgggaggc   3600
ccatttggca ttggcggcca agatatcttg taggtttgag ttgtgactca atgtgaatat   3660
agatgaagat tcggtagcgc tcattgtgtt tgtgttgggg gtactagtaa tagtagtagt   3720
agtattagta gtagctgtaa taatagtatt agctgtgtac tgattgaaca aatttattgg   3780
aaggaacaac tacatcaaca aatctctact tcaactggga tagagacacc tctttatata   3840
aatcccggga aacgggcctc tccttgtttt cccattatca tttccctctc tttctcactc   3900
catcaccggg ccacacggta tttgtcaacc tcatggccca caaggggggg ggggccacat   3960
ttcccactcc actcgcactc cactcgcgga aggtttctcc ccggggtcac cccattctca   4020
cctggaaaat gagtcctatc cgaaaaaaac tgttttctcg ttccatcttg tgaccgtcgc   4080
ccattatcgc cgtcgcgtcg ccgtcgcgtc gctgataatg cccaaacaat agaaatcgac   4140
gggacgatct gccctaggca tgccggtaga ggtgtggtca ataagagcga cctcatgcta   4200
```

```
tacctgagaa agcaacctga cctacaggaa agagttactc aagaataaga attttcgttt   4260
taaaacctaa gagtcacttt aaaatttgta tacacttatt ttttttataa cttatttaat   4320
aataaaaatc ataaatcata agaaattcgc ttatttagaa gtgtcaacaa cgtatctacc   4380
aacgatttga cccttttcca tcttttcgta aatttctggc aaggtagaca agccgacaac   4440
cttgattgga gacttgacca aacctctggc gaagaagtcc aaagcttgga agatcttact   4500
tttttgggga tgggggtagg gtttcttctt ctaggacaac caacaaatct gatgcgtcaa   4560
cactttcacc atccttaatg aaaacgtctt taacttgacc atctgctggt gaagagacaa   4620
ccatttccat tttcatggca ctcaaaacag caatcgattc gcccttttc accaaagacc    4680
ctttatgtac tttaacttct atgataacac cagccattgg tgcaccgatt tggtgagtat   4740
cgtggacatc agcctttggt ttagcaacag attgtatgtt ttgtgacttg tctgcaactc   4800
tgatctttct taattcaccg ttcaattcaa aatacacttc tctttgccca gttttcttat   4860
ttaagtcacc aacagcttgc aatttgataa tcaaagtctt accttgttcg atggtgactt   4920
cgatttcttc atcaggttct gctggtgcta ggaaattttt ggttggtaga actgataaat   4980
caccgtatgt ttctctgatc ttttggaaat cttcatagac ccttggatac atattgtaag   5040
aagcaacatc gcattcatca atatcaccga atctgttctg caagtcttct ctaatttttt   5100
cgagatcaaa tggttctaat tctaaacctg gacggcacgt caactttctt ctcttgtttc   5160
tcaatacatc agatcttaat ggttctggga acccaccgta tggttgacca attaaacctt   5220
caaaaaagtc cataacagag tcaggaaagt ccaaagaatt agctaaacgt ctaatatcgt   5280
cggaagtcag tttgttagaa accatgaatt gagctaaatc accgacaacc ttagaagttg   5340
gggtaacttt aacaatatct cccagtaggt aattggcttc tctgtaagct cttttagttt   5400
cagcccattg ttcaccaaga cccagttgtt gagcttggaa taacaagtta gtcaattgac   5460
cacctgggat ttcatgttgg taaacttctg gatctggtcc cttcaagtcg gcctcgaaac   5520
aagaatacaa cagtctcatt tcggcccagt atgcatctaa ttcacgaaca tgctcaacgt   5580
taatcccagt atcaatgtta ccttctaatg aagccaacag tgcattaatt gatggttggg   5640
aagttaagcc cgacattgaa ttgatagcta catcgacaac atcagcacct gctagggcac   5700
atgcagtcat agacgcaaca gcagtacctg cggagtcatg actgtgaaca tgaattggta   5760
aatccggata tctggttctt agggagccaa ttaataattt ggcagcggcc ggtttcatag   5820
tacctgccat atccttaata cccaagatat gtgtacccat ttgaactatt ttttcaacaa   5880
cttctaggta gtagtctaag ttgtatttct tacctggctg aagcatgtca ccagagtaac   5940
aaacagtagc ttcgacaaca ccaccggcct tcttgacagc attcacacca acttttaatt   6000
gttctaaatc attcaaggca tcaaaaactc taaatatatc aacaccatta tccttggctt   6060
gcttgacaaa atggtcaata gcattgtcag gtaatgaaga gtaagccaca ccgttggcac   6120
cacgtaataa catttggaat ggaatattag gcaccagaga tcttaatttt ctcagacgtt   6180
cccatggatc ctcatgcaag aatctcattg caacgtcgaa tgtagcacca ccccaacatt   6240
ctaaagcgaa agcacctgca agggcatgtg cggttgttgg agcgattgta gccaaatcgt   6300
gggttctgac tcttgttgca agtagagatt gatgagcgtc tctccaggtg gtgtccatca   6360
gtagagtacc attgaactgt ctgacttgct tggcaaattc agatggtccc ttttccagta   6420
gcacttgtct ccatccggat ggtggtgcag actttgtaac gttgatgaca ttgccctgag   6480
catcgtgcaa atgggggaca cttggatttg attttagttt tggcaagcca atttgaccct   6540
```

-continued

```
taatagaaga accgttaact gccaagtctg ccaaatagtg taacagtttt tgcgctctgt   6600
tttgtgacga taccatttgg aacagttgtg gggtgtcgtc aataaaagtc gtccagtatg   6660
taccctcaat aaaaactgga ttggtcaaaa gagtcaatag gaagggaatg ttggtcttaa   6720
cacctctgat tctgaattcg atcagggcac gaatcatctt cctacggacg atttcataag   6780
tagaaccaga gcatgaacat ttgaccagca ttgagtcgta gtgaggcgag atagtagcac   6840
ctgcataagc gttaccaccg tccaatctca caccattacc accggcagaa cgatagacct   6900
ccaggcgacc ggtatccggt tggaaattct tagagggatc ttcagtggta atacgacatt   6960
ggatggaaaa cccacgggtg gtgattttat cctgtaatag acctagttga gtcaaagtgg   7020
cacctgcggc aatctggatt tgggcagaaa caatgtcaat accggtgatt tcttcagtga   7080
tggtatgctc cacttgaatt cttggattaa tttcaatgaa atagtgtctg ttttggttgt   7140
caaccaagaa ttcggcggta cctgcgtttc tgtaaccaca taccttagct aatttaacag   7200
catctgtcaa aatagcgtca cgaacttcac ggggcaaagt ctttgctgga gcgacttcga   7260
caactttttg gtgtcttctt tgcacagaac agtctctttc gaaaagatga accacgtttc   7320
cgtggttatc agccaacaat tgaacttcaa tatgctttgg cttgtccaag aatctttcca   7380
caaagcaggt accattaccg aaggcagtac gggcttcgga ggtagcacgt tgaaaggcat   7440
ctgccacgtc gtcaccttct ctaacgactc tcatacctct accaccacca ccaaaggcgg   7500
ccttaatgat caccgggtag ccgtattcat taacgaagtc aagtgcctct tgcacagttt   7560
cgataggtcc tggagtaccg ggaacggtag gaacgttagc tcttgctgcc aagtgtctgg   7620
cagagacttt gtcacccaca gagtcaataa cttcagctgg agggccgatc caagtgatac   7680
cggccttcac tactttgtcg gcaaattccg aattttcaga caagaaccca taacctggat   7740
ggatgaaatc caccttatgc ttctttgcaa tttcgatgat ctcgtccatt gccaagtaag   7800
cacccacagg tgtatactgg ccctcctccc cgataacata cgcttcgtcc gccttcaacc   7860
tgtgcattga aagacggtcc tcatgggagt atatggcgat ggttctcata gacagctcat   7920
gagcagatct aaaaattcta atcggaattt cacctctatt ggcgaccaag atcttattct   7980
tttcgccgag caaactgaaa ttgtccctaa gaccggccaa tttcttgcta ctgctcattc   8040
tagatcttgt tgttgttgtt gtcgttgttt ttgtttttgt tgtgttagta taacgtgtat   8100
aattaacagt ggttgattct atactgttaa atcggaagaa acggcaaaca agtcctctca   8160
gcaacatcaa ctggcaaaag acaaaacccg ccttttatag actccccgga gtgtcgaaat   8220
atgacttccc ggcaacgagt tctccgggtg ggtgatagc gggtcctttc gctacctatt   8280
tttcgccccc ccccatcctc catcctccat gccccatact ccatgccccc tcgaggattt   8340
acagtggggg cctcacttct cgcggactct cttccagaaa ttgcacgatt acccaatatg   8400
gtccttcagg agtgacacaa cctgaaaggt ggcggcgcaa aatgtattgg cagagcctat   8460
tggtggagcc tattgggagc agctatagta aagaggagta gtagacagta gtagacaata   8520
gtagggagta gttgaagggt gtcaattttg aatatcgtga gtgcattaac taactataga   8580
agctaagtag cataaataaa taaatataaa tataaatata gatataaatg taggtgtgta   8640
aacgtggaca ttgatgttgc cgttgcagca aggatccgta tcatttgtag cccacgccac   8700
ccggaaaaac caccattgtc ctcagcagtc cgccaaaata tggatgcgct caatcaactt   8760
tccctccccc gtcaatgcca aaaggataac gacacactat taagagcgca tcatttgtaa   8820
aagccgagga agggggatac gctaaccgga gacgtctcgc ctcactctcg gagctgagcc   8880
gccctcctta agaaattcat gggaagaaca cccttcgcgg cttctgaacg gctcgccctc   8940
```

```
gtccattggt cacctcacag tggcaactaa taaggacatt atagcaatag aaattaaaat   9000
ggtgcacaga aatacaatag gatcgaatag gataggatac aataagatac ggaatattag   9060
actatactgt gatacggtac ggtacgatac gctacgatac gatacgatag aggataccac   9120
ggatataacg tagtattatt tttcattatt gggggttttt ttctgtttga attttccacg   9180
tcaagagtat cccatctgac aggaaccgat ggactcgtca cagtacctat cgcccgagtt   9240
caatccatgg acgcttcggg tgaaggatct tcgtccgctg ttggcaagcc atgggatcag   9300
ggcgtcgcca agggacagaa aggcggatct tgtacgtctc ttcaacacag agctgcgtcc   9360
gaaacttact gagagtctta acaccaataa tcccaaaaac aacaacaaca atacagatac   9420
tatagacact atagacacta tagacactac taacancccct ttaaagcgcc gccgattaag   9480
caatgttgat gagccgtcaa ttccatatac tcagctggcg gccgcggatc tgccggtctc   9540
cctatagtga gtcgtattaa tttcgataag ccaggttaac ctgcattaat gaatcggcca   9600
acgcgcgggg agaggcggtt tgcgtattgg gcgctcttcc gcttcctcgc tcactgactc   9660
gctgcgctcg gtcgttcggc tgcggcgagc ggtatcagct cactcaaagg cggtaatacg   9720
gttatccaca gaatcagggg ataacgcagg aaagaacatg tgagcaaaag gccagcaaaa   9780
ggccaggaac cgtaaaaagg ccgcgttgct ggcgtttttc cataggctcc gcccccctga   9840
cgagcatcac aaaaatcgac gctcaagtca gaggtggcga aacccgacag gactataaag   9900
ataccaggcg tttccccctg gaagctccct cgtgcgctct cctgttccga ccctgccgct   9960
taccggatac ctgtccgcct ttctcccttc gggaagcgtg gcgctttctc aatgctcacg  10020
ctgtaggtat ctcagttcgg tgtaggtcgt tcgctccaag ctgggctgtg tgcacgaacc  10080
ccccgttcag cccgaccgct gcgccttatc cggtaactat cgtcttgagt ccaacccggt  10140
aagacacgac ttatcgccac tggcagcagc cactggtaac aggattagca gagcgaggta  10200
tgtaggcggt gctacagagt tcttgaagtg gtggcctaac tacggctaca ctagaaggac  10260
agtatttggt atctgcgctc tgctgaagcc agttaccttc ggaaaaagag ttggtagctc  10320
ttgatccggc aaacaaacca ccgctggtag cggtggtttt tttgtttgca agcagcagat  10380
tacgcgcaga aaaaaaggat ctcaagaaga tcctttgatc ttttctacgg ggtctgacgc  10440
tcagtggaac gaaaactcac gttaagggat tttggtcatg agattatcaa aaaggatctt  10500
cacctagatc cttttaaatt aaaaatgaag ttttaaatca atctaaagta tatatgagta  10560
aacttggtct gacagttacc aatgcttaat cagtgaggca cctatctcag cgatctgtct  10620
atttcgttca tccatagttg cctgactccc cgtcgtgtag ataactacga tacgggaggg  10680
cttaccatct ggccccagtg ctgcaatgat accgcgagac ccacgctcac cggctccaga  10740
tttatcagca ataaaccagc cagccggaag ggccgagcgc agaagtggtc ctgcaacttt  10800
atccgcctcc atccagtcta ttaattgttg ccgggaagct agagtaagta gttcgccagt  10860
taatagtttg cgcaacgttg ttgccattgc tacaggcatc gtggtgtcac gctcgtcgtt  10920
tggtatggct tcattcagct ccggttccca acgatcaagg cgagttacat gatcccccat  10980
gttgtgcaaa aaagcggtta gctccttcgg tcctccgatc gttgtcagaa gtaagttggc  11040
cgcagtgtta tcactcatgg ttatggcagc actgcataat tctcttactg tcatgccatc  11100
cgtaagatgc ttttctgtga ctggtgagta ctcaaccaag tcattctgag aatagtgtat  11160
gcggcgaccg agttgctctt gcccggcgtc aatacgggat aataccgcgc cacatagcag  11220
aactttaaaa gtgctcatca ttggaaaacg ttcttcgggg cgaaaactct caaggatctt  11280
```

```
accgctgttg agatccagtt cgatgtaacc cactcgtgca cccaactgat cttcagcatc  11340

ttttactttc accagcgttt ctgggtgagc aaaaacagga aggcaaaatg ccgcaaaaaa  11400

gggaataagg gcgacacgga aatgttgaat actcatactc ttcctttttc aatattattg  11460

aagcatttat cagggttatt gtctcatgag cggatacata tttgaatgta tttagaaaaa  11520

taaacaaata ggggttccgc gcacatttcc ccgaaaagtg ccacctgacg tctaagaaac  11580

cattattatc atgacattaa cctataaaaa taggcgtatc acgaggccct ttcgtctcgc  11640

gcgtttcggt gatgacggtg aaaacctctg acacatgcag ctcccggaga cggtcacagc  11700

ttgtctgtaa gcggatgccg ggagcagaca agcccgtcag ggcgcgtcag cgggtgttgg  11760

cgggtgtcgg ggctggctta actatgcggc atcagagcag attgtactga gagtgcacca  11820

tatggacata ttgtcgttag aacgcggcta caattaatac ataaccttat gtatcataca  11880

catacgattt aggtgacact ata                                          11903


<210> SEQ ID NO 9
<211> LENGTH: 11151
<212> TYPE: DNA
<213> ORGANISM: Artificial Sequence
<220> FEATURE:
<223> OTHER INFORMATION: DNA construct pMIPk113
<220> FEATURE:
<221> NAME/KEY: misc_feature
<222> LOCATION: (371)..(371)
<223> OTHER INFORMATION: n is a, c, g, or t
<220> FEATURE:
<221> NAME/KEY: misc_feature
<222> LOCATION: (7862)..(7862)
<223> OTHER INFORMATION: n is a, c, g, or t

<400> SEQUENCE: 9

aattcttgct gcaacggcaa catcaatgtc cacgtttaca cacctacatt tatatctata     60

tttatattta tatttattta tttatgctac ttagcttcta tagttagtta atgcactcac    120

gatattcaaa attgacaccc ttcaactact ccctactatt gtctactact gtctactact    180

cctctttact atagctgctc ccaataggct ccaccaatag gctctgtcaa tacattttgc    240

gccgccacct ttcaggttgt gtcactcctg aaggaccata ttgggtaatc gtgcaatttc    300

tggaagagag tgccgcgaga agtgaggccc ccactgtaaa tcctcgaggg ggcatggagt    360

atggggcatg naggatggag gatggggggg gggggggaaa ataggtagcg aaaggacccg    420

ctatcacccc acccggagaa ctcgttgccg ggaagtcata tttcgacact ccggggagtc    480

tataaaaggc gggttttgtc ttttgccagt tgatgttgct gagaggactt gtttgccgtt    540

tcttccgatt taacagtata gaatcaacca ctgttaatta tacacgttat actaacacaa    600

caaaaacaaa aacaacgaca acaacaacaa caatgtttgc tttctacttt ctcaccgcat    660

gcaccacttt gaagggtgtt ttcggagttt ctccgagtta caatggtctt ggtctcaccc    720

cacagatggg ttgggacagc tggaatacgt ttgcctgcga tgtcagtgaa cagctacttc    780

tagacactgc tgatagaatt tctgacttgg ggctaaagga tatgggttac aagtatgtca    840

tcctagatga ctgttggtct agcggcaggg attccgacgg tttcctcgtt gcagacaagc    900

acaaatttcc caacggtatg ggccatgttg cagaccacct gcataataac agctttcttt    960

tcggtatgta ttcgtctgct ggtgagtaca cctgtgctgg gtaccctggg tctctggggc   1020

gtgaggaaga agatgctcaa ttctttgcaa ataaccgcgt tgactacttg aagtatgata   1080

attgttacaa taaaggtcaa tttggtacac cagacgtttc ttaccaccgt tacaaggcca   1140

tgtcagatgc tttgaataaa actggtaggc ctattttcta ttctctatgt aactggggtc   1200
```

```
aggatttgac attttactgg ggctctggta tcgccaattc ttggagaatg agcggagata   1260
ttactgctga gttcacccgt ccagatagca gatgtccctg tgacggtgac gaatatgatt   1320
gcaagtacgc cggtttccat tgttctatta tgaatattct taacaaggca gctccaatgg   1380
ggcaaaatgc aggtgttggt ggttggaacg atctggacaa tctagaggtc ggagtcggta   1440
atttgactga cgatgaggaa aaggcccatt tctctatgtg ggcaatggta aagtccccac   1500
ttatcattgg tgccgacgtg aatcacttaa aggcatcttc gtactcgatc tacagtcaag   1560
cctctgtcat cgcaattaat caagatccaa agggtattcc agccacaaga gtctggagat   1620
attatgtttc agacaccgat gaatatggac aaggtgaaat tcaaatgtgg agtggtccgc   1680
ttgacaatgg tgaccaagtg gttgctttat tgaatggagg aagcgtagca agaccaatga   1740
acacgacctt ggaagagatt ttctttgaca gcaatttggg ttcaaaggaa ctgacatcga   1800
cttgggatat ttacgactta tgggccaaca gagttgacaa ctctacggcg tctgctatcc   1860
ttgaacagaa taaggcagcc accggtattc tctacaatgc tacagagcag tcttataaag   1920
acggtttgtc taagaatgat acaagactgt ttggccagaa aattggtagt ctttctccaa   1980
atgctatact taacacaact gttccagctc atggtatcgc cttctatagg ttgagaccct   2040
cggcttaagc tcaatgttga gcaaagcagg acgagaaaaa aaaaaataat gattgttaag   2100
aagttcatga aaaaaaaaag gaaaaatact caaatactta taacagagtg attaaataat   2160
aaacggcagt ataccctatc aggtattgag atagttttat ttttgtaggt atataatctg   2220
aagcctttga actattttct cgtatatatc atggagtata cattgcatta gcaacattac   2280
atactaggat ctctagacct aataacttcg tatagcatac attatacgaa gttatattaa   2340
gggttgtcga cgatatggat atggatatgg atatggagat gaatttgaat ttagatttgg   2400
gtcttgattt ggggttggaa ttaaaagggg ataacaatga gggttttcct gttgatttaa   2460
acaatggacg tgggaggtga ttgatttaac ctgatccaaa aggggtatgt ctattttttta   2520
gagagtgttt ttgtgtcaaa ttatggtaga atgtgtaaag tagtataaac tttcctctca   2580
aatgacgagg tttaaaacac cccccgggtg agccgagccg agaatggggc aattgttcaa   2640
tgtgaaatag aagtatcgag tgagaaactt gggtgttggc cagccaaggg ggggggggaa   2700
ggaaaatggc gcgaatgctc aggtgagatt gttttggaat tgggtgaagc gaggaaatga   2760
gcgacccgga ggttgtgact ttagtggcgg aggaggacgg aggaaaagcc aagagggaag   2820
tgtatataag gggagcaatt tgccaccagg atagaattgg atgagttata attctactgt   2880
atttattgta taatttattt ctccttttgt atcaaacaca ttacaaaaca cacaaaacac   2940
acaaacaaac acaattacaa aaattaatta aaaaatgacc atcaccatca ccgtcgaaaa   3000
ggatggttat tacgaagtta acggtactag acaagaacct accgtttcct tgtatgttat   3060
tccagctgct tctaagttga gaagaatgtt gaaagatacc aaggacttga tcgtttgtcc   3120
aggtgtttat gatggtttgt ctgctagaat tgctatggaa gttggtttca agggtttgta   3180
tatgactggt gctggtacta ctgcttcaag attgggtatg gctgatttgg gtttggctca   3240
attgcatgat atgaagacta acgctgaaat gattgctaac ttggacccat ttggtccacc   3300
attgattgct gatatggata ctggttatgg tggtccattg atggtttcta agtccgtcca   3360
acaatatatt caagctggtg ttgctggttt ccacatcgaa gatcaaattc aaaacaagag   3420
atgcggtcac ttgaacggta aaaaagttgt tggtttggaa gaatacttga tgagaattag   3480
agctgccaag ttgaccaagg atagattgca ttctgatatt gtcttgatcg ctagaactga   3540
```

-continued

```
tgccttgcaa caacatggtt acgatgaatg cattagaaga ttgaaggctg ccagagatat   3600
tggtgctgat gttggtttat tggaaggttt cacctctaaa gaacaagcta gacaagctgt   3660
tcaagatttg gctccatggc ctttgttgtt gaatatggtt gaaaatggtg cctccccatt   3720
gattactaca aaagaagctg aagaaatggg tttcagaatt atgattttct ccttcgctac   3780
tattacccca gcttacatgg gtattaaggc tactttggaa agattgaaaa ccgatggtgt   3840
tgttggtgta ccagaaggtt taggtccaag aactattttc gaagtttgcg gtttgatgga   3900
ctccatgaag gttgatactg aatctggtaa cgatggtttt gctgaaggtg tttgattaat   3960
taacccatgt ctctactggt ggtggtgctt ctttggaatt attggaaggt aaggaattgc   4020
caggtgttgc tttcttatcc gaaaagaaat aaattgaatt gaattgaaat cgatagatca   4080
atttttttct tttctctttc cccatccttt acgctaaaat aatagtttat tttatttttt   4140
gaatattttt tatttatata cgtatatata gactattatt tatcttttaa tgattattaa   4200
gatttttatt aaaaaaaaat tcgctcctct tttaatgcct ttatgcagtt tttttttccc   4260
attcgatatt tctatgttcg ggttcagcgt attttaagtt taataactcg aaaattctgc   4320
gttcgttaag tcgacggatc cttgctgcaa cggcaacatc aatgtccacg tttacacacc   4380
tacatttata tctatattta tatttatatt tatttattta tgctacttag cttctatagt   4440
tagttaatgc actcacgata ttcaaaattg acacccttca actactccct actattgtct   4500
actactgtct actactcctc tttactatag ctgctcccaa taggctccac caataggctc   4560
tgccaataca ttttgcgccg ccacctttca ggttgtgtca ctcctgaagg accatattgg   4620
gtaatcgtgc aatttctgga agagagtccg cgagaagtga ggccccccact gtaaatcctc   4680
gagggggcat ggagtatggg gcatggagga tggaggatgg ggggggcgga aaaataggta   4740
gcgaaaggac ccgctatcac ccccacccgga gaactcgttg ccgggaagtc atatttcgac   4800
actccgggga gtctataaaa ggcgggtttt gtcttttgcc agttgatgtt gctgagagga   4860
cttgtttgcc gtttcttccg atttaacagt atagaatcaa ccactgttaa ttatacacgt   4920
tatactaaca caacaaaaac aaaaacaacg acaacaacaa caacaagatc catggaccaa   4980
ttggtgaaaa ctgaagtcac caagaagtct tttactgctc ctgtacaaaa ggcttctaca   5040
ccagttttaa ccaataaaac agtcatttct ggatcgaaag tcaaaagttt atcatctgcg   5100
caatcgagct catcaggacc ttcatcatct agtgaggaag atgattcccg cgatattgaa   5160
agcttggata agaaaatacg tcctttagaa gaattagaag cattattaag tagtggaaat   5220
acaaaacaat tgaagaacaa agaggtcgct gccttggtta ttcacggtaa gttacctttg   5280
tacgctttgg agaaaaaatt aggtgatact acgagagcgg ttgcggtacg taggaaggct   5340
ctttcaattt tggcagaagc tcctgtatta gcatctgatc gtttaccata taaaaattat   5400
gactacgacc gcgtatttgg cgcttgttgt gaaaatgtta taggttacat gcctttgccc   5460
gttggtgtta taggcccctt ggttatcgat ggtacatctt atcatatacc aatggcaact   5520
acagagggtt gtttggtagc ttctgccatg cgtggctgta aggcaatcaa tgctggcggt   5580
ggtgcaacaa ctgttttaac taaggatggt atgacaagag gcccagtagt ccgtttccca   5640
actttgaaaa gatctggtgc ctgtaagata tggttagact cagaagaggg acaaaacgca   5700
attaaaaaag cttttaactc tacatcaaga tttgcacgtc tgcaacatat tcaaacttgt   5760
ctagcaggag atttactctt catgagattt agaacaacta ctggtgacgc aatgggtatg   5820
aatatgattt ctaaaggtgt cgaatactca ttaaagcaaa tggtagaaga gtatggctgg   5880
gaagatatgg aggttgtctc cgtttctggt aactactgta ccgacaaaaa accagctgcc   5940
```

```
atcaactgga tcgaaggtcg tggtaagagt gtcgtcgcag aagctactat tcctggtgat   6000
gttgtcagaa aagtgttaaa aagtgatgtt tccgcattgg ttgagttgaa cattgctaag   6060
aatttggttg gatctgcaat ggctgggtct gttggtggat ttaacgcaca tgcagctaat   6120
ttagtgacag ctgttttctt ggcattagga caagatcctg cacaaaatgt tgaaagttcc   6180
aactgtataa cattgatgaa agaagtggac ggtgatttga gaatttccgt atccatgcca   6240
tccatcgaag taggtaccat cggtggtggt actgttctag aaccacaagg tgccatgttg   6300
gacttattag gtgtaagagg cccgcatgct accgctcctg gtaccaacgc acgtcaatta   6360
gcaagaatag ttgcctgtgc cgtcttggca ggtgaattat ccttatgtgc tgccctagca   6420
gccggccatt tggttcaaag tcatatgacc cacaacagga aacctgctga accaacaaaa   6480
cctaacaatt tggacgccac tgatataaat cgtttgaaag atgggtccgt cacctgcatt   6540
aaatcctaaa cttagtcata cgtcattggt attctcttga aaaagaagca caacagcacc   6600
atgtgggatc ttccaagctt tggacttctt cgccagaggt ttggtcaagt ctccaatcaa   6660
ggttgtcggc ttgtctacct tgccagaaat ttacgaaaag atggaaaagg gtcaaatcgt   6720
tggtagatac gttgttgaca cttctaaata agcgaatttc ttatgattta tgatttttat   6780
tattaaataa gttataaaaa aaataagtgt atacaaattt taaagtgact cttaggtttt   6840
aaaacgaaaa ttcttattct tgagtaactc tttcctgtag gtcaggttgc tttctcaggt   6900
atagcatgag gtcgctctta ttgaccacac ctctaccggc atgccgagca aatgcctgca   6960
aatcgctccc catttcaccc aattgtagat atgctaactc cagcaatgag ttgatgaatc   7020
tcggtgtgta ttttatgtcc tcagaggaca acacctgttg taatcgttct tccacacgga   7080
tccgtatcat ttgtagccca cgccacccgg aaaaaccacc attgtcctca gcagtccgcc   7140
aaaatatgga tgcgctcaat caactttccc tcccccgtca atgccaaaag gataacgaca   7200
cactattaag agcgcatcat ttgtaaaagc cgaggaaggg ggatacgcta accggagacg   7260
tctcgcctca ctctcggagc tgagccgccc tccttaagaa attcatggga agaacaccct   7320
tcgcggcttc tgaacggctc gccctcgtcc attggtcacc tcacagtggc aactaataag   7380
gacattatag caatagaaat taaaatggtg cacagaaata caataggatc gaataggata   7440
ggatacaata agatacggaa tattagacta tactgtgata cggtacggta cgatacgcta   7500
cgatacgata cgatagagga taccacggat ataacgtagt attatttttc attattgggg   7560
gtttttttct gtttgaattt tccacgtcaa gagtatccca tctgacagga accgatggac   7620
tcgtcacagt acctatcgcc cgagttcaat ccatggacgc ttcgggtgaa ggatcttcgt   7680
ccgctgttgg caagccatgg gatcagggcg tcgccaaggg acagaaaggc ggatcttgta   7740
cgtctcttca acacagagct gcgtccgaaa cttactgaga gtcttaacac caataatccc   7800
aaaaacaaca acaacaatac agatactata gacactatag acactataga cactactaac   7860
ancccttaa agcgccgccg attaagcaat gttgatgagc cgtcaattcc atatactctg   7920
cagcgtacga agcttcagct ggcggccgcg ttctatagtg tcacctaaat cgtatgtgta   7980
tgatacataa ggttatgtat taattgtagc cgcgttctaa cgacaatatg tccatatggt   8040
gcactctcag tacaatctgc tctgatgccg catagttaag ccagccccga cacccgccaa   8100
cacccgctga cgcgccctga cgggcttgtc tgctcccggc atccgcttac agacaagctg   8160
tgaccgtctc cgggagctgc atgtgtcaga ggttttcacc gtcatcaccg aaacgcgcga   8220
gacgaaaggg cctcgtgata cgcctatttt tataggttaa tgtcatgata ataatggttt   8280
```

-continued

```
cttagacgtc aggtggcact tttcggggaa atgtgcgcgg aacccctatt tgtttatttt   8340
tctaaataca ttcaaatatg tatccgctca tgagacaata accctgataa atgcttcaat   8400
aatattgaaa aaggaagagt atgagtattc aacatttccg tgtcgccctt attccctttt   8460
ttgcggcatt ttgccttcct gtttttgctc acccagaaac gctggtgaaa gtaaaagatg   8520
ctgaagatca gttgggtgca cgagtgggtt acatcgaact ggatctcaac agcggtaaga   8580
tccttgagag ttttcgcccc gaagaacgtt ttccaatgat gagcactttt aaagttctgc   8640
tatgtggcgc ggtattatcc cgtattgacg ccgggcaaga gcaactcggt cgccgcatac   8700
actattctca gaatgacttg gttgagtact caccagtcac agaaaagcat cttacggatg   8760
gcatgacagt aagagaatta tgcagtgctg ccataaccat gagtgataac actgcggcca   8820
acttacttct gacaacgatc ggaggaccga aggagctaac cgcttttttg cacaacatgg   8880
gggatcatgt aactcgcctt gatcgttggg aaccggagct gaatgaagcc ataccaaacg   8940
acgagcgtga caccacgatg cctgtagcaa tggcaacaac gttgcgcaaa ctattaactg   9000
gcgaactact tactctagct tcccggcaac aattaataga ctggatggag gcggataaag   9060
ttgcaggacc acttctgcgc tcggcccttc cggctggctg gtttattgct gataaatctg   9120
gagccggtga gcgtgggtct cgcggtatca ttgcagcact ggggccagat ggtaagccct   9180
cccgtatcgt agttatctac acgacgggga gtcaggcaac tatggatgaa cgaaatagac   9240
agatcgctga gataggtgcc tcactgatta agcattggta actgtcagac caagtttact   9300
catatatact ttagattgat ttaaaacttc atttttaatt taaaaggatc taggtgaaga   9360
tcctttttga taatctcatg accaaaatcc cttaacgtga gttttcgttc cactgagcgt   9420
cagaccccgt agaaaagatc aaaggatctt cttgagatcc tttttttctg cgcgtaatct   9480
gctgcttgca aacaaaaaaa ccaccgctac cagcggtggt ttgtttgccg gatcaagagc   9540
taccaactct ttttccgaag gtaactggct tcagcagagc gcagatacca aatactgtcc   9600
ttctagtgta gccgtagtta ggccaccact tcaagaactc tgtagcaccg cctacatacc   9660
tcgctctgct aatcctgtta ccagtggctg ctgccagtgg cgataagtcg tgtcttaccg   9720
ggttggactc aagacgatag ttaccggata aggcgcagcg gtcgggctga acggggggtt   9780
cgtgcacaca gcccagcttg gagcgaacga cctacaccga actgagatac ctacagcgtg   9840
agcattgaga aagcgccacg cttcccgaag ggagaaaggc ggacaggtat ccggtaagcg   9900
gcagggtcgg aacaggagag cgcacgaggg agcttccagg gggaaacgcc tggtatcttt   9960
atagtcctgt cgggtttcgc cacctctgac ttgagcgtcg atttttgtga tgctcgtcag  10020
gggggcggag cctatggaaa aacgccagca acgcggcctt tttacggttc ctggcctttt  10080
gctggccttt tgctcacatg ttctttcctg cgttatcccc tgattctgtg gataaccgta  10140
ttaccgcctt tgagtgagct gataccgctc gccgcagccg aacgaccgag cgcagcgagt  10200
cagtgagcga ggaagcggaa gagcgcccaa tacgcaaacc gcctctcccc gcgcgttggc  10260
cgattcatta atgcaggtta acctggctta tcgaaattaa tacgactcac tatagggaga  10320
ccggcagatc cgcggccgca atagagagtg acctatccaa gctttggggg tctaagtttt  10380
aatggcccag ggaatcatta cttttttttc tcaatccttg atggataaaa gtattacata  10440
cgtacaggat tgtgtattag tgtatttcgt tatatgatta aacaaagttt atagattgta  10500
aagtagacgt aaagtttagt aattcatttt aatgttcatt ttacattcag atgtcattaa  10560
gcggctttag agttgatttc atcagataat ttagcttgag caaccaagat ttctggagca  10620
tcgaattcat ccaagaataa ttcaatgact ctaatcttat cttccttgtt gaatgcttca  10680
```

-continued

```
tccttcatca aagcgtccaa gtccttagcg gatttaacaa catggttttc atattgggtc  10740
ttgtcagcaa agagcttcaa taacaattgg tgatcccatg gttgaatttg gttgtagtcc  10800
tcatgacgac cgtggatcaa cttttcgata gtgtaacctc tgttgtttaa gatgaagatg  10860
tatggcttga tgttccatct tgcagcatct gagattgatt ggacagtcaa ttgtaaagaa  10920
ccatcaccaa taaacaaaac agttcttctt tcttgttcgc cagtttgttt gtgtgcatct  10980
tcagcagcaa atgcagcacc aactgcagct ggtaaggaga aaccaatgga accccataag  11040
acttgggaga tagactttga atctcttggt atgggtagcc aagactagtc gatatcacct  11100
aataacttcg tatagcatac attatacgaa gttatattaa gggttctcga g           11151
```